United States Patent
Cook et al.

(10) Patent No.: US 9,075,042 B2
(45) Date of Patent: Jul. 7, 2015

(54) DIAGNOSTIC SYSTEMS AND CARTRIDGES

(71) Applicant: Wellstat Diagnostics, LLC, Gaithersburg, MD (US)

(72) Inventors: Richard Alan Cook, Derwood, MD (US); Charles Quentin Davis, Frederick, MD (US); Jason Charles Harley, Gaithersburg, MD (US); Jonathan Leland, Gaithersburg, MD (US); Rober Krikor Matikyan, Potomac, MD (US); Jeffrey Howard Peterman, Silver Spring, MD (US)

(73) Assignee: Wellstat Diagnostics, LLC, Gaithersburg, MD (US)

( * ) Notice: Subject to any disclaimer, the term of this patent is extended or adjusted under 35 U.S.C. 154(b) by 0 days.

(21) Appl. No.: 13/844,527

(22) Filed: Mar. 15, 2013

(65) Prior Publication Data

US 2013/0337432 A1 Dec. 19, 2013

Related U.S. Application Data

(63) Continuation-in-part of application No. PCT/US2012/067041, filed on Nov. 29, 2012.

(60) Provisional application No. 61/647,272, filed on May 15, 2012.

(51) Int. Cl.
*A61J 1/06* (2006.01)
*G01N 33/50* (2006.01)
(Continued)

(52) U.S. Cl.
CPC .............. *G01N 33/50* (2013.01); *G01N 21/66* (2013.01); *F04B 49/065* (2013.01); *H05B 1/025* (2013.01);
(Continued)

(58) Field of Classification Search
CPC ................ B01L 2200/10; B01L 2300/0861; B01L 3/502
USPC ......... 422/52, 73, 82.01, 82.05, 82.06, 82.07, 422/82.08, 82.09, 82.11, 407, 500, 501, 422/502, 503, 504, 507, 512, 513, 547, 549, 422/554, 560, 562, 570; 436/17, 43, 63, 94, 436/149, 164, 172, 174, 177, 517, 518, 805, 436/809; 435/4, 6.1, 6.11, 6.12, 7.1, 7.92, 435/29, 288.1, 288.5
See application file for complete search history.

(56) References Cited

U.S. PATENT DOCUMENTS 3,705,100 A 12/1972 Blatt et al.
4,212,742 A 7/1980 Solomon et al.
(Continued)

FOREIGN PATENT DOCUMENTS

EP 486059 1/1997
EP 1489303 B1 12/2004
(Continued)

OTHER PUBLICATIONS

Ascoli, et al., "Drug Binding to Human Serum Albumin: Abridged Review of Results Obtained with High-Performance Liquid Chromatography and Circular Dichroism", Chirality, vol. 18:667-679 (2006).
(Continued)

*Primary Examiner* — Dennis M White

(57) ABSTRACT

A clinical diagnostic system is disclosed, including a clinical diagnostic instrument with a disposable cartridge. The disposable cartridge is capable of performing diagnostic and analytical functions including filtering samples such as plasma from whole blood and running assays and collecting measurements of analytes or biomarkers.

101 Claims, 36 Drawing Sheets

(51) Int. Cl.
   *G01N 21/66*   (2006.01)
   *F04B 49/06*   (2006.01)
   *H05B 1/02*    (2006.01)
   *F04B 49/10*   (2006.01)
   *G01N 33/58*   (2006.01)

(52) U.S. Cl.
   CPC ....... *F04B 49/106* (2013.01); *B01L 2300/0861* (2013.01); *B01L 2200/10* (2013.01); *Y10T 436/25* (2015.01); *Y10T 436/2575* (2015.01); *G01N 33/58* (2013.01); *G01N 33/582* (2013.01)

(56) References Cited

U.S. PATENT DOCUMENTS

| | | | |
|---|---|---|---|
| 4,225,410 | A | 9/1980 | Pace |
| 4,228,015 | A | 10/1980 | De Vries et al. |
| 4,301,412 | A | 11/1981 | Hill et al. |
| 4,301,414 | A | 11/1981 | Hill et al. |
| 4,336,121 | A | 6/1982 | Enzer et al. |
| 4,381,775 | A | 5/1983 | Nose' et al. |
| 4,397,725 | A | 8/1983 | Enzer et al. |
| 4,436,610 | A | 3/1984 | Enzer et al. |
| 4,540,492 | A | 9/1985 | Kessler |
| 4,548,498 | A | 10/1985 | Folestad et al. |
| 4,631,130 | A | 12/1986 | Watanabe |
| 4,675,300 | A | 6/1987 | Zare et al. |
| 4,735,718 | A | 4/1988 | Peters |
| 4,735,776 | A | 4/1988 | Yamamoto et al. |
| 4,762,594 | A | 8/1988 | Guruswamy |
| 4,786,394 | A | 11/1988 | Enzer et al. |
| 4,799,393 | A | 1/1989 | Uffenheimer |
| 4,820,129 | A | 4/1989 | Magnussen, Jr. |
| 4,833,087 | A | 5/1989 | Hinckley |
| 4,835,477 | A | 5/1989 | Polaschegg et al. |
| 4,887,458 | A | 12/1989 | Baker et al. |
| 4,929,426 | A | 5/1990 | Bodai et al. |
| 4,965,049 | A | 10/1990 | Lillig et al. |
| 5,023,054 | A | 6/1991 | Sato et al. |
| 5,061,445 | A | 10/1991 | Zoski et al. |
| 5,068,088 | A | 11/1991 | Hall et al. |
| 5,074,977 | A | 12/1991 | Cheung et al. |
| 5,093,268 | A | 3/1992 | Leventis et al. |
| 5,096,582 | A | 3/1992 | Lombardi et al. |
| 5,130,254 | A | 7/1992 | Collier et al. |
| 5,139,328 | A | 8/1992 | Baker et al. |
| 5,139,685 | A | 8/1992 | de Castro et al. |
| 5,143,084 | A | 9/1992 | Macemon et al. |
| 5,147,806 | A | 9/1992 | Kamin et al. |
| 5,155,039 | A | 10/1992 | Chrisope et al. |
| 5,208,163 | A | 5/1993 | Charlton et al. |
| 5,223,219 | A | 6/1993 | Subramanian et al. |
| 5,223,718 | A | 6/1993 | Taboada |
| 5,238,808 | A | 8/1993 | Bard et al. |
| 5,247,243 | A | 9/1993 | Hall et al. |
| 5,279,797 | A | 1/1994 | Burns et al. |
| 5,288,646 | A | 2/1994 | Lundsgaard et al. |
| 5,296,191 | A | 3/1994 | Hall et al. |
| 5,298,224 | A | 3/1994 | Plum |
| 5,302,348 | A | 4/1994 | Cusack et al. |
| 5,310,687 | A | 5/1994 | Bard et al. |
| 5,316,730 | A | 5/1994 | Blake et al. |
| 5,372,946 | A | 12/1994 | Cusak et al. |
| 5,399,486 | A | 3/1995 | Cathey et al. |
| 5,405,510 | A | 4/1995 | Betts et al. |
| 5,416,026 | A | 5/1995 | Davis |
| 5,453,356 | A | 9/1995 | Bard et al. |
| 5,466,416 | A | 11/1995 | Ghaed et al. |
| 5,487,870 | A | 1/1996 | McKinney et al. |
| 5,500,187 | A | 3/1996 | Deoms et al. |
| 5,504,011 | A | 4/1996 | Gavin et al. |
| 5,506,142 | A | 4/1996 | Mahaffey et al. |
| 5,522,255 | A | 6/1996 | Neel et al. |
| 5,525,518 | A | 6/1996 | Lundsgaard et al. |
| 5,527,710 | A | 6/1996 | Nacamulli et al. |
| 5,534,226 | A | 7/1996 | Gavin et al. |
| 5,543,112 | A | 8/1996 | Ghead et al. |
| 5,558,838 | A | 9/1996 | Uffenheimer |
| 5,567,869 | A | 10/1996 | Hauch et al. |
| 5,575,977 | A | 11/1996 | McKinney et al. |
| 5,591,403 | A | 1/1997 | Gavin et al. |
| 5,591,581 | A | 1/1997 | Massey et al. |
| 5,593,638 | A | 1/1997 | Davis |
| 5,597,910 | A | 1/1997 | Gudibande et al. |
| 5,599,447 | A | 2/1997 | Pearl et al. |
| 5,601,727 | A | 2/1997 | Bormann et al. |
| 5,602,037 | A | 2/1997 | Ostgaard et al. |
| 5,610,075 | A | 3/1997 | Stahl-Rees |
| 5,624,637 | A | 4/1997 | Ghaed et al. |
| 5,627,041 | A | 5/1997 | Shartle |
| 5,629,209 | A | 5/1997 | Braun, Sr. et al. |
| 5,635,347 | A | 6/1997 | Link et al. |
| 5,641,623 | A | 6/1997 | Martin |
| 5,643,713 | A | 7/1997 | Liang et al. |
| 5,653,243 | A | 8/1997 | Lauks et al. |
| 5,660,993 | A | 8/1997 | Cathey et al. |
| 5,665,238 | A | 9/1997 | Whitson et al. |
| 5,665,315 | A | 9/1997 | Robert et al. |
| 5,666,967 | A | 9/1997 | Lauks et al. |
| 5,679,519 | A | 10/1997 | Oprandy et al. |
| 5,686,244 | A | 11/1997 | Gudibande et al. |
| 5,698,406 | A | 12/1997 | Cathey et al. |
| 5,700,427 | A | 12/1997 | Ghaed et al. |
| 5,705,402 | A | 1/1998 | Leland et al. |
| 5,714,089 | A | 2/1998 | Bard et al. |
| 5,716,781 | A | 2/1998 | Massey et al. |
| 5,720,922 | A | 2/1998 | Ghaed et al. |
| 5,731,147 | A | 3/1998 | Bard et al. |
| 5,736,404 | A | 4/1998 | Yassinzadeh et al. |
| 5,743,861 | A | 4/1998 | Columbus et al. |
| 5,744,367 | A | 4/1998 | Talley et al. |
| 5,746,974 | A | 5/1998 | Massey et al. |
| 5,747,666 | A | 5/1998 | Willis |
| 5,770,459 | A | 6/1998 | Massey et al. |
| 5,779,650 | A | 7/1998 | Lauks et al. |
| 5,779,976 | A | 7/1998 | Leland et al. |
| 5,795,543 | A | 8/1998 | Poto et al. |
| 5,798,083 | A | 8/1998 | Massey et al. |
| 5,800,781 | A | 9/1998 | Gavin et al. |
| 5,804,400 | A | 9/1998 | Martin et al. |
| 5,821,399 | A | 10/1998 | Zelin |
| 5,827,481 | A | 10/1998 | Bente et al. |
| 5,846,485 | A | 12/1998 | Leland et al. |
| 5,851,488 | A | 12/1998 | Saul et al. |
| RE36,054 | E | 1/1999 | Blake et al. |
| 5,858,676 | A | 1/1999 | Yang et al. |
| 5,882,602 | A | 3/1999 | Savage et al. |
| 5,885,533 | A | 3/1999 | Savage et al. |
| 5,888,826 | A | 3/1999 | Ostgaard et al. |
| 5,912,134 | A | 6/1999 | Shartle |
| 5,914,042 | A | 6/1999 | Ball et al. |
| 5,919,711 | A | 7/1999 | Boyd et al. |
| 5,922,210 | A | 7/1999 | Brody et al. |
| 5,935,779 | A | 8/1999 | Massey et al. |
| 5,945,344 | A | 8/1999 | Hayes et al. |
| 5,962,218 | A | 10/1999 | Leland et al. |
| 5,968,329 | A | 10/1999 | Anderson et al. |
| 5,980,830 | A | 11/1999 | Savage et al. |
| 5,981,294 | A | 11/1999 | Blatt et al. |
| 5,983,734 | A | 11/1999 | Mathur et al. |
| 6,016,712 | A | 1/2000 | Warden et al. |
| 6,048,687 | A | 4/2000 | Kenten et al. |
| 6,057,151 | A | 5/2000 | Greenwood et al. |
| 6,069,014 | A | 5/2000 | Schrier et al. |
| 6,078,782 | A | 6/2000 | Leland et al. |
| 6,082,185 | A | 7/2000 | Saaski |
| 6,087,476 | A | 7/2000 | Kenten et al. |
| 6,096,500 | A | 8/2000 | Oprandy et al. |
| 6,099,760 | A | 8/2000 | Jameison et al. |
| 6,112,888 | A | 9/2000 | Sauro et al. |
| 6,120,986 | A | 9/2000 | Martin |
| 6,132,648 | A | 10/2000 | Zhang et al. |
| 6,132,955 | A | 10/2000 | Talley et al. |
| 6,140,138 | A | 10/2000 | Bard et al. |

(56) References Cited

U.S. PATENT DOCUMENTS

| | | |
|---|---|---|
| 6,146,838 A | 11/2000 | Williams et al. |
| 6,165,708 A | 12/2000 | Liang et al. |
| 6,165,729 A | 12/2000 | Leland et al. |
| 6,174,709 B1 | 1/2001 | Kenten et al. |
| 6,187,267 B1 | 2/2001 | Taylor et al. |
| 6,193,864 B1 | 2/2001 | Leader et al. |
| 6,200,531 B1 | 3/2001 | Liljestrand et al. |
| 6,214,552 B1 | 4/2001 | Heroux et al. |
| 6,217,744 B1 | 4/2001 | Crosby |
| 6,271,041 B1 | 8/2001 | Leland et al. |
| 6,274,087 B1 | 8/2001 | Preston et al. |
| 6,312,591 B1 | 11/2001 | Vassarotti et al. |
| 6,312,896 B1 | 11/2001 | Heroux et al. |
| 6,316,180 B1 | 11/2001 | Martin |
| 6,316,607 B1 | 11/2001 | Massey et al. |
| 6,319,670 B1 | 11/2001 | Sigal et al. |
| 6,319,719 B1 | 11/2001 | Bhullar et al. |
| 6,325,973 B1 | 12/2001 | Leland et al. |
| 6,379,969 B1 | 4/2002 | Mauze et al. |
| 6,387,290 B1 | 5/2002 | Brody et al. |
| 6,391,541 B1 | 5/2002 | Petersen et al. |
| 6,398,956 B1 | 6/2002 | Coville et al. |
| 6,403,384 B1 | 6/2002 | Lea |
| 6,406,672 B1 | 6/2002 | Buhllar et al. |
| 6,432,720 B2 | 8/2002 | Chow |
| 6,438,498 B1 | 8/2002 | Opalsky et al. |
| 6,440,725 B1 | 8/2002 | Pourahmadi et al. |
| 6,448,091 B1 | 9/2002 | Massey et al. |
| 6,451,225 B1 | 9/2002 | Leland et al. |
| 6,468,741 B1 | 10/2002 | Massey et al. |
| 6,475,372 B1 | 11/2002 | Ohara et al. |
| 6,479,233 B1 | 11/2002 | Bard et al. |
| 6,488,896 B2 | 12/2002 | Weigl et al. |
| 6,495,104 B1 | 12/2002 | Unno et al. |
| 6,517,777 B2 | 2/2003 | Liljestrand et al. |
| 6,524,513 B1 | 2/2003 | Pearl et al. |
| 6,524,865 B1 | 2/2003 | Martin et al. |
| 6,534,137 B1 | 3/2003 | Vadhar |
| 6,537,501 B1 | 3/2003 | Holl et al. |
| 6,554,788 B1 | 4/2003 | Hunley et al. |
| 6,559,096 B1 | 5/2003 | Smith et al. |
| 6,613,280 B2 | 9/2003 | Myrick et al. |
| 6,613,286 B2 | 9/2003 | Braunn, Sr. et al. |
| 6,613,583 B1 | 9/2003 | Richter et al. |
| 6,635,418 B2 | 10/2003 | Heroux et al. |
| 6,656,428 B1 | 12/2003 | Clark et al. |
| 6,664,104 B2 | 12/2003 | Pourahmadi et al. |
| 6,676,902 B2 | 1/2004 | Baugh et al. |
| 6,699,718 B1 | 3/2004 | Bruegger |
| 6,702,986 B1 | 3/2004 | Leland et al. |
| 6,740,240 B2 | 5/2004 | Coville et al. |
| 6,748,332 B2 | 6/2004 | Chen |
| 6,750,053 B1 | 6/2004 | Widrig Opalsky et al. |
| D494,589 S | 8/2004 | Liljestrand et al. |
| 6,776,965 B2 | 8/2004 | Wyzgol et al. |
| 6,783,736 B1 | 8/2004 | Taylor et al. |
| 6,794,877 B2 | 9/2004 | Blomberg et al. |
| 6,808,939 B2 | 10/2004 | Sigal et al. |
| D499,035 S | 11/2004 | Cook et al. |
| 6,818,185 B1 | 11/2004 | Petersen et al. |
| 6,824,663 B1 | 11/2004 | Boone |
| 6,831,733 B2 | 12/2004 | Pettersson et al. |
| 6,846,629 B2 | 1/2005 | Sigal et al. |
| 6,852,284 B1 | 2/2005 | Holl et al. |
| 6,852,502 B1 | 2/2005 | Martin |
| 6,861,259 B2 | 3/2005 | Columbus |
| 6,866,823 B2 | 3/2005 | Wardlaw |
| 6,869,570 B2 | 3/2005 | Wardlaw |
| 6,878,540 B2 | 4/2005 | Pourahmadi et al. |
| 6,880,384 B2 | 4/2005 | Hvidtfeldt et al. |
| 6,881,536 B1 | 4/2005 | Shah et al. |
| 6,881,541 B2 | 4/2005 | Petersen et al. |
| 6,881,589 B1 | 4/2005 | Leland et al. |
| 6,887,693 B2 | 5/2005 | McMillan et al. |
| 6,893,879 B2 | 5/2005 | Petersen et al. |
| 6,919,173 B2 | 7/2005 | Tsionsky et al. |
| 6,926,834 B2 | 8/2005 | Coville et al. |
| 6,929,953 B1 | 8/2005 | Wardlaw |
| 6,949,377 B2 | 9/2005 | Ho |
| 6,969,450 B2 | 11/2005 | Taniike et al. |
| 6,977,722 B2 | 12/2005 | Wohlstadter et al. |
| D515,220 S | 2/2006 | Miller et al. |
| 7,004,184 B2 | 2/2006 | Handique et al. |
| 7,008,796 B2 | 3/2006 | Wohlstadter et al. |
| 7,011,794 B2 | 3/2006 | Kagan et al. |
| 7,018,353 B2 | 3/2006 | Hunley et al. |
| 7,036,917 B2 | 5/2006 | Müller-Chorus et al. |
| 7,041,206 B2 | 5/2006 | Gephart et al. |
| 7,061,595 B2 | 6/2006 | Cabuz et al. |
| 7,111,503 B2 | 9/2006 | Brumboiu et al. |
| 7,115,421 B2 | 10/2006 | Grzeda et al. |
| 7,135,547 B2 | 11/2006 | Gengrinovitch |
| 7,205,116 B2 | 4/2007 | Salamone et al. |
| 7,235,213 B2 | 6/2007 | Mpock et al. |
| 7,238,246 B2 | 7/2007 | Peters et al. |
| 7,247,488 B2 | 7/2007 | Ghai et al. |
| 7,277,166 B2 | 10/2007 | Padmanabhan et al. |
| 7,282,179 B2 | 10/2007 | Iwaki et al. |
| 7,285,425 B2 | 10/2007 | Shareef et al. |
| 7,288,195 B2 | 10/2007 | Coville et al. |
| 7,299,081 B2 | 11/2007 | Mace et al. |
| 7,306,727 B2 | 12/2007 | Perreault |
| 7,314,711 B2 | 1/2008 | Richter et al. |
| 7,329,538 B2 | 2/2008 | Wainwright et al. |
| 7,335,339 B2 | 2/2008 | Brendtsson |
| 7,378,270 B2 | 5/2008 | Azarnia et al. |
| 7,384,409 B2 | 6/2008 | Fischer et al. |
| 7,399,637 B2 | 7/2008 | Wright et al. |
| 7,419,821 B2 | 9/2008 | Davis et al. |
| 7,422,903 B2 | 9/2008 | Conlon et al. |
| 7,422,905 B2 | 9/2008 | Clague et al. |
| 7,438,853 B2 | 10/2008 | Zen et al. |
| 7,439,017 B2 | 10/2008 | Heroux et al. |
| 7,439,069 B2 | 10/2008 | Nippoldt et al. |
| 7,471,394 B2 | 12/2008 | Padmanabhan et al. |
| 7,481,787 B2 | 1/2009 | Gable et al. |
| 7,485,153 B2 | 2/2009 | Padmanabhan et al. |
| 7,494,819 B2 | 2/2009 | Bahatt et al. |
| 7,497,997 B2 | 3/2009 | Glezer et al. |
| 7,521,247 B2 | 4/2009 | De Haan |
| 7,523,649 B2 | 4/2009 | Corey et al. |
| 7,547,384 B2 | 6/2009 | Keenan |
| 7,553,448 B2 | 6/2009 | Kumar et al. |
| 7,553,453 B2 | 6/2009 | Gu et al. |
| 7,569,346 B2 | 8/2009 | Petersen et al. |
| 7,569,393 B2 | 8/2009 | Sin |
| 7,595,169 B2 | 9/2009 | Swaim et al. |
| 7,604,777 B2 | 10/2009 | Columbus |
| 7,608,042 B2 | 10/2009 | Goldberger et al. |
| 7,630,063 B2 | 12/2009 | Padmanabhan et al. |
| 7,641,856 B2 | 1/2010 | Padmanabhan et al. |
| 7,666,355 B2 | 2/2010 | Alavie et al. |
| 7,682,511 B2 | 3/2010 | de Los Reyes et al. |
| 7,682,788 B2 | 3/2010 | Sigal et al. |
| 7,723,099 B2 | 5/2010 | Miller et al. |
| 7,736,901 B2 | 6/2010 | Opalsky et al. |
| 7,767,794 B2 | 8/2010 | Salamone et al. |
| 7,771,658 B2 | 8/2010 | Larsen |
| 7,776,583 B2 | 8/2010 | Billadeau et al. |
| 7,781,226 B2 | 8/2010 | McDevitt et al. |
| 7,816,124 B2 | 10/2010 | Samsoondar |
| 7,820,102 B2 | 10/2010 | Myrick et al. |
| 7,822,510 B2 | 10/2010 | Paik et al. |
| RE41,946 E | 11/2010 | Anderson et al. |
| 7,824,925 B2 | 11/2010 | Wohlstadter et al. |
| 7,833,746 B2 | 11/2010 | Berndtsson et al. |
| 7,838,631 B2 | 11/2010 | Yamashita et al. |
| 7,859,670 B2 | 12/2010 | Kim et al. |
| 7,887,750 B2 | 2/2011 | Blatt et al. |
| 7,888,125 B2 | 2/2011 | Gibbons et al. |
| 7,901,629 B2 | 3/2011 | Calatzis et al. |
| 7,911,617 B2 | 3/2011 | Padmanabhan et al. |
| 7,914,994 B2 | 3/2011 | Petersen et al. |
| 7,923,256 B2 | 4/2011 | Widrig Opalsky et al. |

(56) References Cited

U.S. PATENT DOCUMENTS

| | | |
|---|---|---|
| 7,928,718 B2 | 4/2011 | Larsen |
| 7,932,098 B2 | 4/2011 | Childers et al. |
| 7,939,021 B2 | 5/2011 | Smith et al. |
| 7,952,069 B2 | 5/2011 | Shiokawa et al. |
| 7,977,106 B2 | 7/2011 | Widrig Opalsky et al. |
| 7,978,329 B2 | 7/2011 | Padmanabhan et al. |
| 7,981,362 B2 | 7/2011 | Glezer et al. |
| 7,985,589 B2 | 7/2011 | Garner et al. |
| 8,003,060 B2 | 8/2011 | Cracauer et al. |
| 8,007,670 B2 | 8/2011 | Connors, Jr. |
| 8,008,034 B2 | 8/2011 | Gibbons et al. |
| 8,012,744 B2 | 9/2011 | Gibbons et al. |
| 8,012,745 B2 | 9/2011 | Glezer et al. |
| 8,017,382 B2 | 9/2011 | Davis et al. |
| 8,021,873 B2 | 9/2011 | Johnson et al. |
| 8,028,566 B2 | 10/2011 | Larsen |
| 8,034,296 B2 | 10/2011 | Cox et al. |
| 8,046,175 B2 | 10/2011 | Kuo et al. |
| 8,071,051 B2 | 12/2011 | Padmanabhan et al. |
| 8,101,404 B2 | 1/2012 | Samsoondar |
| 8,101,431 B2 | 1/2012 | McDevitt et al. |
| 8,105,783 B2 | 1/2012 | Handique |
| 8,105,849 B2 | 1/2012 | McDevitt et al. |
| 8,137,626 B2 | 3/2012 | Maltezos et al. |
| 8,236,555 B2 | 8/2012 | Stromgren et al. |
| 8,273,566 B2 | 9/2012 | Billadeau et al. |
| 8,343,526 B2 | 1/2013 | Billadeau et al. |
| 8,372,353 B2 * | 2/2013 | Lee et al. .................. 422/500 |
| 8,394,595 B2 | 3/2013 | Jung et al. |
| 8,394,608 B2 | 3/2013 | Ririe et al. |
| 8,481,901 B2 | 7/2013 | Bedingham et al. |
| 8,585,279 B2 | 11/2013 | Rida |
| 8,623,638 B2 | 1/2014 | Solomon |
| 8,747,779 B2 | 6/2014 | Sprague et al. |
| 8,772,017 B2 | 7/2014 | Battrell et al. |
| 8,778,665 B2 | 7/2014 | Gibbons et al. |
| 8,846,310 B2 | 9/2014 | Johnson et al. |
| 8,870,446 B2 | 10/2014 | Rida |
| 8,895,295 B2 | 11/2014 | Ririe et al. |
| 2002/0019060 A1 | 2/2002 | Petersen et al. |
| 2002/0098116 A1 | 7/2002 | Sugaya et al. |
| 2002/0143297 A1 | 10/2002 | Francavilla et al. |
| 2002/0155033 A1 | 10/2002 | Strand et al. |
| 2003/0029254 A1 | 2/2003 | Hvidtfeldt et al. |
| 2003/0035758 A1 | 2/2003 | Buechler et al. |
| 2003/0052054 A1 | 3/2003 | Pearl et al. |
| 2003/0073089 A1 | 4/2003 | Mauze et al. |
| 2003/0185707 A1 | 10/2003 | Iwaki et al. |
| 2003/0224523 A1 | 12/2003 | Thornberg et al. |
| 2004/0035792 A1 | 2/2004 | Rauch et al. |
| 2004/0086872 A1 | 5/2004 | Childers et al. |
| 2004/0096368 A1 | 5/2004 | Davis et al. |
| 2004/0176704 A1 | 9/2004 | Stevens et al. |
| 2004/0228765 A1 | 11/2004 | Witty et al. |
| 2004/0228766 A1 | 11/2004 | Witty et al. |
| 2004/0248284 A1 | 12/2004 | Van Beuningen |
| 2004/0259268 A1 | 12/2004 | Jacobs et al. |
| 2005/0014279 A1 | 1/2005 | Nguyen et al. |
| 2005/0042137 A1 | 2/2005 | Petersen et al. |
| 2005/0074900 A1 | 4/2005 | Morgan et al. |
| 2005/0181443 A1 | 8/2005 | Sun et al. |
| 2005/0220668 A1 | 10/2005 | Coville |
| 2005/0227370 A1 | 10/2005 | Ramel et al. |
| 2005/0245844 A1 | 11/2005 | Mace et al. |
| 2005/0250173 A1 | 11/2005 | Davis et al. |
| 2006/0094028 A1 | 5/2006 | Danna et al. |
| 2006/0165558 A1 | 7/2006 | Witty et al. |
| 2006/0177347 A1 | 8/2006 | Larsen et al. |
| 2006/0218010 A1 | 9/2006 | Michon et al. |
| 2006/0228259 A1 | 10/2006 | Samsoondar |
| 2006/0257854 A1 | 11/2006 | McDevitt et al. |
| 2006/0257941 A1 | 11/2006 | McDevitt et al. |
| 2006/0257991 A1 | 11/2006 | McDevitt et al. |
| 2006/0263818 A1 | 11/2006 | Scherer et al. |
| 2006/0275841 A1 | 12/2006 | Blankfard et al. |
| 2007/0003434 A1 | 1/2007 | Padmanabhan et al. |
| 2007/0009386 A1 | 1/2007 | Padmanabhan et al. |
| 2007/0031283 A1 | 2/2007 | Davis et al. |
| 2007/0036026 A1 | 2/2007 | Laibinis et al. |
| 2007/0116600 A1 | 5/2007 | Kochar et al. |
| 2007/0166195 A1 | 7/2007 | Padmanabhan et al. |
| 2007/0166196 A1 | 7/2007 | Bardell et al. |
| 2007/0166725 A1 | 7/2007 | McBride et al. |
| 2007/0172388 A1 | 7/2007 | Padmanabhan et al. |
| 2007/0178514 A1 | 8/2007 | Van Beuningen |
| 2007/0178521 A1 | 8/2007 | Sakaino et al. |
| 2007/0248497 A1 | 10/2007 | Robillot |
| 2007/0292941 A1 | 12/2007 | Handique et al. |
| 2008/0021296 A1 | 1/2008 | Creaven |
| 2008/0025872 A1 | 1/2008 | Dykes et al. |
| 2008/0057572 A1 | 3/2008 | Petersen et al. |
| 2008/0131322 A1 | 6/2008 | Kheiri et al. |
| 2008/0149840 A1 | 6/2008 | Handique et al. |
| 2008/0153078 A1 | 6/2008 | Braman et al. |
| 2008/0188732 A1 | 8/2008 | Mace et al. |
| 2008/0227219 A1 | 9/2008 | Gamez |
| 2008/0311002 A1 | 12/2008 | Kirby et al. |
| 2009/0018411 A1 | 1/2009 | Mace et al. |
| 2009/0047713 A1 | 2/2009 | Handique |
| 2009/0065357 A1 | 3/2009 | Glezer et al. |
| 2009/0081078 A1 | 3/2009 | Caramuta |
| 2009/0098541 A1 | 4/2009 | Southern et al. |
| 2009/0130658 A1 | 5/2009 | Barlag et al. |
| 2009/0130719 A1 | 5/2009 | Handique |
| 2009/0148882 A1 | 6/2009 | Goldstein |
| 2009/0151792 A1 | 6/2009 | Noda |
| 2009/0181864 A1 | 7/2009 | Nguyen et al. |
| 2009/0215072 A1 | 8/2009 | McDevitt et al. |
| 2009/0221059 A1 | 9/2009 | Williams et al. |
| 2009/0246076 A1 | 10/2009 | Kumar et al. |
| 2009/0253130 A1 | 10/2009 | Yoo |
| 2009/0311736 A1 | 12/2009 | Ciotti et al. |
| 2009/0325276 A1 | 12/2009 | Battrell et al. |
| 2010/0029011 A1 | 2/2010 | Sin |
| 2010/0081144 A1 | 4/2010 | Holmes et al. |
| 2010/0112723 A1 | 5/2010 | Battrell et al. |
| 2010/0117666 A1 | 5/2010 | Wada et al. |
| 2010/0158756 A1 | 6/2010 | Taylor et al. |
| 2010/0159556 A1 | 6/2010 | Rida |
| 2010/0173394 A1 | 7/2010 | Colston, Jr. et al. |
| 2010/0197522 A1 | 8/2010 | Liu et al. |
| 2010/0203521 A1 | 8/2010 | Klapperich et al. |
| 2010/0203550 A1 | 8/2010 | Miller et al. |
| 2010/0227412 A1 | 9/2010 | Cerda |
| 2010/0240022 A1 | 9/2010 | McNeely |
| 2010/0261292 A1 | 10/2010 | Glezer et al. |
| 2010/0262304 A1 | 10/2010 | Gonnella et al. |
| 2010/0282609 A1 | 11/2010 | Pollack et al. |
| 2010/0285578 A1 | 11/2010 | Selden et al. |
| 2010/0290952 A1 | 11/2010 | Koike et al. |
| 2010/0291588 A1 | 11/2010 | McDevitt et al. |
| 2010/0303722 A1 | 12/2010 | Jin et al. |
| 2011/0008908 A1 | 1/2011 | Biesbrouck |
| 2011/0016691 A1 | 1/2011 | Alden et al. |
| 2011/0039298 A1 | 2/2011 | Berndtsson et al. |
| 2011/0067489 A1 | 3/2011 | Haberstroh et al. |
| 2011/0091357 A1 | 4/2011 | Blatt et al. |
| 2011/0100101 A1 | 5/2011 | Zenhausern et al. |
| 2011/0143378 A1 | 6/2011 | Putnam |
| 2011/0171754 A1 | 7/2011 | Redmond et al. |
| 2011/0192218 A1 | 8/2011 | Miyamura et al. |
| 2011/0192219 A1 | 8/2011 | Miyamura et al. |
| 2011/0194977 A1 | 8/2011 | Miyamura et al. |
| 2011/0195490 A1 | 8/2011 | Kang et al. |
| 2011/0195495 A1 | 8/2011 | Selden et al. |
| 2011/0201909 A1 | 8/2011 | Emery et al. |
| 2011/0203924 A1 | 8/2011 | Wohlstadter et al. |
| 2011/0259091 A1 | 10/2011 | Laubscher et al. |
| 2011/0269159 A1 | 11/2011 | Campbell et al. |
| 2011/0269222 A1 | 11/2011 | Miller et al. |
| 2011/0290669 A1 | 12/2011 | Davis et al. |
| 2011/0294224 A1 | 12/2011 | Liu |
| 2011/0312553 A1 | 12/2011 | Silverbrook et al. |
| 2011/0312661 A1 | 12/2011 | Silverbrook et al. |

(56) References Cited

U.S. PATENT DOCUMENTS

| | | |
|---|---|---|
| 2011/0312742 A1 | 12/2011 | Silverbrook et al. |
| 2011/0318774 A1 | 12/2011 | Larsen |
| 2012/0003730 A1 | 1/2012 | Padmanabhan et al. |
| 2012/0009667 A1 | 1/2012 | Peterson et al. |
| 2012/0034624 A1 | 2/2012 | Miller et al. |
| 2012/0034645 A1 | 2/2012 | Billadeau et al. |
| 2012/0043202 A1 | 2/2012 | Miyamura et al. |
| 2012/0045375 A1 | 2/2012 | Miyamura et al. |
| 2012/0051972 A1 | 3/2012 | Joseph |
| 2012/0053335 A1 | 3/2012 | Liu et al. |
| 2012/0115213 A1 | 5/2012 | Hofstadler et al. |
| 2012/0141337 A1 | 6/2012 | Maltezos et al. |
| 2012/0177537 A1 | 7/2012 | Aota et al. |
| 2012/0190128 A1 | 7/2012 | Nikbakht et al. |
| 2012/0252138 A1 | 10/2012 | Sasso, Jr. et al. |
| 2013/0137172 A1 | 5/2013 | Ririe et al. |
| 2014/0017709 A1 | 1/2014 | Lowe et al. |
| 2014/0186935 A1 | 7/2014 | Yoo |
| 2014/0329301 A1 | 11/2014 | Handique |

FOREIGN PATENT DOCUMENTS

| | | |
|---|---|---|
| EP | 2007905 B1 | 12/2008 |
| EP | 2281631 B1 | 2/2011 |
| EP | 2419217 B1 | 2/2012 |
| GB | 2112293 | 7/1983 |
| JP | 2010-237050 | 10/2010 |
| WO | 8706706 | 11/1987 |
| WO | 9005302 | 5/1990 |
| WO | 9419683 | 9/1994 |
| WO | 9419684 | 9/1994 |
| WO | 9508644 | 3/1995 |
| WO | 9621154 | 7/1996 |
| WO | 9635697 | 11/1996 |
| WO | 9635812 | 11/1996 |
| WO | 9641177 | 12/1996 |
| WO | 9915694 | 4/1999 |
| WO | 2005095954 A1 | 10/2005 |
| WO | 2007002579 A2 | 1/2007 |
| WO | 2007005626 | 1/2007 |
| WO | 2011027092 A1 | 3/2011 |
| WO | 2011113569 | 9/2011 |
| WO | 2012024543 A1 | 2/2012 |
| WO | 2012058632 A1 | 5/2012 |
| WO | 2012136695 A1 | 10/2012 |
| WO | 2013082273 A1 | 6/2013 |
| WO | 2013136115 A1 | 9/2013 |
| WO | 2013173524 A2 | 11/2013 |
| WO | 2013173525 A1 | 11/2013 |
| WO | 2014043388 A1 | 3/2014 |

OTHER PUBLICATIONS

Bertino, et al., "5-Fluorouracil Drug Management: Pharmacokinetics and Pharmacogenomics Workshop Meeting Summary; Orlando, Florida; Jan. 2007", Clinical Colorectal Cancer, vol. 6(6):407-422 (2007).
Bertucci, et al., "The Binding of 5-fluorouracil to Native and Modified Human Serum Albumin: UV, CD, and 1H and 19F NMR Investigation", Journal of Pharmaceutical and Biomedical Analysis, vol. 13:1087-1093 (1995).
Beumer, et al., "A Rapid Nanoparticle Immunoassay to Quantitate 5-Fluorouracil (5-FU) in Plasma", ASCO GI 2008 Meeting (Poster).
Crowley, et al., "Isolation of Plasma from Whole Blood Using Planar Microfilters for Lab-on-a-Chip Applications", Lab Chip, vol. 5(9):922-929 (2005).
Jaffrin, M.Y. (1995). Biological Flows. M.Y. Jaffrin and Colin Caro (Eds.). Plenum Press, New York, pp. 199-226.
Joseph, et al., "Evaluation of Alternatives to Warfarin as Probes for Sudlow Site I of Human Serum Albumin Characterization by High-Performance Affinity Chromatography", J. Chromatogr. A., vol. 1216(16):3492-3500 (2009).
Lukas, et al., "Binding of Digitoxin and Some Related Cardenolides to Human Plasma Proteins", The Journal of Clinical Investigation, vol. 48:1041-1053 (1969).
Madsen, et al., "Cooperative Interaction of Warfarin and Phenylbutazone with Human Serum Albumin", Biochemical Pharmacology, vol. 30(11):1169-1173 (1981).
Means, et al. (1982). Modification of Proteins: Food, Nutritional, and Pharmacological Aspects. Robert E. Feeny and John R. Whitaker (Eds.). American Chemical Society. pp. 325-346.
Olympus UK Ltd—Diagnostics Laboratory News Directory, http://www.labnewsdirectory.co.uk/company/Olympus-UK-Ltd-Diagnostics/2232, (Oct. 1, 2009).
Peters, T., Jr., "Serum Albumin", Adv. Protein Chem., vol. 37:161-246 (1985).
Peyrin, et al., "Characterization of Solute Binding at Human Serum Albumin Site II and its Geometry Using a Biochromatographic Approach", Biophysical Journal, vol. 77:1206-1212 (1999).
Saif, et al. "Pharmacokinetically Guided Doe Adjustment of 5-Fluorouracil: A Rational Approach to Improving Therapeutic Outcomes", J. Natl. Cancer Inst., vol. 101:1543-1552 (2009).
Salamone, et al., "Novel Monoclonal Antibodies for Measuring 5-Fluorouracil Concentrations in Biological Fluids", Journal of Clinical Oncology, 2006 ASCO Annual Meeting Proceedings (Post-Meeting Edition); vol. 24(18S):2055 (2006).
Salamone, et al., "A Multi-Center Evaluation of a Rapid Immunoassay to Quantitate 5-Fluorouracil in Plasma", 2008 HOPA Conference—Anaheim, California (Poster).
Sulkowska, et al., "Competitive Binding of Phenylbutazone and Colchicine to Serum Albumin in Multidrug Therapy: A Spectroscopic Study", Journal of Molecular Structure, vol. 881:97-106 (2008).
Vandelinder, V. and A. Groisman, "Separation of Plasma from Whole Human Blood in a Continuous Cross-Flow in a Molded Microfluidic Device", Anal. Chem., vol. 78:3765-3771 (2006).
Villamor, J. and A. Zatón, "Data Plotting of Warfarin Binding to Human Serum Albumin", J. Biochem. Biophys. Methods, vol. 48:33-41 (2001).
Vos, et al., "Use of the Enzyme-Linked Immunosorbent Assay (ELISA) in Immunotoxicity Testing", Environmental Health Perspectives, vol. 43:115-121 (1982).
Yamashita, et al., "5-Fluorouracil Derivatives with Serum Protein Binding Potencies", Chem. Pharm. Bull., vol. 37 (10):2861-2863 (1989).
Yamashita, et al., "Possible Role of Serum Protein Binding to Improve Drug Disposition", International Journal of Pharmaceutics, vol. 108:241-247 (1994).
Zsila, et al., "Evaluation of Drug-Human Serum Albumin Binding Interactions with Support Vector Machine Aided Online Automated Docking", Bioinformatics, vol. 27(13):1806-1813 (2011).
The International Search Report and the Written Opinion from International PCT Application No. PCT/US2013/041252.
The International Search Report and the Written Opinion from International PCT Application No. PCT/US2013/041255.
The International Search Report and the Written Opinion from International PCT Application No. PCT/US2012/067041.
Restriction Requirement, dated Jun. 27, 2014, from co-pending U.S. Appl. No. 13/844,450.
Response to Jun. 27, 2014 Restriction Requirement, from co-pending U.S. Appl. No. 13/844,450.
Notice of Allowance and Fees Due, dated Oct. 22, 2014, from co-pending U.S. Appl. No. 13/844,450.
Notice of Allowance and Fees Due, dated Jan. 5, 2015, from co-pending U.S. Appl. No. 13/844,450.

* cited by examiner

DIAGNOSTIC SYSTEMS AND CARTRIDGES

CROSS-REFERENCE TO RELATED APPLICATIONS

This application claims priority to U.S. Provisional Application No. 61/647,272, filed May 15, 2012, and International PCT Application No. PCT/US2012/067041, filed on Nov. 29, 2012, each of which is herein incorporated by reference in its entirety.

FIELD

The present disclosure relates to a clinical diagnostic system, including a clinical diagnostic instrument with a disposable cartridge useful for completing diagnostic analysis in a fast and efficient manner in a clinical setting. In particular, a disposable cartridge is disclosed that is suitable for use with a clinical or diagnostic point-of-care device and capable of performing diagnostic and analytical functions including filtering samples such as plasma from whole blood and running assays and collecting measurements of analytes or biomarkers.

BACKGROUND

Clinical laboratory testing requires devices and tests with high accuracy and precision. Containing costs for lab tests is also important. Some clinical lab tests are conducted in high volume because of the large number of patients undergoing tests. There are drawbacks associated with present procedures that require sequential and additional steps and transfers of multiple reagents to produce the assay. Each additional step for a detection assay increases the degree of difficulty for execution and may even increase chances of contamination or error by the operator and is prone to misuse, thereby, resulting in a higher margin for error. Thus, it is desirable to have a clinical diagnostic device that can reduce the undesirable processing steps of transferring samples to labs and instead complete a diagnostic test in a physician's office or at a patient's bedside. Such a device would inevitably reduce processing costs and cut down on opportunity for error and contamination.

SUMMARY

The disclosure relates generally to a clinical diagnostic system, including a clinical diagnostic instrument with a disposable cartridge useful for completing diagnostic analysis in a fast and efficient manner in a clinical setting.

In one embodiment, the disclosure relates to a multi-layer seal, comprising a barrier layer to reduce (or prevent) evaporation of liquids stored in a disposable cartridge; and a laminating element, wherein the laminating element joins the barrier layer to the disposable cartridge to seal the liquids and/or dry reagents within the disposable cartridge.

In some embodiments, the disclosure relates generally to a multi-layer seal, wherein the laminating element is made from a material chosen from a heat seal coating, a pressure sensitive adhesive (PSA), a pressure sensitive adhesive tape, a thermal adhesive, a transfer tape, a transfer adhesive, a double-sided tape, a tie layer, and an adhesive film.

In some embodiments, the disclosure relates generally to a multi-layer seal, wherein the laminating element is made from a pressure sensitive adhesive (PSA).

In some embodiments, the disclosure relates generally to a multi-layer seal, wherein the barrier layer is made from a material with low moisture vapor transmission rate.

In some embodiments, the disclosure relates generally to a multi-layer seal, wherein the barrier layer is made from a material with a moisture vapor transmission rate that is at least two times (2×) lower than a material used to form the disposable cartridge.

In some embodiments, the disclosure relates generally to a multi-layer seal, wherein the barrier layer is made from a material chosen from aluminum foil, aluminum alloy foils, metal alloy foils, high MVTR films, high barrier films, COC films, films made of fluorinated-chlorinated resins, duplex films, and triplex films.

In some embodiments, the disclosure relates generally to a multi-layer seal, wherein the barrier layer is made from aluminum foil.

In some embodiments, the disclosure relates generally to a multi-layer seal, wherein the barrier layer is puncturable.

In some embodiments, the disclosure relates generally to a multi-layer seal, wherein the multi-layer seal is a lid that seals at least one reagent handling station.

In another embodiment, the disclosure provides a multi-layer film structure, comprising a septum layer for establishing a fluidic connection between a disposable cartridge and at least one probe of a diagnostic instrument, wherein the multi-layer film structure is joined to the disposable cartridge; a support layer for reducing stretch of the septum layer during piercing and withdrawal of the at least one probe; and at least one laminating element that joins the septum layer to the support layer.

In some embodiments, the disclosure relates generally to a multi-layer film structure, wherein the septum layer is re-sealing and the support layer is substantially rigid.

In some embodiments, the disclosure relates generally to a multi-layer film structure, wherein the septum layer has at least one of the properties of pierceable, reversibly stretchable, elastic, reversibly compressible, self-sealing, prevents fluid and gas exchange, and seals against a probe.

In some embodiments, the disclosure relates generally to a multi-layer film structure, wherein the septum layer has all of the properties of pierceable, reversibly stretchable, elastic, reversibly compressible, self-sealing, prevents fluid and gas exchange, and seals against a probe.

In some embodiments, the disclosure relates generally to a multi-layer film structure, wherein the multi-layer film structure has at least one probe-addressable location.

In some embodiments, the disclosure relates generally to a multi-layer film structure, wherein the multi-layer film structure has a plurality of probe entry sites addressable by the probe at least once during operation.

In some embodiments, the disclosure relates generally to a multi-layer film structure, wherein the multi-layer film structure has a plurality of probe entry sites that are addressable more than once or re-usable.

In some embodiments, the disclosure relates generally to a multi-layer film structure, wherein the multi-layer film structure has at least one probe entry site addressable by the probe such that the probe will not pierce the septum layer (and such that a vent is formed at the probe entry site upon withdrawal of the probe).

In some embodiments, the disclosure relates generally to a multi-layer film structure, wherein the multi-layer film structure has at least one probe entry site addressable by the probe which is puncturable.

In some embodiments, the disclosure relates generally to a multi-layer film structure, wherein the septum layer is made from a material chosen from synthetic rubber, silicone rubber, butyl rubber, natural rubber, elastomers, fluoroelastomers, copolymers of hexafluoropropylene, copolymers of vinylidene fluoride, terpolymers of tetrafluoroethylene, terpolymers of vinylidene fluoride, terpolymers of hexafluoropropylene, and perfluoromethylvinylether polymers.

In some embodiments, the disclosure relates generally to a multi-layer film structure, wherein the septum layer is made from silicone rubber.

In some embodiments, the disclosure relates generally to a multi-layer film structure, wherein the support layer has at least one of the properties of reduces stretch and tension of septum layer, adds rigidity to overall multi-layer film structure, adds stiffness to overall multi-layer film structure, re-enforces overall multi-layer film structure, has high flexural modulus, reduces elongation of the septum layer, and is puncturable.

In some embodiments, the disclosure relates generally to a multi-layer film structure, wherein the support layer has all of the properties of reduces stretch and tension of septum layer, adds rigidity to overall multi-layer film structure, adds stiffness to overall multi-layer film structure, re-enforces overall multi-layer film structure, reduces elongation of the septum layer, and is puncturable.

In some embodiments, the disclosure relates generally to a multi-layer film structure, wherein the support layer is made from a material chosen from metals, such as, aluminum, aluminum alloys, metal alloys, foils, rigid films, plastics sheeting, polytetrafluoroethylene, polyvinyl chloride, polyester, and polymers thereof.

In some embodiments, the disclosure relates generally to a multi-layer film structure, wherein the support layer is made from aluminum foil.

In some embodiments, the disclosure relates generally to a multi-layer film structure, wherein the support layer has a thickness of less than or equal to 7 mils, less than or equal to 6 mils or less than or equal to 5 mils.

In some embodiments, the disclosure relates generally to a multi-layer film structure, wherein the support layer has a thickness of less than or equal to 7 mils, less than or equal to 6 mils, less than or equal to 5 mils, less than or equal to 4 mils, less than or equal to 3 mils, less than or equal to 2 mils, less than or equal to 1 mils, or less than or equal to 0.5 mils.

In some embodiments, the disclosure relates generally to a multi-layer film structure, wherein the support layer adds stiffness to the multi-layer film structure facilitating the piercing of the septum layer by a probe.

In some embodiments, the disclosure relates generally to a multi-layer film structure, wherein the support layer adds stiffness to the multi-layer film structure reducing stretching of the septum layer during a probe entry or withdrawal.

In some embodiments, the disclosure relates generally to a multi-layer film structure, wherein the laminating element is made from a material chosen from a pressure sensitive adhesive (PSA), a thermal adhesive, a transfer tape, a transfer adhesive, a double sided tape, a tie layer, and an adhesive film.

In some embodiments, the disclosure relates generally to a multi-layer film structure, wherein the laminating element is made from a pressure sensitive adhesive (PSA).

In some embodiments, the disclosure relates generally to a multi-layer film structure, wherein the layers of the multi-layer film are die-cuttable.

In some embodiments, the disclosure relates generally to a multi-layer film structure, wherein the multi-layer film structure is a component of a closed fluidic pathway.

In other embodiments, the disclosure relates generally to a multi-layer film structure, comprising a septum layer, a first laminating element, and a top seal, wherein the first laminating element joins the septum layer with the top seal, and the top seal is comprised of a support layer and a second laminating element, and wherein the second laminating element joins the support with the cartridge.

In other embodiments, the disclosure relates generally to an apparatus for mounting a blood collection tube to a cartridge, the apparatus comprising a framework comprised of at least one structural member of a cartridge; at least one needle to establish a fluidic connection between the cartridge and the blood collection tube when the at least one needle pierces a septum of the blood collection tube, wherein the framework guides the blood collection tube into position such that the blood collection tube is at an angle ranging from about less than 90° to about 0° from the horizontal, wherein the dead volume in the blood collection tube is less than 25% of an initial fill volume.

In some embodiments, the disclosure relates generally to an apparatus for mounting a blood collection tube to a cartridge, wherein the dead volume in the blood collection tube is less than 20% of an initial fill volume, less than 10% of an initial fill volume, or less than 5% of an initial fill volume.

In some embodiments, the disclosure relates generally to an apparatus for mounting a blood collection tube to a cartridge, wherein the blood collection tube is at an angle ranging from less than 90° to about 45°, from about 45° to about 0°, from about 30° to about 0°, from about 20° to about 0°, from about 10° to about 0°, from about 7° to about 0°, from about 45° to about 20°, from about 45° to about 15°, from about 45° to about 10°, from about 35° to about 15°, from about 35° to about 10°, from about 35° to about 5°, from about 25° to about 15°, from about 25° to about 10°, from about 25° to about 5°, from about 15° to about 10°, from about 15° to about 5°, from about 10° to about 5°, from about 10° to about 7°, or from about 7° to about 5°, or from about 5° to about 0° from the horizontal.

In some embodiments, the disclosure relates generally to an apparatus for mounting a blood collection tube to a cartridge, wherein the blood collection tube is at an angle of about 45°, about 30°, about 25°, about 20°, about 15°, about 10°, about 8°, about 7°, about 6°, about 5°, about 0° from the horizontal.

In some embodiments, the disclosure relates generally to an apparatus for mounting a blood collection tube to a cartridge, wherein the blood collection tube is at an angle of about 7° from the horizontal.

In some embodiments, the disclosure relates generally to an apparatus for mounting a blood collection tube to a cartridge, wherein the framework is comprised solely of a cartridge body.

In some embodiments, the disclosure relates generally to an apparatus for mounting a blood collection tube to a cartridge, wherein the framework is comprised solely of structural members other than a cartridge body.

In some embodiments, the disclosure relates generally to an apparatus for mounting a blood collection tube to a cartridge, wherein the framework is comprised of a combination of a cartridge body and at least one other structural member.

In some embodiments, the disclosure relates generally to an apparatus for mounting a blood collection tube to a cartridge, wherein the framework provides a mechanism to prevent removal of the blood collection tube after the septum of the blood collection tube has been pierced.

In some embodiments, the disclosure relates generally to an apparatus for mounting a blood collection tube to a cartridge, wherein the mechanism to prevent removal of the blood collection tube is a tang.

In some embodiments, the disclosure relates generally to an apparatus for mounting a blood collection tube to a cartridge, the at least one needle comprising a first needle for introducing gas into the blood collection tube and a second needle for extracting blood from the blood collection tube, wherein the introduced gas facilitates blood extraction.

In some embodiments, the disclosure relates generally to an apparatus for mounting a blood collection tube to a cartridge, wherein a lubricant is applied to the at least one needle to further facilitate piercing of the septum of the blood collection tube.

In some embodiments, the disclosure relates generally to an apparatus for mounting a blood collection tube to a cartridge, wherein the at least one needle is mounted in a recess within the framework.

In some embodiments, the disclosure relates generally to an apparatus for mounting a blood collection tube to a cartridge, wherein the at least one needle is mounted in a recess within the framework and secured with an adhesive into the recess.

In some embodiments, the disclosure relates generally to an apparatus for mounting a blood collection tube to a cartridge, wherein after a fluidic connection is established with the cartridge, the blood is filtered by a blood filtration module within the cartridge to separate plasma out of the blood.

In some embodiments, the disclosure relates generally to an apparatus for mounting a blood collection tube to a cartridge, wherein the apparatus is part of a closed fluidic pathway.

In some embodiments, the disclosure relates generally to an apparatus for mounting a blood collection tube to a cartridge, wherein the apparatus is in fluidic communication with a blood filtration module and a blood collection tube.

In some embodiments, the disclosure relates generally to an apparatus for mounting a blood collection tube to a cartridge, wherein the apparatus is in fluidic communication with a probe.

In some embodiments, the disclosure relates generally to an apparatus for mounting a blood collection tube to a cartridge, wherein the apparatus is in fluidic communication with a probe pierced through a septum seal.

In some embodiments, the disclosure relates generally to an apparatus for mounting a blood collection tube to a cartridge, wherein the apparatus is in fluidic communication with a probe pierced through a septum seal and a pump.

In some embodiments, the disclosure relates generally to an apparatus for mounting a blood collection tube to a cartridge, wherein the apparatus includes a tube cover.

In some embodiments, the disclosure relates generally to an apparatus for mounting a blood collection tube to a cartridge, wherein the apparatus includes a tube cover and cartridge.

In further embodiments, the disclosure relates generally to a method of extracting blood from a blood collection tube, comprising positioning the blood collection tube containing a sample on a cartridge, the cartridge having a framework comprised of at least one structural member of the cartridge; at least two needles to establish a fluidic connection between the cartridge and blood collection tube when the at least two needles pierce a septum of the blood collection tube, wherein the framework guides the blood collection tube into position such that the blood collection tube is at an angle ranging from about less than 90° to about 0° from the horizontal; and introducing gas into a first of the at least two needles causing a displacement of the blood by the gas wherein the displaced blood flows from the blood collection tube to a second of the at least two needles.

In some embodiments, the disclosure relates generally to a method of extracting blood from a blood collection tube, wherein the second needle is in fluidic communication with a blood filtration module.

In some embodiments, the disclosure relates generally to a method of extracting blood from a blood collection tube, wherein the second needle is in fluidic communication with a blood filtration module, a fluidic channel, and a plasma cache, wherein an optical sensor detects an air liquid boundary when the plasma cache is filled.

In yet a further embodiment, the disclosure relates generally to a cartridge for use in a diagnostic system, comprising a body and a cover, wherein the body and the cover mate together; a blood collection tube mount to secure a blood collection tube to the cartridge, wherein the blood collection tube mount has at least one needle to engage the blood collection tube and form a fluidic connection between the cartridge and the blood collection tube; a blood collection tube; a blood filtration module in fluidic communication with the blood collection tube mount; and a plasma cache.

In yet a further embodiment, the disclosure relates generally to a cartridge for use in a diagnostic system, comprising: a body and a cover, wherein the body and the cover mate together; at least one reagent handling station formed from the body; a multi-layer fluidic seal to establish a liquid and air-tight seal of the at least one reagent handling station and to establish a fluidic connection with at least one probe of a diagnostic instrument in the diagnostic system; at least one fluidic channel formed from the body and sealed by a bottom seal, wherein the bottom seal defines in part the volume of the fluidic channels.

In some embodiments, the disclosure relates generally to a cartridge for use in a diagnostic system, wherein the at least one reagent handling station comprises a pocket formed in the floor of each reagent handling station.

In some embodiments, the disclosure relates generally to a cartridge for use in a diagnostic system, wherein the pocket reduces dead volume within the at least one reagent handling station when the at least one probe engages the multi-layer seal to contact a fluid contained therein and allows the probe to contact fluid within the pocket.

In some embodiments, the disclosure relates generally to a cartridge for use in a diagnostic system, wherein the at least one reagent handling station has a low moisture vapor transmission rate.

In some embodiments, the disclosure relates generally to a cartridge for use in a diagnostic system, wherein there are at least two reagent handling stations, and wherein one of the at least two reagent handling stations contains a pump storage liquid.

In some embodiments, the disclosure relates generally to a cartridge for use in a diagnostic system, wherein there are at least two reagent handling stations, and wherein one of the at least two reagent handling stations is initially empty and is for receiving waste.

In some embodiments, the disclosure relates generally to a cartridge for use in a diagnostic system, wherein there are at least two reagent handling stations, and wherein all reagent handling stations are initially filled with liquid except one, which is initially empty and is for receiving waste.

In some embodiments, the disclosure relates generally to a cartridge for use in a diagnostic system, wherein there are at least two reagent handling stations, and wherein all reagent handling stations are initially filled with ECL read buffer except one, which is initially empty and is for receiving waste.

In some embodiments, the disclosure relates generally to a cartridge for use in a diagnostic system, wherein the at least one reagent handling station is part of a closed fluidic pathway.

In some embodiments, the disclosure relates generally to a cartridge for use in a diagnostic system, wherein the at least one reagent handling station is part of a closed fluidic pathway, and wherein liquid emptied from a filled reagent handling station fills an empty reagent handling station using a closed fluidic system.

In still other embodiments, the disclosure relates generally to a cartridge for use in a diagnostic system, comprising a body and a cover, wherein the body and the cover mate together; a blood collection tube mount to secure a blood collection tube to the cartridge, wherein the blood collection tube mount has at least one needle to engage the blood collection tube and form a fluidic connection between the cartridge and the blood collection tube; at least one reagent handling station formed from the body; a multi-layer fluidic seal to establish a liquid and air-tight seal of the at least one reagent handling station and to establish a fluidic connection with at least one probe of a diagnostic instrument in the diagnostic system; at least one fluidic channel formed from the body and sealed by a bottom seal, wherein the bottom seal defines in part the volume of the fluidic channels.

In still other embodiments, the disclosure relates generally to a cartridge for use in a diagnostic system, comprising a body and a cover, wherein the body and the cover mate together; a blood collection tube mount to secure a blood collection tube to the cartridge, wherein the blood collection tube mount has at least one needle to engage the blood collection tube and form a fluidic connection between the cartridge and the blood collection tube; a blood collection tube; a blood filtration module in fluidic communication with the blood collection tube mount; and a plasma cache; at least one reagent handling station formed from the body; a multi-layer fluidic seal to establish a liquid and air-tight seal of the at least one reagent handling station and to establish a fluidic connection with at least one probe of a diagnostic instrument in the diagnostic system; at least one fluidic channel formed from the body and sealed by a bottom seal, wherein the bottom seal defines in part the volume of the fluidic channels.

In still another embodiment, the present disclosure relates generally to a method of metering a sample within a cartridge, comprising drawing a first volume of plasma from a sample reservoir into a primary channel of the cartridge, wherein the primary channel is filled up to a predetermined volume detected by an optical sensor of a diagnostic instrument; emptying any remaining plasma from the sample reservoir not used to fill the primary channel into a secondary channel using an optical sensor of the diagnostic instrument to detect an air liquid boundary; drawing a second volume of plasma from the primary channel into at least one receiver channel, wherein the second volume is a predetermined volume, wherein the process is repeated until each receiver channel holds the second volume of plasma, and wherein each of the steps performed are independent of pump accuracy.

In some embodiments, the present disclosure relates generally to a method of metering a sample within a cartridge, wherein the sample reservoir has a volume which is greater than or equal to the sum of the first and second volumes.

In some embodiments, the present disclosure relates generally to a method of metering a sample within a cartridge, wherein the sample reservoir has a volume ranging from about 125 µL to about 135 µL, about 135 µL to about 150 µL, about 150 µL to about 175 µL, and about 175 µL to about 200 µL.

In some embodiments, the present disclosure relates generally to a method of metering a sample within a cartridge, wherein the sample reservoir has a volume of about 200 µL.

In some embodiments, the present disclosure relates generally to a method of metering a sample within a cartridge, wherein the primary channel has a volume less than the sample reservoir.

In some embodiments, the present disclosure relates generally to a method of metering a sample within a cartridge, wherein the primary channel has a volume ranging from about 125 µL to about 135 µL, about 135 µL to about 150 µL, about 150 µL to about 175 µL, and about 175 µL to less than about 200 µL In some embodiments, the present disclosure relates generally to a method of metering a sample within a cartridge, wherein the primary channel has a volume of about 150 µL.

In some embodiments, the present disclosure relates generally to a method of metering a sample within a cartridge, wherein the secondary channel has a volume less than the sample reservoir.

In some embodiments, the present disclosure relates generally to a method of metering a sample within a cartridge, wherein the secondary channel has a volume ranging from about 125 µL to about 135 µL, about 135 µL to about 150 µL, about 150 µL to about 175 µL, and about 175 µL to less than about 200 µL.

In some embodiments, the present disclosure relates generally to a method of metering a sample within a cartridge, wherein the secondary channel has a volume of about 150 µL.

In some embodiments, the present disclosure relates generally to a method of metering a sample within a cartridge, wherein the secondary channel has a volume greater than the difference in volume between the sample reservoir and the primary channel volumes.

In some embodiments, the present disclosure relates generally to a method of metering a sample within a cartridge, wherein each of the primary channel, the secondary channel and the receiver channels is fluidically connected to a pump of the diagnostic instrument using a probe pierced through a septum seal.

In still further embodiments, the present disclosure relates generally to a method of mixing a sample within a cartridge of a diagnostic system, comprising drawing the sample within a fluidic channel until an optical sensor detects an air liquid transition of the sample, wherein the fluidic channel is fluidically connected to a pump; further drawing the sample into a well containing an assay reagent, and rehydrating a lyophilized reagent with the sample, wherein the well is fluidically connected to the pump and there is at least one difference in the cross sectional area between the fluidic channel and the well; and mixing until the sample with the assay reagent is substantially homogenous by back and forth pump motions, and causing the sample to flow through the differences in the cross sectional area between the fluidic channel and the well.

In some embodiments, the present disclosure relates generally to a method of mixing a sample within a cartridge of a diagnostic system, wherein the changes in cross sectional area range from 0.0016 $in^2$ to 0.0011 $in^2$.

In some embodiments, the present disclosure relates generally to a method of mixing a sample within a cartridge of a diagnostic system, wherein the sample and assay reagent mixture is substantially free of foam.

In some embodiments, the present disclosure relates generally to a method of mixing a sample within a cartridge of a diagnostic system, wherein the sample and assay reagent mixture is substantially free of foam and foam-trapped beads.

In some embodiments, the present disclosure relates generally to a method of mixing a sample within a cartridge of a diagnostic system, wherein the back and forth motion of the pump produces a flow of the sample of greater than 5 microliters per second.

In some embodiments, the present disclosure relates generally to a method of mixing a sample within a cartridge of a diagnostic system, further comprising moving the sample and assay reagent mixture to an incubation zone.

In some embodiments, the present disclosure relates generally to a method of mixing a sample within a cartridge of a diagnostic system, further comprising moving the sample and assay reagent mixture to an incubation zone and incubating the sample and assay reagent mixture.

In some embodiments, the present disclosure relates generally to a method of mixing a sample within a cartridge of a diagnostic system, further comprising moving the sample and assay reagent mixture to an incubation zone using a fluidically connected pump and an optical sensor.

In some embodiments, the present disclosure relates generally to a method of mixing a sample within a cartridge of a diagnostic system, comprising using at least one cartridge assay replicate in fluidic communication with the pump and a probe pierced through a septum seal.

In some embodiments, the present disclosure relates generally to a method of mixing a sample within a cartridge of a diagnostic system, wherein the sample is introduced to the dry reagents slowly to reduce foaming.

In some embodiments, the present disclosure relates generally to a method of mixing a sample within a cartridge of a diagnostic system, wherein each of the steps performed are independent of pump accuracy.

In some embodiments, the present disclosure relates generally to a method of mixing a sample within a cartridge of a diagnostic system, wherein the mixing process is repeated one or more times corresponding to the number of cartridge assay replicates.

In some embodiments, the present disclosure relates generally to a method of mixing a sample within a cartridge of a diagnostic system, wherein fluidic elements of the cartridge include the fluidic channels and wells and are fluidically connected to a metering device.

In some embodiments, the present disclosure relates generally to a method of mixing a sample within a cartridge of a diagnostic system, wherein fluidic elements of the cartridge include the fluidic channels and wells and are fluidically connected to a metering device, a plasma cache, and a blood filtration module.

In some embodiments, the present disclosure relates generally to a method of mixing a sample within a cartridge of a diagnostic system, further comprising measuring the volume of the sample and assay reagent mixture within the fluidic channel using a fluidically connected pump, an optical sensor to detect a first air liquid transition and a second liquid air transition.

In some embodiments, the present disclosure relates generally to a method of mixing a sample within a cartridge of a diagnostic system, wherein the assay reagent is lyophilized.

In some embodiments, the present disclosure relates generally to a method of mixing a sample within a cartridge of a diagnostic system, wherein the assay reagent is dried.

In some embodiments, the present disclosure relates generally to a method of mixing a sample within a cartridge of a diagnostic system, wherein the assay reagent is comprised of one lyophilized pellet.

In some embodiments, the present disclosure relates generally to a method of mixing a sample within a cartridge of a diagnostic system, wherein the assay reagent is comprised of two lyophilized pellets.

In a still another embodiment, the present disclosure relates generally to a bead wash method for separating blood, plasma, and free label from beads with no human intervention within a cartridge of a diagnostic system, comprising drawing the sample containing beads within a fluidic channel until an optical sensor detects an air liquid transition of the sample, wherein the fluidic channel is fluidically connected to a pump; further drawing the sample into a portion of a fluidic pathway where a magnet of the diagnostic instrument makes contact with the portion of the fluidic pathway; contacting the magnet to the portion of the fluidic pathway to capture the beads within the sample at the portion of the fluidic pathway; aspirating a wash liquid pack from a reagent handling station probe fluidically connected to pump, wherein the pack contains segments of liquid buffer and air, and wherein the pack has cleaning qualities; dispensing the pack over the portion of the fluidic pathway with captured beads to wash the beads substantially free of sample and all unbound assay reagents; and removing the magnet from contact to fluidic pathway.

In some embodiments, the present disclosure relates generally to a bead wash method for separating blood, plasma, and free label from beads with no human intervention within a cartridge of a diagnostic system, wherein the wash liquid volume is less than 100 microliters.

In some embodiments, the present disclosure relates generally to a bead wash method for separating blood, plasma, and free label from beads with no human intervention within a cartridge of a diagnostic system, wherein the wash liquid pack comprises a staggered combination of liquid and air.

In some embodiments, the present disclosure relates generally to a bead wash method for separating blood, plasma, and free label from beads with no human intervention within a cartridge of a diagnostic system, wherein the wash liquid pack comprises a liquid-and-air combination.

In some embodiments, the present disclosure relates generally to a bead wash method for separating blood, plasma, and free label from beads with no human intervention within a cartridge of a diagnostic system, wherein the wash liquid pack comprises three liquid segments, surrounded by four air segments.

In some embodiments, the present disclosure relates generally to a bead wash method for separating blood, plasma, and free label from beads with no human intervention within a cartridge of a diagnostic system, wherein the beads are captured in a bead capture zone.

In some embodiments, the present disclosure relates generally to a bead wash method for separating blood, plasma, and free label from beads with no human intervention within a cartridge of a diagnostic system, wherein the bead wash efficiency is greater than 99%.

In some embodiments, the present disclosure relates generally to a bead wash method for separating blood, plasma, and free label from beads with no human intervention within a cartridge of a diagnostic system, comprising using a cartridge assay replicate in fluidic communication with a pump and a probe pierced through a septum seal.

In some embodiments, the present disclosure relates generally to a bead wash method for separating blood, plasma, and free label from beads with no human intervention within a cartridge of a diagnostic system, wherein the fluidic elements are fluidically connected to a metering device.

In some embodiments, the present disclosure relates generally to a bead wash method for separating blood, plasma, and free label from beads with no human intervention within a cartridge of a diagnostic system, wherein the fluidic elements are fluidically connected to a metering device, a plasma cache, and a blood filtration module.

In another embodiment, the present disclosure relates generally to a method of storing dry and liquid reagents together on a cartridge, comprising storing in the cartridge at least one liquid in at least one fluid-containing compartment of the cartridge; storing in the cartridge at least one dry reagent in at least one dry reagent-containing compartment, wherein the at least one fluid-containing compartment is adjacent to the at least one dry reagent-containing compartment on the cartridge, and wherein the cartridge has a pathway connecting the at least one dry reagent to at least one vapor from the liquid; and sealing a cartridge in an airtight package with a moisture-absorbent material, wherein the moisture-absorbent material out-competes the at least one dry reagent for water absorption that slowly diffuses from the liquid through a wall of the at least one fluid-containing compartment.

In some embodiments, the present disclosure relates generally to a method of storing dry and liquid reagents together on a cartridge, wherein the wall of the at least one fluid-containing compartment is made from a material having a low moisture vapor transmission rate.

In some embodiments, the present disclosure relates generally to a method of storing dry and liquid reagents together on a cartridge, wherein the wall of the at least one fluid-containing compartment is made from cyclic olefin copolymer.

In some embodiments, the present disclosure relates generally to a method of storing dry and liquid reagents together on a cartridge, wherein the moisture-absorbent material is a desiccant.

In some embodiments, the present disclosure relates generally to a method of storing dry and liquid reagents together on a cartridge, wherein the desiccant is DRIERITE®.

In some embodiments, the present disclosure relates generally to a method of storing dry and liquid reagents together on a cartridge, wherein the package is a foil pouch.

In another embodiment, the present disclosure relates generally to a desiccating system for a cartridge that has both stored liquids and dry reagents, comprising storing in the cartridge at least one liquid in at least one fluid-containing compartment of the cartridge; storing in the cartridge at least one dry reagent in at least one dry reagent-containing compartment; sealing a cartridge in an airtight package with a desiccant, wherein the cartridge has at least one passageway connecting the dry reagent and the cartridge exterior where a desiccant is located.

In some embodiments, the present disclosure relates generally to a desiccating system for a cartridge that has both stored liquids and dry reagents, wherein the at least one fluid-containing compartment is adjacent to the at least one dry reagent-containing compartment on the cartridge.

In some embodiments, the present disclosure relates generally to a desiccating system for a cartridge that has both stored liquids and dry reagents, wherein the at least one fluid-containing compartment is separated from the at least one dry reagent-containing compartment by a wall within the cartridge.

In some embodiments, the present disclosure relates generally to a desiccating system for a cartridge that has both stored liquids and dry reagents, wherein the at least one fluid-containing compartment is separated from the at least one dry reagent-containing compartment by a wall made of cyclic olefin copolymer.

In some embodiments, the present disclosure relates generally to a desiccating system for a cartridge that has both stored liquids and dry reagents, wherein the desiccant absorbs more water than the at least one dry reagent.

In some embodiments, the present disclosure relates generally to a desiccating system for a cartridge that has both stored liquids and dry reagents, wherein the rate of transport of water vapor to the desiccant is greater than the rate of transport of water vapor to the at least one dry reagent-containing compartment on the cartridge.

In some embodiments, the present disclosure relates generally to a desiccating system for a cartridge that has both stored liquids and dry reagents, wherein the desiccant is at least one molecular sieve.

In some embodiments, the present disclosure relates generally to a desiccating system for a cartridge that has both stored liquids and dry reagents, wherein the desiccant is silica.

It is contemplated that any method or composition described herein can be implemented with respect to any other method or composition described herein. The use of the word "a" or "an" when used in conjunction with the term "comprising" in the claims and/or the specification may mean "one," but it is also consistent with the meaning of "one or more," "at least one," and "one or more than one." The use of the term/phrase "and/or" when used with a list means one or more of the listed items may be utilized, e.g., it is not limited to one or all of the elements.

This summary of the embodiments does not necessarily describe all features or necessary features of the embodiments. The embodiments may also reside in a sub-combination of the described features.

BRIEF DESCRIPTION OF THE DRAWINGS

The accompanying tables and figures are incorporated in, and constitute a part of this specification.

DETAILED DESCRIPTION

Figure 1:
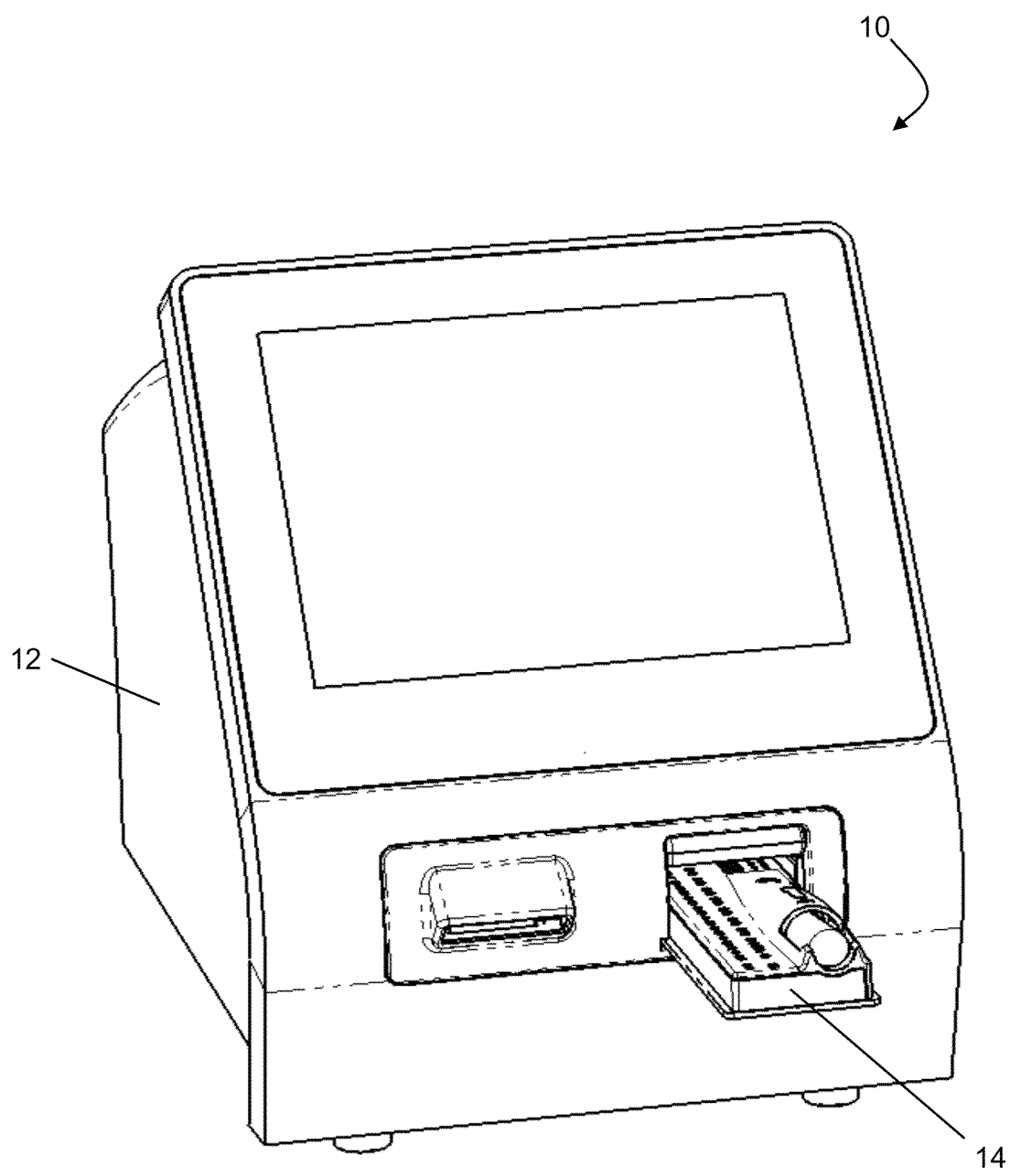
FIG. 1 is a perspective view a diagnostic system of an embodiment.

The present disclosure provides a clinical diagnostic system 10 comprising a clinical or diagnostic point-of-care instrument 12 and a disposable vehicle, such as a disposable cartridge 14, for completing diagnostic analyses in a fast and efficient manner in a clinical setting (see, e.g., FIG. 1). The diagnostic instrument 12 is generally described and briefly disclosed herein, and is further described in greater detail in the co-pending U.S. patent application filed on Mar. 15, 2013, entitled "DIAGNOSTIC SYSTEMS AND INSTRUMENTS;" Ser. No. 13/844,490, with inventors R. Cook, S. Cho, C. Davis, K. Dorsey, J. Harley, J. Leland, R. Matikyan, S. Otten, J. Peterman, B. Thomas, and assigned application Ser. No. 13/844,450, herein referred as the '450 application. The present disclosure describes the diagnostic system as a whole and also includes different subparts and modules of the diagnostic system as described herein. The different subparts and modules of the diagnostic system can be used in a clinical diagnostic instrument, but are not limited for that use.

There are multiple aspects of the cartridge 14 that are related to a diagnostic device 12. Thus, some embodiments include a discussion of a correlating diagnostic instrument 12 as part of the whole diagnostic system 10. For example, during operation of the diagnostic system 10, the cartridge 14 can interact with various components of a diagnostic instrument 12, including, but not limited to, a closed fluidic pathway, a motion assembly, an incubator, a pump, and an electrochemical detection system (not depicted).

In certain embodiments, a disposable cartridge can be used in the preparation and processing of a sample, for example, on an electrochemiluminescence (ECL) measurement instrument that has various components and uses various methods. Some of these methods include, but are not limited to, methods of blood filtration (e.g., using tangential flow), methods for liquid-air transition detection in the channels of the cartridge, methods for aliquoting a clinical sample via segmented metering, methods for mixing reagents, methods for incubating the assay and washing the sample matrix away. These methods are all covered in further detail herein.

Certain embodiments of a cartridge use unique components and features to facilitate the efficient and accurate preparation and processing of a biological sample. For example, in various embodiments, a disposable cartridge can store both liquid and dry reagents in relatively close proximity of one another. A novel storage location and a reagent handling station can be used for storing and accessing the liquid reagents, for example. Additionally, a method of using a desiccant to outcompete dry reagents for moisture within the packaging of the disposable cartridge can keep the dry reagents anhydrous. These aspects described herein can extend the shelf life of a cartridge. Various failsafe mechanisms to prevent the use of a used or damaged cartridge are also provided herein.

The cartridge is self-contained so that the sample, i.e., the patient blood, remains within the cartridge and neither blood nor plasma contacts the diagnostic instrument or, more specifically, the probes on the diagnostic instrument. With the exception of an electrochemiluminescence (ECL) measurement readout performed within the diagnostic instrument, all processing of the diagnostic test, such as an immunoassay, is conducted within the cartridge. The diagnostic system largely uses fluid motions so that for most of the cartridge fluid motions, pressure-driven flow is used, where the pressure is created by a pump in the diagnostic instrument. All cartridge functions are tightly time controlled.

Figure 13:
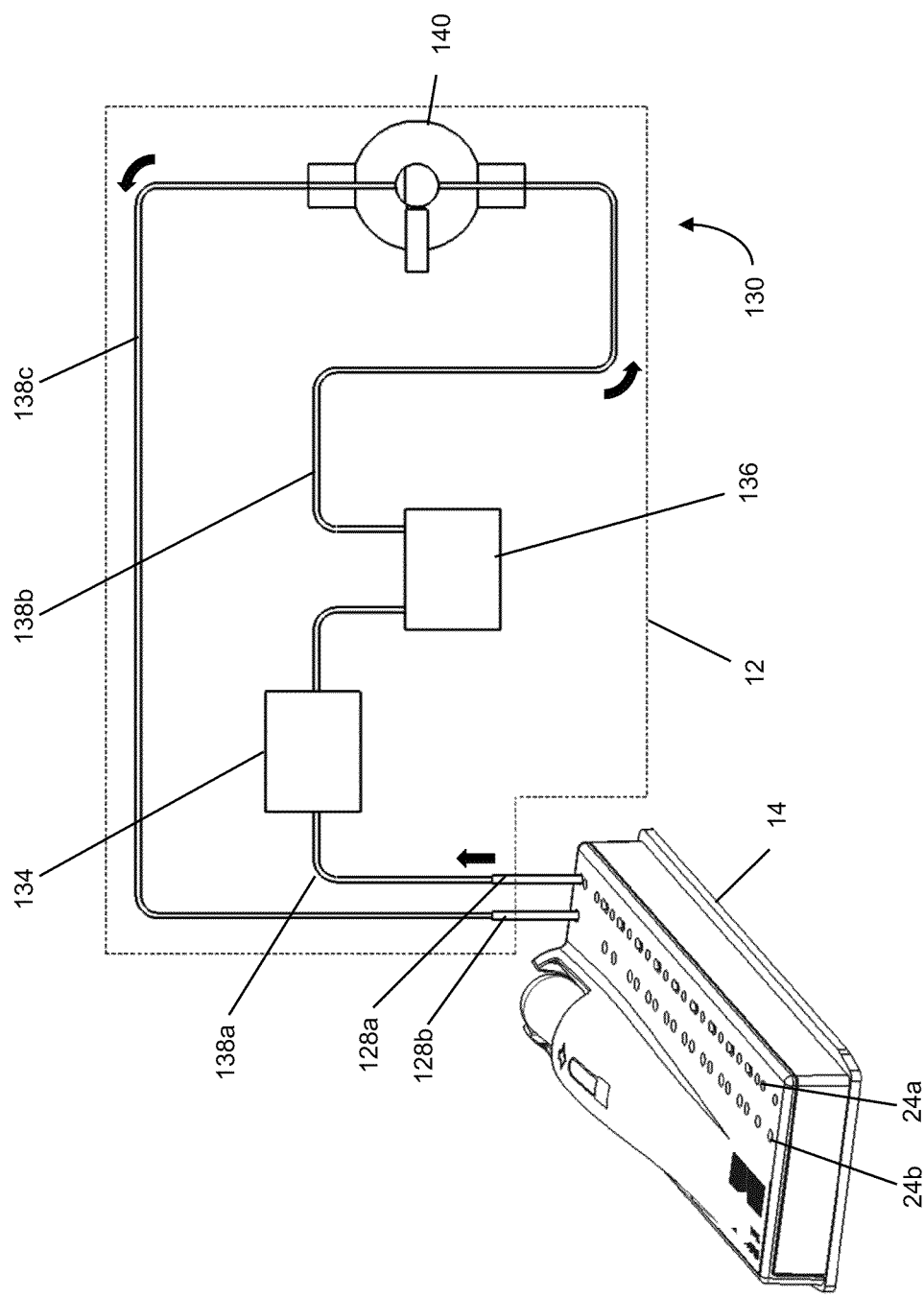
FIG. 13 is a schematic drawing of a fluidics system of an embodiment.

The fluidic control elements of the diagnostic instrument 12 can fluidically communicate with the cartridge 14 through a closed fluidic pathway 130 having a substantially single direction of flow (e.g., see FIG. 13). This closed fluidic approach permits test materials to be withdrawn from the cartridge 14, and then after processing during the diagnostic test, to be returned as waste to the cartridge 14 by means of a continuing closed-loop fluidic path 130, thereby avoiding the used processed materials from interfering (e.g., crossing paths with unused materials causing contamination or unwanted mixing) with subsequent tests. Thus, the substantially single direction of the flow and the closed configuration serves to reduce the potential for carryover between tests. The arrows in FIG. 13, for example, indicate the single direction of flow for an embodiment.

Cartridge Industrial Design.

The designs of certain embodiments of a diagnostic cartridge are disclosed in co-pending U.S. Design application Nos. 29/420,961 and 29/420,967, both filed on May 15, 2012, and each of which is herein incorporated by reference in its entirety. Images contained within those disclosures prescribe examples of diagnostic cartridges of the diagnostic system, and designs thereof, which relay both the function and form, and the connection between the product, the user, and the environment. Such images merely represent examples of cartridges, diagnostic systems, and the present disclosure is not limited to these particular designs.

Figure 2A:
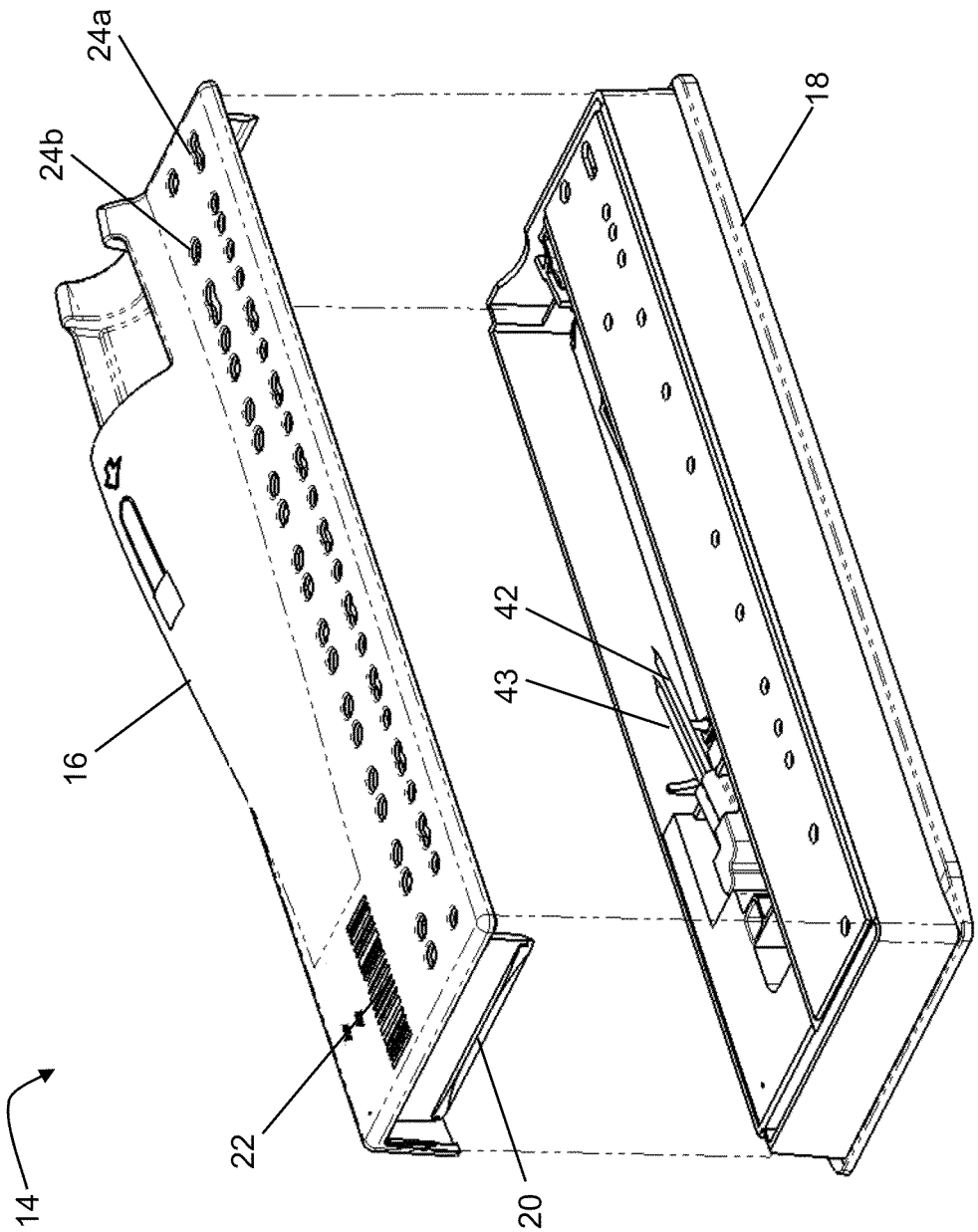
FIG. 2A is an exploded perspective view of a cartridge of an embodiment.

According to various embodiments, a disposable cartridge 14 can be formed from a cover 16 and a body 18, for example, as depicted in FIG. 2A. The cartridge cover 16 can have at least one retaining feature to facilitate connecting the cover 16 to the cartridge body 18. For example, the at least one retaining feature can include a snap fit 20 on one or both ends of the cover 16. The snap fit 20, also shown in FIGS. 2B and 2C, can have a pull on each end of the cover to ensure a secure fit to the cartridge body 18. It is contemplated that additional retaining features known in the art can be designed and included in the cover 16 to assist in securing the cover 16 to the body 18, including, but not limited to, press fits, tabs, spring locks, and over-molded magnets. With reference to FIG. 2A, the cover 16 can assist in guiding a blood collection tube, such as a commercially available blood collection tube (i.e., a VACUTAINER®), onto at least one needle 42, 43 integrated into the body 18. The cover 16 also serves to protect an operator from the at least one needle's 42, 43 sharp point.

Figure 2B:
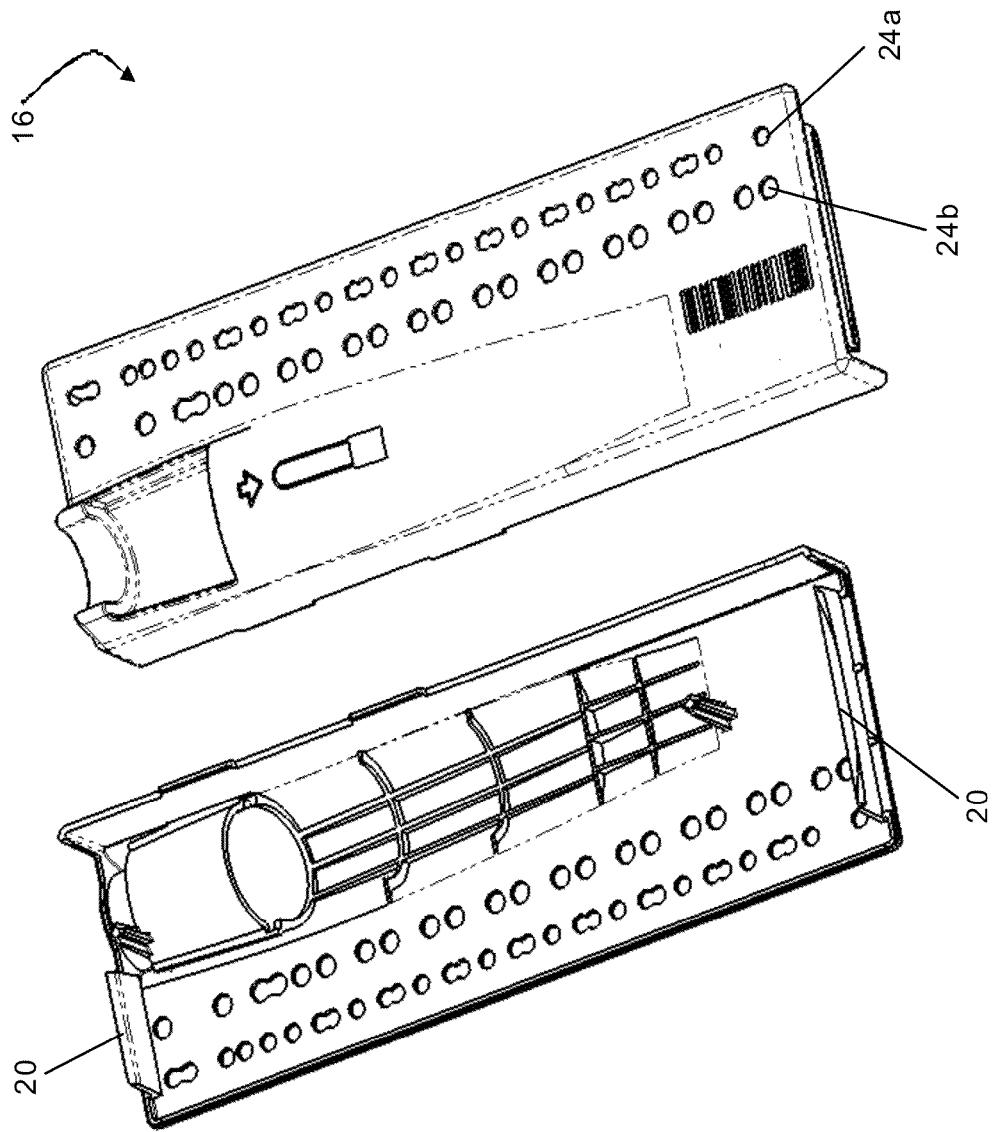
FIG. 2B is a perspective view of the front and back of a cartridge cover of an embodiment.
Figure 2C:
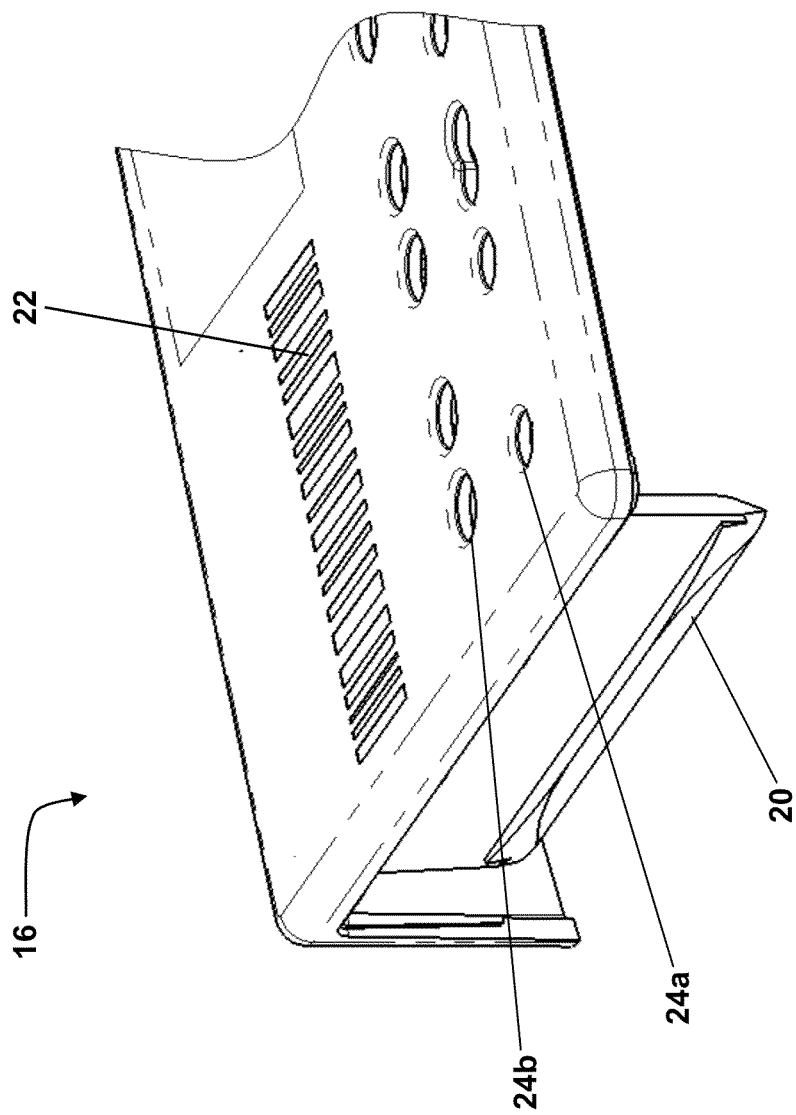
FIG. 2C is a perspective view of a portion of a cartridge cover of an embodiment.

The cover 16 has a flat area which makes contact with and covers the body 18, effectively covering and protecting the components of the body 18. No liquid or air tight seals are needed between the cover 16 and the rest of the cartridge 14. A barcode 22 can be placed on a portion of the flat area of the cover 16 for identification as part of one of the many failsafe mechanisms incorporated into the diagnostic system 10. The cover 16 can be formed with a plurality of holes 24a, 24b in at least two rows, for example, as shown in FIGS. 2A-2C. The plurality of holes 24a, 24b are the areas of the cover 16 through which at least one probe 128 (See, e.g., FIG. 12) of a diagnostic instrument can interface with the cartridge 14. One of the rows of the plurality of holes, or first probe holes 24a, can interface with a first probe 128a, and the other row of holes, waste probe holes 24b, can interface with a waste probe 128b of the diagnostic instrument (See, e.g., FIG. 13). The waste probe holes 24b can be 0.015 in. larger in diameter (0.095 in. vs. 0.080 in.) to provide a greater tolerance in position variation of the waste probe 128b as it interfaces with the cartridge 14. The cover 16 may also make the cartridge 14 as a whole look more aesthetically pleasing.

The cover 16 can be injected molded out of a variety of sturdy materials, such as, poly(methyl methacrylate) (PMMA), polycarbonate (PC), polycarbonate/Acrylonitrile butadiene styrene (PC/ABS) blends. It is contemplated that other materials may be used to form the cover 16 depending on desired specifications and manufacturing goals for the disposable cartridge 14, such as, for example, a polycarbonate/acrylonitrile butadiene styrene such as GE Cycoloy HC 1204HF, a polycarbonate such as Sabic Lexan (PC) EXL9134, polyethylene terephthalate (PET), polypropylene (PP), polyvinyl chloride (PVC), and Teflon. It is contemplated that other known methods of forming the cover 16 can be employed, including, but not limited to casting, rotational molding, thermoforming, compression molding, and injection molding.

In certain embodiments, the cartridge 14 can have features useful for blood filtration, assay processing regions (each region sometimes referred to as a cartridge assay replicate or CAR), probe wash areas and draw reservoirs filled with ECL read buffer (can also be referred to as a read buffer filled reagent handling station (RHS)), and a pump storage liquid filled RHS. Most of the components of the cartridge 14 are attached to the cartridge body 18, including, for example, the cartridge cover 16, a blood filter 19, at least one needle 42, 43, and multiple seals (See, e.g., FIGS. 2A, 3A,3B, and 4A).

The cartridge body 18 can be injection molded out of a variety of sturdy materials such as a low moisture vapor transmission rate (MVTR) plastic such as Topas grade AS 5013 (MVTR=0.03 g mm/(m² day) at 23° C. and 85% RH), Topas grade 8007 (MVTR=0.025 g mm/(m² day) at 23° C. and 85% RH), or Zeonor 1420R (MVTR=0.029 g mm/(m² day) at 25° C. and 90% RH). It is contemplated that other materials may be used to form the body 18 depending on desired specifications and manufacturing goals for the disposable cartridge 14, including, but not limited to, high density polyethylene (HPDE), polypropylene (PP), and polyethylene terephthalate (PET). It is contemplated that other known methods of forming the body 18 can be employed, including, but not limited to, casting, rotational molding, thermoforming, pressure forming, compression molding, and injection molding. The body 18 also can have at least one notch 18a (See, e.g., FIG. 3B) on at least one side of the body 18 to assist in motion control of the cartridge 14 by holding the cartridge 14 in place during operation within the diagnostic instrument 12. The cartridge 14 has several additional features and components which will now be described in more detail in relation to the functional aspect of each feature and component.

Bottom Seal.

In various embodiments, the cartridge 14 includes a multi-layer, heat-sealable film, also referred to as a bottom seal 26. The bottom seal 26 forms, in part, the bottom surface of the cartridge 14, as depicted in FIGS. 3B and 3C. The bottom seal 26 can have a notch 26a cut out to correlate to the notch 18a of the body 18. The body 18 can contain at least one fluidic channel 15 which can be formed as part of the body 18 during the injection molding process.

The bottom seal 26 has significantly improved physical characteristics and therefore provides improved cartridge performance such as precision and accuracy. For example, the fluidic channels 15 are also formed in part and sealed by the bottom seal 26. In particular, the bottom seal 26 encloses at least one volumetric fluidic channel 15 and forms a known, measurable volume. It is undesirable for the volume to change during the manufacturing of the disposable cartridge 14. Due to the properties of the film materials used to make the bottom seal 26, highly accurate fluidic volumetric channels can be formed. The separate steps taken to form the fluidic channels 15 are recommended to satisfy the tightly controlled volume requirements of each fluidic channel 15 and ensures the level of high accuracy desired for this formation process.

Additionally, the multiple layers that comprise the bottom seal 26 are specifically selected film materials that can be taken to a manufacturer for lamination or joining of the layers and/or die cutting. The selection includes materials that will melt at a temperature below that of the melting temperature of the body 18 material. The bottom seal 26 can also bond or join to the cartridge body 18 surface with high seal strength such that the enclosed fluidic channels 15 are sufficiently sealed so as to withstand high pressures or high vacuum levels.

The bottom seal 26 can be cut to various sizes as necessary during assembly. It is desirable to have the bottom seal 26 cut to a size and shape that covers and seals the fluidic channels 15 while not extending beyond the edges of the body 18 to avoid overhang which may interfere with cartridge motion during processing of the diagnostic system 10. The size and shape of the diameter of the bottom seal 26 can be configured to satisfy individual manufacturing and design requirements and are not meant to be limited by the description of the embodiments described herein. Having a bottom seal 26 that does not extend all the way to the edges of the body 18 also allows the snap fit features 20 of the cover 16 to properly engage the body 18.

In certain embodiments, the bottom seal 26 can be constructed from a combination of a thermal adhesive layer and a support layer. The thermal adhesive layer can be directly coated, formed or joined onto the support layer. Using a heat seal process, the thermal adhesive layer is able to join and seal the support layer to the cartridge body 18 to enclose the fluidic channels 15. The thermal adhesive layer thickness is sufficiently thin such that during heat sealing, melt from the thermal adhesive layer does not substantially flow into the fluidic channels and cause unwanted volumetric changes. In particular, flow of melt, i.e., flash, may cause unwanted volumetric changes to the fluidic channels, which can be avoided with a low thickness of the thermal adhesive layer.

The heat seal temperature is a characteristic of the thermal adhesive material of the thermal adhesive layer, and is advantageously lower than the melting point or glass transition temperature of the body 18 material being sealed. For example, in certain embodiments, the heat seal temperature of an exemplary thermal adhesive material can be 113° C., which is a temperature significantly lower than the glass transition temperature of the cyclic olefin copolymer, i.e., 136° C., used for injection molding the body 18. If the heat seal temperature is substantially the same or greater than the melting point or glass transition temperature of the body 18, then during heat sealing, the structure of the fluidic channels 15 may distort due to melting of the body 18 material. Any distortion to the fluidic channels 15 can change the volume which is undesirable. Thus, it is desirable that the fluidic channels 15 maintain the volumetric integrity with which each was designed.

The thermal adhesive processing temperature can be adapted to suit the desired manufacturing design, for example, by selecting different materials for the formation of the thermal adhesive layer depending on the type of material used for the body 18. Examples of suitable materials for the thermal adhesive layer include, but are not limited to, copolymers of ethylene and vinyl acetate (EVA), EVA emulsions (polyvinyl acetate copolymers based on vinyl acetate and plasticized with vinyl acetate ethylene, vinyl acetate ethylene (VAE) emulsions, vinyl acetate ethylene copolymer (VAE), copolymer adhesive, ethylene methacrylic acid copolymer (EMAA), ethylene acrylic acid copolymer, polyolefin copolymer, ethylene copolymer, propylene copolymer, polyvinyl chloride based thermoplastic resin, polyvinylidene chloride based thermoplastic resin, acrylate and styrene acrylate based thermoplastic resin, acrylate/polyolefin based thermoplastic resin, styrene copolymer based thermoplastic resin, polyester based thermoplastic resin, heat seal lacquer, or other similar materials.

The thermal adhesive layers are designed to be as thin as possible to conserve space within the overall cartridge 14 design without sacrificing effectiveness of the cartridge 14 design. In general, the thermal adhesive layers can have a thickness of less than about 1.5 mil. For example, the thermal adhesive layers can have a thickness ranging from about 0.2 mil to 1.2 mil, about 0.3 mil to about 1.0 mil, about 0.4 mil to about 0.8 mil, or about 0.5 mil to about 0.6 mil. It is contemplated that the thermal adhesive layers can have a thickness of about 1.2 mil, about 1.0 mil, about 0.8 mil, about 0.6 mil, about 0.5 mil, about 0.4 mil, about 0.3 mil, or about 0.2 mil, or any thickness in between these values and less than about 1.5 mil.

Typically, the thermal adhesive layer is thin and thus a support layer is necessary to provide sufficient stiffness, rigidity, high flexural modulus, and re-enforcement to the bottom seal 26. The support layer adds stiffness to the thin thermal adhesive layer such that the enclosed fluidic channels 15 have a flat channel surface. As a consequence, the volumes of the fluidic channels are precise and accurate across many cartridges. The support layer can be made of a material that does not melt, deflect or substantially deform during the heat sealing process. For example, the support layer can be made of polyethylene terephthalate (PET), polyvinyl chloride (PVC), cyclic olefin copolymer (COC), polyvinylidene chloride (PVDC), polystyrene, polycarbonate (PC), poly(methyl methacrylate) (PMMA), polysulfone, acrylonitrile butadiene styrene (ABS), or other similar materials. It is desirable to use materials for the support layer that are sufficiently stiff and provide high flatness on both surfaces of the combined layers. For example, in certain embodiments, the support and stiffness of the overall bottom seal 26 is derived from the support layer with PET being an example. The use of PET is also advantageous because of the characteristic dimensional stability, high flatness, and high parallelism between surfaces.

The support layer is designed to be as thin as possible to conserve space within the overall cartridge 14 design without sacrificing effectiveness of the cartridge 14 design. In general, the support layer will be thicker than the thermal adhesive layer to provide sufficient support and stiffness to the bottom seal 26. Accordingly, the support layers can have a thickness of less than about 5.0 mil. For example, the support layer can have a thickness ranging from about 4.5 mil to about 5.0 mil, from about 4.0 mil to about 4.5 mil, from about 3.0 mil to about 4.0 mil, or from about 2.5 mil to about 3.0 mil or any thickness therebetween. It is contemplated that the support layer can have a thickness of about 5.0 mil, about 4.5 mil, about 4.0 mil, about 3.7 mil, about 3.5 mil, about 3.0 mil, or about 2.5 mil.

When the thermal adhesive and support layers are combined, it is important to have smooth surfaces of the combined layers to ensure that the volume of the fluidic channels 15 is not affected by abnormalities in the surface of the bottom seal 26. It is also desirable to use materials that are dimensionally stable (low shrinkage) and have high parallelism between surfaces. Such materials should also be chemically compatible with clinical laboratory specimens, such as blood or plasma.

In certain embodiments, the bottom seal 26 can include an additional tie layer. The tie layer facilitates the adhesion of the thermal adhesive layer to the support layer. In certain embodiments, for example, the PSA layer serves to tie layers together, such as the thermal adhesive layer and the support layer. The tie layer can enable dissimilar materials for the thermal adhesive layer and support layer to be used and joined. The tie layer is advantageously thin, and does not melt or deform during the heat seal process. Examples of suitable materials for the tie layer include but are not limited to pressure sensitive adhesive (PSA), polyolefin resins, anhydride modified polyolefin, double side adhesive tapes, or similar materials.

The tie layer is designed to be as thin as possible to conserve space within the overall cartridge 14 design without sacrificing effectiveness of the cartridge 14 design. In general, the tie layers can have a thickness of less than about 1.5 mil. For example, the tie layers can have a thickness ranging from about 0.2 mil to 1.2 mil, about 0.3 mil to about 1.0 mil, about 0.4 mil to about 0.8 mil, or about 0.5 mil to about 0.6 mil. It is contemplated that the tie layers can have a thickness of about 1.2 mil, about 1.0 mil, about 0.8 mil, about 0.6 mil, about 0.5 mil, about 0.4 mil, about 0.3 mil, or about 0.2 mil, or any thickness in between these values and less than about 1.5 mil.

The materials chosen for the thermal adhesive layer, the support layer, and the tie layer may be optically transparent or optically opaque. When used, the optically transparent materials can facilitate the functions of the diagnostic system such as, for example, the use of optical sensors within the diagnostic instrument to meter appropriate divisions of fluids within the fluidic channels. The materials chosen for the thermal adhesive layer, the support layer, and the tie layer may be sufficiently thin to have low thermal resistance. The bottom seal 26 can have a total thickness which is the sum of the individual layers. Additionally, the materials chosen for the bottom seal 26 layers may bond or join to the device surface with high seal strength such that the enclosed fluidic channels are sufficiently sealed so as to withstand high pressures or high vacuum levels.

In some embodiments, the bottom seal 26 can be comprised of materials that are bondable to plastics commonly used for injection molding, including a cyclic olefin copolymer (COC). It is contemplated that when other materials are used for the injection molding of the cartridge body 18, then the thermal adhesive layer material would be altered as well. In particular, the thermal adhesive layer material composition depends on the composition of the substrate or cartridge body 18, so it is desired to have a thermal adhesive layer with a lower melting point than the body 18. Examples of suitable combinations of thermal adhesive layers with different materials for the body include, but are not limited to, the following pairs.

| Body Material | Thermal Adhesive |
| --- | --- |
| cyclic olefin copolymer | ethylene vinyl acetate copolymer |
| polyvinyl chloride | PVC based thermoplastic resin |
| polystyrene | acrylate and styrene acrylate-based thermoplastic resin |
| polypropylene | acrylate/polyolefin-based thermoplastic resin |
| polyethylene | acrylate/polyolefin based thermoplastic resin |
| PET | polyester based thermoplastic resin |

It contemplated that more than one of each layer may be used to construct the bottom seal 26 depending on the materials selected for each layer and the desired properties and thickness of the bottom seal 26. For example, a bottom seal construction may include alternating layers of thermal adhesive layers and tie layers on each side of a support layer.

An embodiment of a bottom seal 26 can be constructed from a thermal adhesive layer comprising a copolymer adhesive with a thickness of about 0.6 mil, a support layer comprising PET with a thickness of about 3.0 mil and a tie layer comprising pressure sensitive adhesive (PSA), with a thickness of about 1.2 mil. Such an example of a bottom seal 26 is able to seal fluidic channels 15 of the body 18 of a cartridge 14, formed by injection molding of a cyclic olefin copolymer with a glass transition temperature of 136° C., such as, for example, TOPAS® 5013.

In another embodiment, the bottom seal 26 can be constructed from two layers joined by lamination with a total thickness of about 5.4 mil, which is the sum of the layers. A thermal adhesive layer can be Transilwrap Trans-Kote® PET/MR Laminating Film with a thickness of about 1.2 mil. A support layer can be Adhesive Research ARCare 7843 with a thickness of about 4.2 mils. The low thickness of the bottom seal 26 permits the materials to be readily die cut. The materials can also be expected to have a low thermal resistance with this low thickness. The materials selected can be optically transparent.

In another embodiment, the bottom seal 26 can be constructed from two layers joined by lamination with a total thickness of about 5.4 mil, which is the sum of the layers. A first layer is constructed from the combination of a thermal adhesive layer with a thickness of about 0.6 mil and a support layer comprised of PET with a thickness of about 0.6 mil. A second layer is comprised of the tie layer made from single-sided PSA tape, e.g., composed of a 1.2 mil adhesive layer and a 3.0 mil PET support layer. The face of the single-sided tape opposite the pressure sensitive adhesive is very smooth. The PSA layer serves to tie the first layer to the second layer. The low thickness of the bottom seal 26 permits the materials to be readily die cut. The materials can also be expected to have a low thermal resistance with this low thickness. The materials selected can be optically transparent.

Top Seal.

Figure 3A:
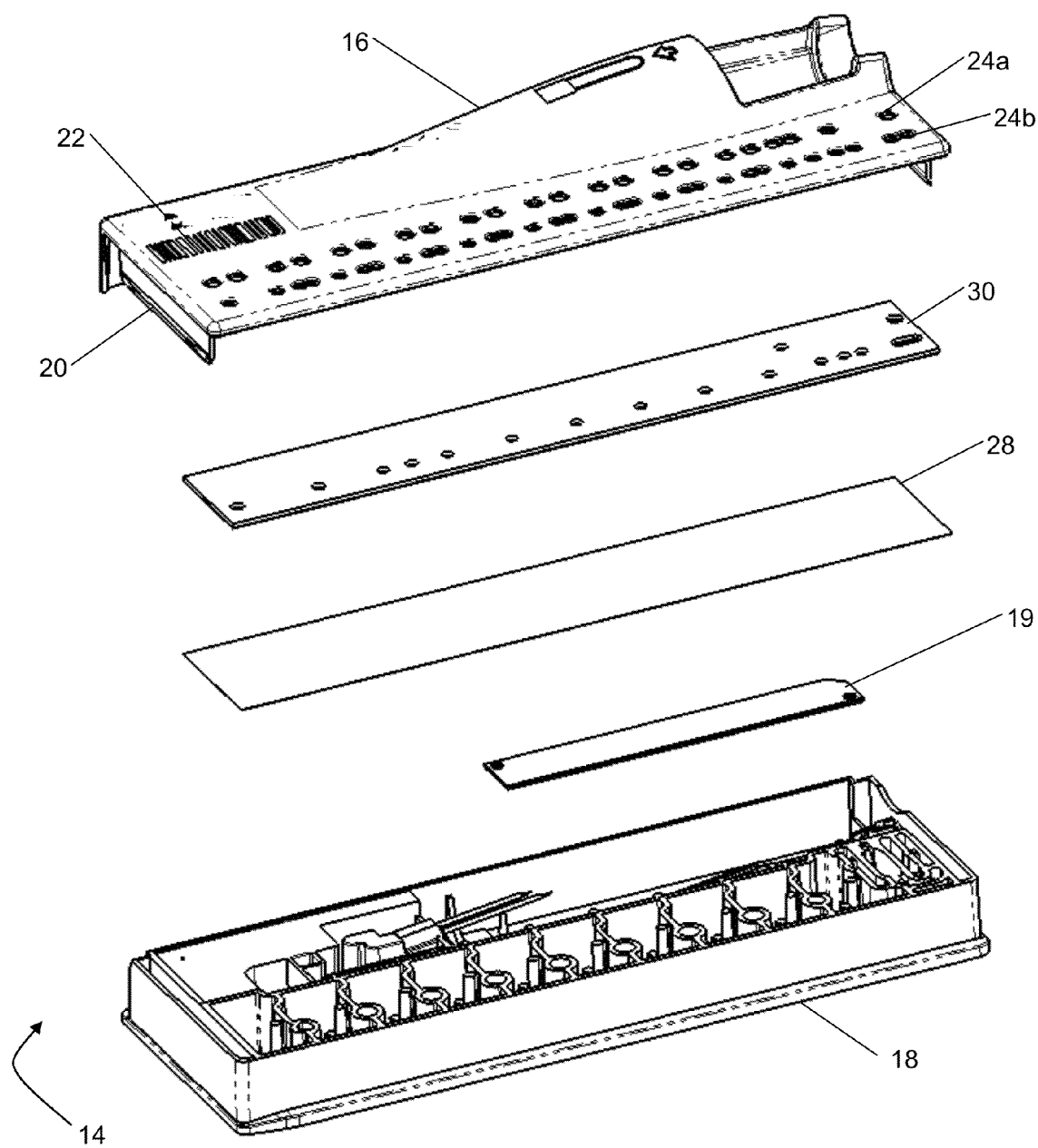
FIG. 3A is an exploded perspective view of a cartridge of an embodiment.
Figure 3B:
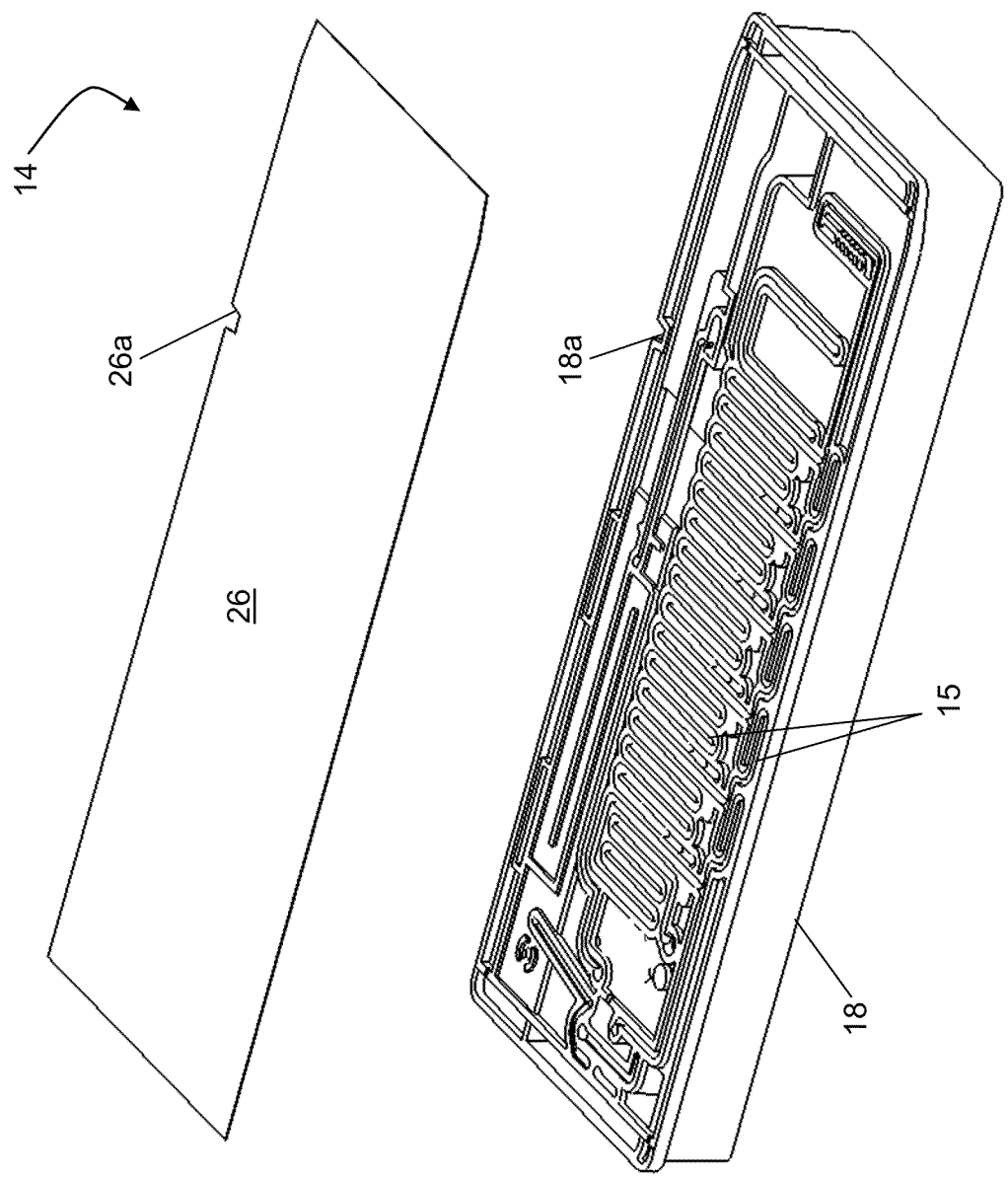
FIG. 3B is an exploded perspective view of the bottom of a cartridge of an embodiment.
Figure 3C:
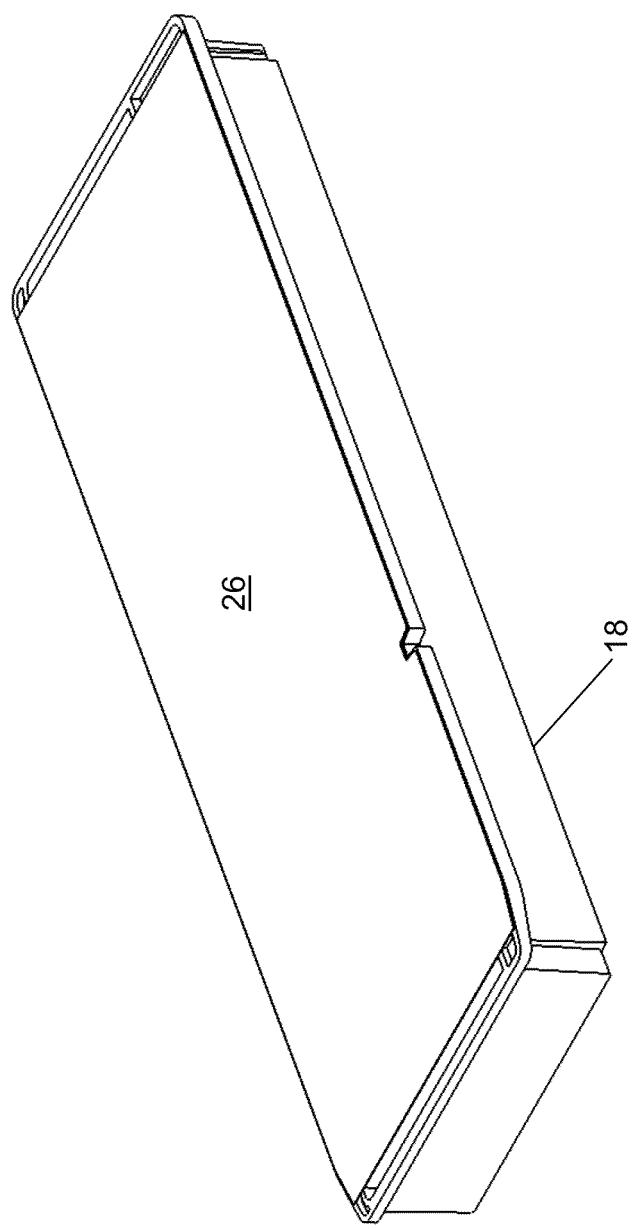
FIG. 3C is a perspective view of the bottom of a cartridge of an embodiment.

The cartridge 14 includes a top seal 28, as depicted in FIG. 3A. The top seal 28 can be used as a lid to seal the portions of the cartridge body 18 that hold liquid and dry reagents used during processing of the diagnostic test.

The top seal is comprised of a barrier layer and a laminating element.

The top seal can be joined to the cartridge body using a laminating element such as heat seal coating, pressure sensitive adhesive (PSA), pressure sensitive adhesive tape, thermal adhesive, transfer tape, transfer adhesive, double-sided tape, tie layer, adhesive film, or similar materials.

Figure 4A:
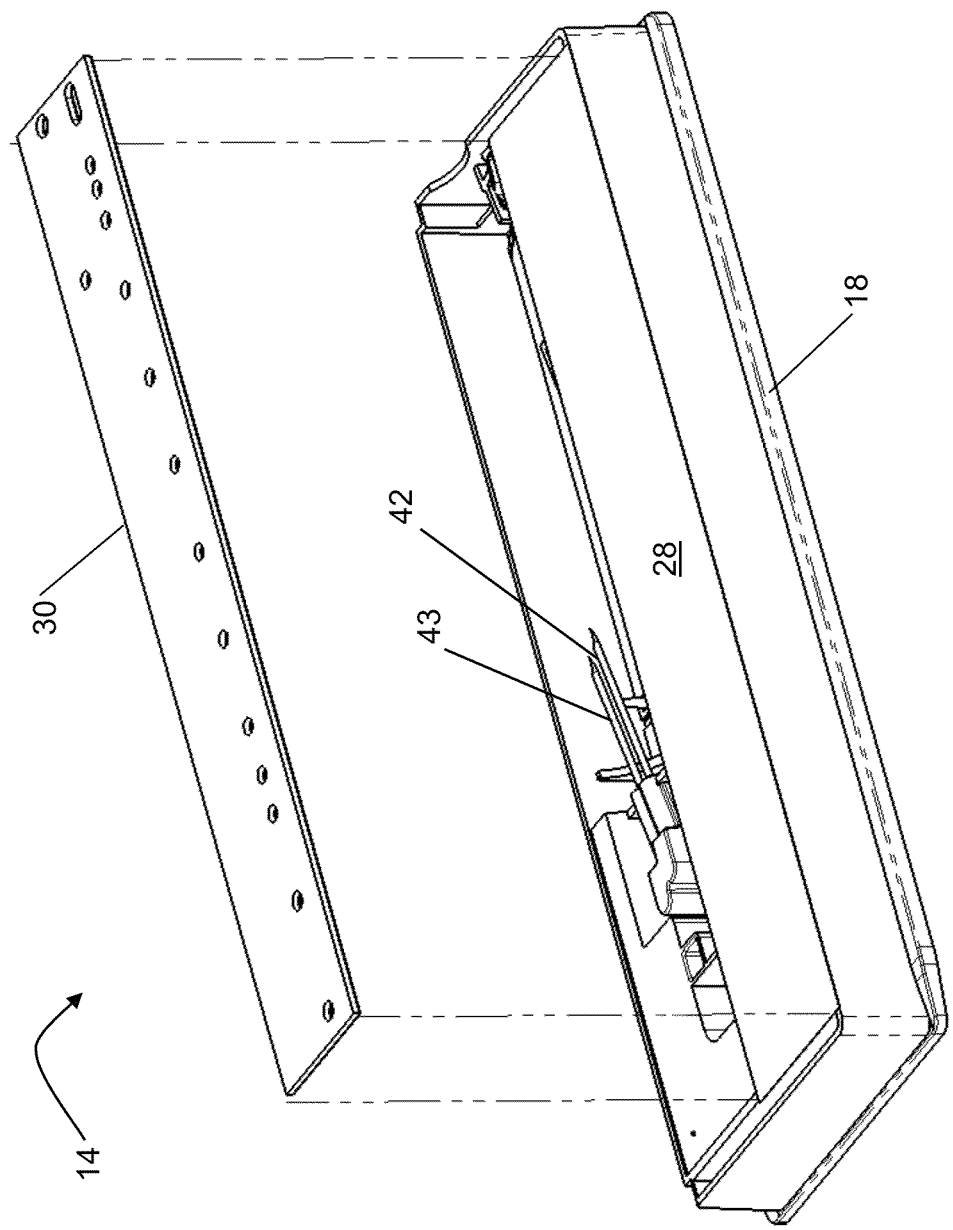
FIG. 4A is an exploded perspective view of a septum seal and a cartridge of an embodiment.
Figure 4B:
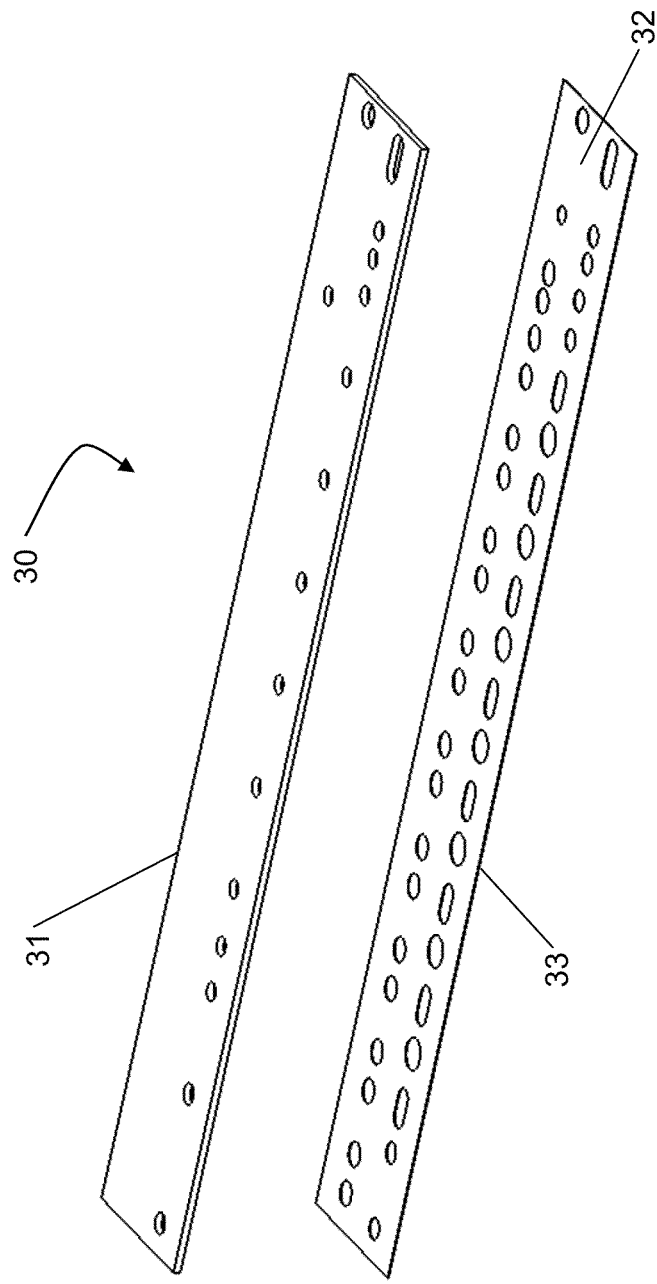
FIG. 4B is a perspective view of a septum seal and a cartridge of an embodiment.
Figure 4C:
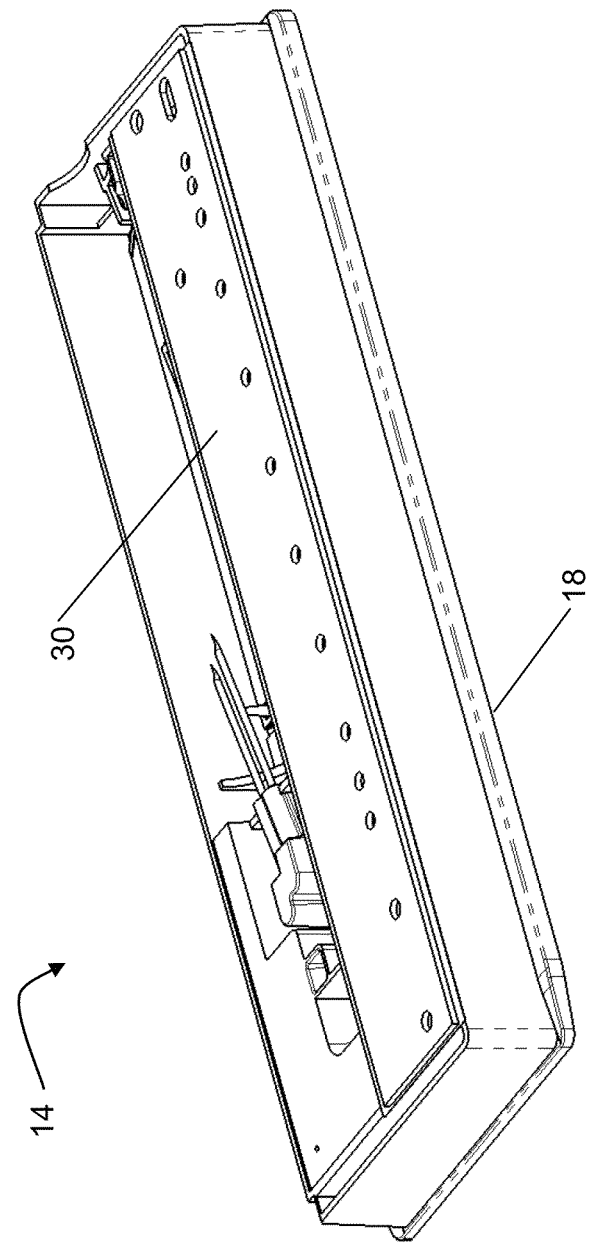
FIG. 4C is a perspective view of a septum seal of an embodiment.

The top seal 28 can be die-cut or otherwise configured to have a size and shape that fits and covers only the liquid and dry reagent holding portions of the body 18 so that there is no overhanging material to interfere with cartridge performance, for example, as shown in FIG. 4A. FIG. 4A provides an embodiment of a cartridge body 18 illustrating how the top seal 28 and septum seal 30 are joined to the body 18. FIG. 4C provides an embodiment of a cartridge body 18 illustrating how the septum seal 30 is joined to the body 18.

The top seal 28 can be made from high barrier materials that will reduce or prevent evaporation of the stored liquids. It is desirable for the top seal 28 to have a very low moisture vapor transmission rate (MVTR). For example, a material that has an MTVR that is at least two times (2×) lower than the material used to form the cartridge body 18 will not greatly contribute to any water loss from the liquid being sealed by the top seal 28. Suitable materials for the top seal 28 include, but are not limited to, aluminum foil, aluminum alloy foils, metal alloy foils, high MVTR films, high barrier films, COC films, ACLAR® films (a type of fluorinated-chlorinated resins), films made of fluorinated-chlorinated resins, duplex films, triplex films, WinCare DF10HJ712A (a Universal Sealing Blister Foil from the company WinPak).

Septum Seal.

The septum seal 30 is joined to the top face of the top seal 28 using pressure sensitive adhesive, heat sealing, bonding, or lamination. The septum seal 30 is a multi-layer film structure that is designed to connect fluidic elements between the cartridge 14 and the diagnostic device 12 using a probe. For example, the septum seal 30 can be used to establish and switch fluidic connections between the cartridge and fluidic control elements, such as a pump, a tubing assembly or fluidic pathway, and at least one probe of a diagnostic instrument. The septum seal 30 is also a multi-layer film structure that is designed to connect cartridge fluidic elements to the atmosphere using a probe. The septum seal 30 can also serve as a top seal to seal liquid filled wells or reservoirs located on the cartridge 14. The septum seal 30 can also serve as a means to clean the probe free of liquids and solids such as salts by squeegee action.

The septum seal 30 can be constructed of multiple layers including, for example, at least one septum layer 31, at least one laminating element 32, and at least one support layer 33. The septum seal 30 can have various combinations of these layers all joined together to form the multi-layer film structure. The layers can be combined to form different combinations of layers before forming the completed septum seal 30 as well as shown in FIG. 4B. However, it is desirable to have at least one septum layer 31 and at least one support layer 33 in a septum seal 30.

The septum layer 31 is a thin partition, film, membrane or similar structure which is pierceable, reversibly stretchable, elastic, reversibly compressible, re-sealing, self-sealing, prevents the exchange of fluids and gases, seals against a probe, and is re-addressable by a probe at the same location. The septum layer 31 has one or more probe addressable locations (shown as holes in the layers in FIG. 4B). The septum layer 31 can be made from a variety of materials that provide these qualities, including, but not limited to, synthetic rubber, silicone rubber, elastomers, fluoroelastomers, natural rubber, copolymers of hexafluoropropylene and vinylidene fluoride, terpolymers of tetrafluoroethylene, vinylidene fluoride and hexafluoropropylene, perfluoromethylvinylether polymers, butyl rubber, or similar materials.

The septum layer 31 also can be made of a material that has a hardness of less than or equal to 110 Durometer (Shore A). The septum layer 31 can have a plurality of holes 31a, in at least one row, cut out of the layer in a predetermined pattern that can correspond to the other layers of the septum seal 30, as well as the holes 24 in the cartridge cover 16, all of which correlate to the points of contact from the probes of the diagnostic instrument 12 during operation.

The septum layer 31 can have varying thicknesses depending on the materials used for each of the layers within a given septum seal 30. For example, the septum layer can have a thickness of less than or equal to $\frac{1}{10}$ inch, less than or equal to $\frac{1}{8}$ inch or less than or equal to $\frac{1}{6}$ inch.

The support layer 33 is a film, sheet, foil or similar material which reduces stretch and tension of septum layer, adds rigidity to overall structure, adds stiffness to overall structure, re-enforces overall structure, has high flexural modulus, reduces elongation of the septum layer, and is puncturable. In particular, the support layer 33 can prevent the septum layer 31 from breaking and stretching when pierced by a probe, for example. Examples of suitable materials for the support layer 33 include, but are not limited to, metals such as, aluminum, aluminum alloys, metal alloys, foils, rigid films, plastics sheeting, polytetrafluoroethylene, polyvinyl chloride, polyester, and polymers thereof. In an exemplary embodiment, the support layer 33 can be made from aluminum foil.

The support layer 33 can have varying thicknesses depending on the materials used for each of the layers within a given septum seal 30. For example, the support layer can have a thickness of less than or equal to 7 mils, less than or equal to 6 mils, less than or equal to 5 mils, less than or equal to 4 mils, less than or equal to 3 mils, less than or equal to 2 mils, or less than or equal to 1 mil. The support layer 33 can have a plurality of holes, in at least one row, cut out of the layer in a predetermined pattern that can correspond to the other layers of the septum seal 30, as well as the holes 24 in the cartridge cover 16, all of which correlate to the points of contact from the probes of the diagnostic device during operation.

The purpose of the support layer 33 is to facilitate the piercing of the septum layer 31 by a probe of the diagnostic instrument. The support layer 33 adds stiffness to the underside of the septum layer 31 for the purposes of limiting the stretch of the elastic septum layer 31 during probe entry or withdrawal. Unwanted stretching of the septum layer 31 can cause significant pressure transients (positive pressure or vacuum) within the fluidic channels of the cartridge 14. Such instances induce unintended or variable fluid motions within the channels 15 which disrupt or alter the normal positions of the fluid samples.

The laminating element 32, underneath the septum layer in FIG. 4B, refers to a thin material used to join or bond layers together. A laminating element 32 typically uses adhesive as the means to hold together materials in layers. For example, a laminating element 32 may be a pressure sensitive adhesive (PSA), thermal adhesive, heat seal coating, transfer tape, transfer adhesive, double-sided tape, tie layer, adhesive film, or similar materials. In some embodiments, the laminating element 32 can contribute to the multilayer film structure the same properties as the support layer 33, in that some laminating elements add rigidity, add stiffness, re-enforce, or reduce elongation. For example, the laminating element 32 can be a double-sided tape with carrier, where the carrier also provides support in the same manner as the support layer 33. In some embodiments, there is sufficient stiffness, rigidity, re-enforcement, or reduction of elongation by the double-sided tape carrier, such that the laminating element is also the support layer, or more specifically, the double-sided tape carrier is the support layer and the adhesives of the tape serve as the laminating elements.

The laminating element 32 can have a plurality of holes, in at least one row, cut out of the layer in a predetermined pattern that can correspond to the other layers of the septum seal 30, as well as the holes 24 in the cartridge cover 16, all of which correlate to the points of contact from the probes of the diagnostic device during operation. It is contemplated that where more than one laminating element is used in the septum seal 30, the two laminating elements can be different materials. It is further contemplated that where more than one laminating element is used in the septum seal 30, the two laminating elements can be the same materials.

In certain embodiments, the septum seal 30 is comprised of a septum layer, a laminating element, a support layer, and a second laminating element.

In certain embodiments, the septum seal 30 is comprised of a septum layer and a double-sided pressure sensitive adhesive tape with carrier. The double sided pressure sensitive adhesive tape with carrier is comprised of a laminating element, a support layer, and a second laminating element. For example, the carrier within the double-sided pressure sensitive adhesive tape is a support layer, and the two adhesive layers within the double-sided pressure sensitive adhesive tape are laminating elements.

In certain embodiments, the septum seal 30 is comprised of a septum layer, a laminating element, and a top seal. The top seal is comprised of a support layer and a laminating element. For example, the barrier layer of the top seal is a support layer.

In certain embodiments, the septum seal 30 is an element of a closed fluidic pathway. In certain embodiments, the diagnostic system 10 employs a closed fluidic pathway between the diagnostic instrument 12 and the cartridge 14. The closed fluidic pathway provides a pathway where a sample and necessary reagents are withdrawn from the cartridge 14 using a substantially single direction of flow which returns used reagents and other waste materials back to the cartridge 14.

The septum seal 30 is designed to be addressable by a probe in one or more locations during operation of the diagnostic system. In some certain embodiments, the septum seal 30 can have a plurality of probe entry sites (formed from and found on each individual layer of the septum seal 30, as described above). These entry probe sites can be located above various internal fluidic channels, wells, fluidic elements, and reservoirs and can be arranged in a plurality of patterns according to cartridge configuration and design.

The septum seal 30 is designed to form fluidic connections between cartridge 14 and diagnostic instrument 12 when a probe pierces the septum seal 30. As used herein, to pierce is to penetrate through, or make a through hole, or to cut through, or to tear though the septum layer such that the probe is seal by the septum layer, and then self-seals or reseals when probe is removed. A pierced site is re-usable. The septum seal 30 can form a secure fluid or air passageway between the instrument 12 and cartridge 14 using a probe 128 (see FIG. 12).

The septum seal 30 is designed to connect cartridge fluidic elements to atmosphere or ambient by puncture. As used herein, to puncture is to perforate or to make a through hole in the support layer where the hole is irreversibly formed or permanently opened using a probe. Some of these sites may act as vents, which allow ingress of atmospheric air if under vacuum or allow egress of air if under pressure. Some of these sites allow a probe to address a layer beneath the septum seal 30 without piercing the septum layer 31. There can be at least one, at least two, or a plurality of vents and they can be arranged in various configurations according to a predetermined probe pattern of the corresponding diagnostic instrument. For example, vent configurations can be varied on each layer of the septum seal 30 depending on the configuration of the cartridge and the motion path of the probes.

As described above, the individual layers of the multi-layer septum seal 30 can be pre-formed into separate layers before being combined into the septum seal. Each of the pre-formed layers can be made from materials that can be sized and formed by conventional die cutting or laser cutting methods. The patterning of the probe sites and vents of the septum seal 30 may be accomplished using conventional die cutting or laser cutting methods. Construction of the septum seal 30 may be accomplished using a conventional rotary press.

FIG. 4B provides an exploded perspective view of an embodiment of a septum seal 30 on a cartridge body 18. The septum seal 30 can be comprised of four layers with corresponding pierceable sites and puncturable sites: a septum layer, a support layer, and two laminating elements. It is contemplated that all the layers of the septum seal 30 can have the same length and width, for example, about 0.5 inches by 5.0 inches, about 0.6 inches by 4.0 inches, about 0.7 inches by 4.5 inches and about 0.8 inches by 5.0 inches. In an exemplary embodiment all layers can have the same length and width of about 0.770 inches by 4.943 inches. It is contemplated that the length and width of the septum seal 30 correspond to the top surface of the cartridge 14.

In another embodiment, the septum layer 31 can be made of 0.031 inch thick silicone rubber with hardness of 30 Durometer (Shore A). The septum layer 31 can have 13 vents to enable ingress or egress of atmospheric air. The diameter of the vents is greater than the diameter of the probe. For proper operation, the septum layer 31 as part of the septum seal 30 is not tensioned or stretched. Unwanted tensioning of the septum layer 31 may result in the pierced site not re-sealing or not self-sealing after probe withdrawal.

In still another embodiment, a support layer 33 can be joined to the septum layer 31 using a laminating element 32. The laminating element 32 can be a double-sided pressure sensitive tape such as Dielectric Polymers NT-1020. The laminating element 32 has through holes for each probe entry location so as to avoid adhesive contact with the probe 128. The diameter of the through holes is greater than the diameter of the probe 128. The laminating element 32 forms a tight seal between the septum layer 31 and support layer 33. The laminating element 32 has high peal strength to silicone rubber, and therefore the silicone rubber does not require surface modification such as corona or plasma treatment. The support layer 33 can be made from 2 mil thick aluminum foil. The support layer 33 has 34 through holes which enable the probe to address layers and features under the septum seal 30. The diameter of the through holes is greater than the diameter of the probe. The support layer 33 is joined to the cartridge 14 with a second laminating element 32. The second laminating element 32 can be a double sided pressure sensitive tape such as Dielectric Polymers NT-1020. The laminating element 32 has through holes for each probe entry location so as to avoid adhesive from contacting the probe. The diameter of the through holes is greater than the diameter of the probe. The laminating element 32 forms a tight seal between the support layer 33 and the cartridge 14. In this embodiment, the laminating elements 32 have the same through hole pattern. The register of possible probe entry locations fall along two lines due to the two probe axes of motion of the diagnostic instrument used in this embodiment.

It is contemplated that the register of possible probe entry locations can fall along one line or along two lines or more lines depending on the configuration of the diagnostic instrument 12 and the number of probes incorporated for use in the diagnostic instrument 12. Thus, it is contemplated that more or fewer lines of register sites may be used according to the design and function of the cartridge 14 and the diagnostic instrument 12 with which it functions.

Blood Collection Tube Mount.

Figure 5A:
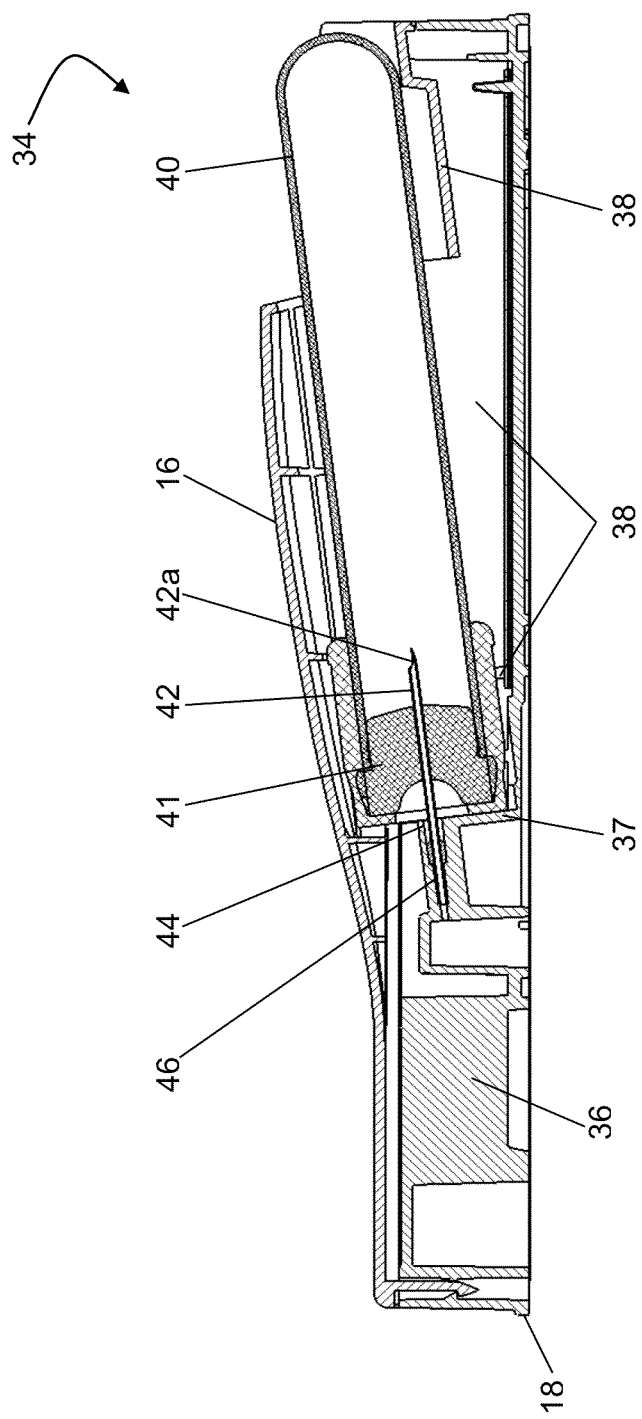
FIG. 5A is a cross-section of a blood collection tube mount of an embodiment.

In various embodiments, the cartridge body 18 is designed to accommodate the mounting of an industry standard blood collection tube (i.e., VACUTAINER®), or similar blood collection tube 40, which can connect to a fluidic pathway of the diagnostic system. The configuration of the blood collection tube mount 34 as described herein promotes the extraction of a majority of the blood contained within the blood collection tube 40 ensuring that the blood is accessible for extraction from the tube and processing while maintaining a low profile within the instrument and/or disposable device. In FIG. 5A, a cross section of an embodiment is shown, having a framework 36 that can be formed as part of the cartridge body 18 out of injection molded or machined plastic or other material(s) of appropriate physical and chemical characteristics as the remaining portions of the cartridge body 18. The blood collection tube mount 34 is also formed in part by the cartridge cover 16, where the domed region of the cover 16 assists in guiding the blood collection tube 40 into place. The cover 16 also assists in securing the blood collection tube in place after insertion. The framework 36 incorporates structures that create supports 38 and guide features 38 to mount and hold a blood collection tube 40 at an angle, between, for example, the horizontal and 45° from horizontal, which facilitates extraction of a predetermined minimum amount of blood from said tube.

The blood collection tube mount 34 is designed to facilitate a connection of the standard blood collection tube to a fluidic pathway(s), such as, for example, of a diagnostic instrument. The blood collection tube mount 34 is designed to allow the extraction of a majority of the blood within the blood collection tube 40. This design provides a low profile combination of the blood tube positioning to maintain minimal vertical space used in the overall cartridge design.

In certain embodiments, the blood tube mounting system or tube mount 34 can be configured to hold a blood collection tube 40 to increase blood extraction from the tube. For example, in certain embodiments, the blood tube mounting system 34 has an angle sufficient to facilitate blood extraction from the tube 40, wherein the angle can range from about less than 90° to about 0° from the horizontal. In other embodiments, the angle can range from about 45° to 0° from the horizontal. In other embodiments, the angle can range from less than 90° to about 45°, from about 45° to about 0°, from about 30° to about 0°, from about 20° to about 0°, from about 10° to about 0°, from about 7° to about 0°, from about 45° to about 20°, from about 45° to about 15°, from about 45° to about 10°, from about 35° to about 15°, from about 35° to about 10°, from about 35° to about 5°, from about 25° to about 15°, from about 25° to about 10°, from about 25° to about 5°, from about 15° to about 10°, from about 15° to about 5°, from about 10° to about 5°, from about 10° to about 7°, or from about 7° to about 5°, or from about 5° to about 0° from the horizontal. In still other embodiments, the angle can be about 45°, about 30°, about 25°, about 20°, about 15°, about 10°, about 8°, about 7°, about 6°, about 5°, about 0° from the horizontal. By way of a non-limiting example, the position at 7° can minimize the special profile of the blood tube-cartridge arrangement, preserving space in the diagnostic instrument 12 and cartridge 14.

This design configuration also can be adapted or designed to accommodate different device and instrument configurations depending on use, function and manufacturing needs and costs. This configuration can be advantageous over existing designs which have a blood tube arranged at an angle of less than 90° but that still may require tipping or additional maneuvering to get the blood out, resulting in excess dead volume due to the larger angle from the horizon (e.g., the higher the angle from the horizon, the more dead volume in the blood tube).

The blood collection tube mount 34 may further be configured to hold a blood collection tube 40 at a desired angle using ribs or other support structures 38 which constrain the tube axially along the desired angle. Certain features may be incorporated into the blood collection tube mount 34 to prevent or inhibit removal of a blood collection tube 40 after insertion into the blood collection tube mount 34, such as, for example, a shroud or tang (not depicted) may be molded in the cartridge cover 16 that inhibits gripping the blood tube 40.

In certain embodiments, the blood collection tube mount 34 can be configured to provide an indication to the user that the blood collection tube 40 is properly seated into the blood collection tube mount 34. For example, a wall 37 of the framework 36 molded into the cartridge body 18 can provide a positive stop for the blood collection tube 40 as well as provide feedback to the user that the tube 40 is fully inserted. Other indications may include, for example, a user feeling a slight pop or click after reaching a designated location in the blood collection tube mount 34 or looking through a viewing window in the cartridge cover 16 for the indication. The framework 36 can also include features that can prevent, inhibit and/or deter extraction of a blood collection tube 40 after insertion onto the framework, such as a tang (not depicted).

In certain embodiments, the blood collection tube mount 34 can be configured to guide a blood collection tube 40 onto at least one needle 42 to establish fluidic communication, such as, for example, with a diagnostic instrument 12. The guide features 38 can also facilitate the piercing of the desired portion of the blood collection tube's septum 41 by physically constraining the radial motion of the tube 40. The at least one needle 42 can be mounted for insertion through the septum 41 of a blood of a blood collection tube 40, which would facilitate, establish and maintain the fluidic connections between the needle(s) 42, 43 and a diagnostic instrument 12. In some embodiments, the blood collection tube mount 34 can have a first needle 42 and a second needle 43, such as that depicted in FIG. 5B.

The mounting of the needles 42, 43 to the framework 36 can establish connections between fluidic pathways 46 molded into the framework and the fluidic channels of the needles. Alternately, the fluidic pathways may be separate items such as tubes with the needles directly or indirectly affixed thereto where the framework provides mounting for the needle/tube combinations (not depicted). The configuration of the at least one needle 42, 43 is designed to prevent or minimize undesired communication of gasses between the needles during blood extraction. The blood collection tube mount 34 can be configured to use a pressure differential between the inside of a blood collection tube 40 and fluidic pathways 46 as the means to extract blood from the blood collection tube 40.

Figure 5B:
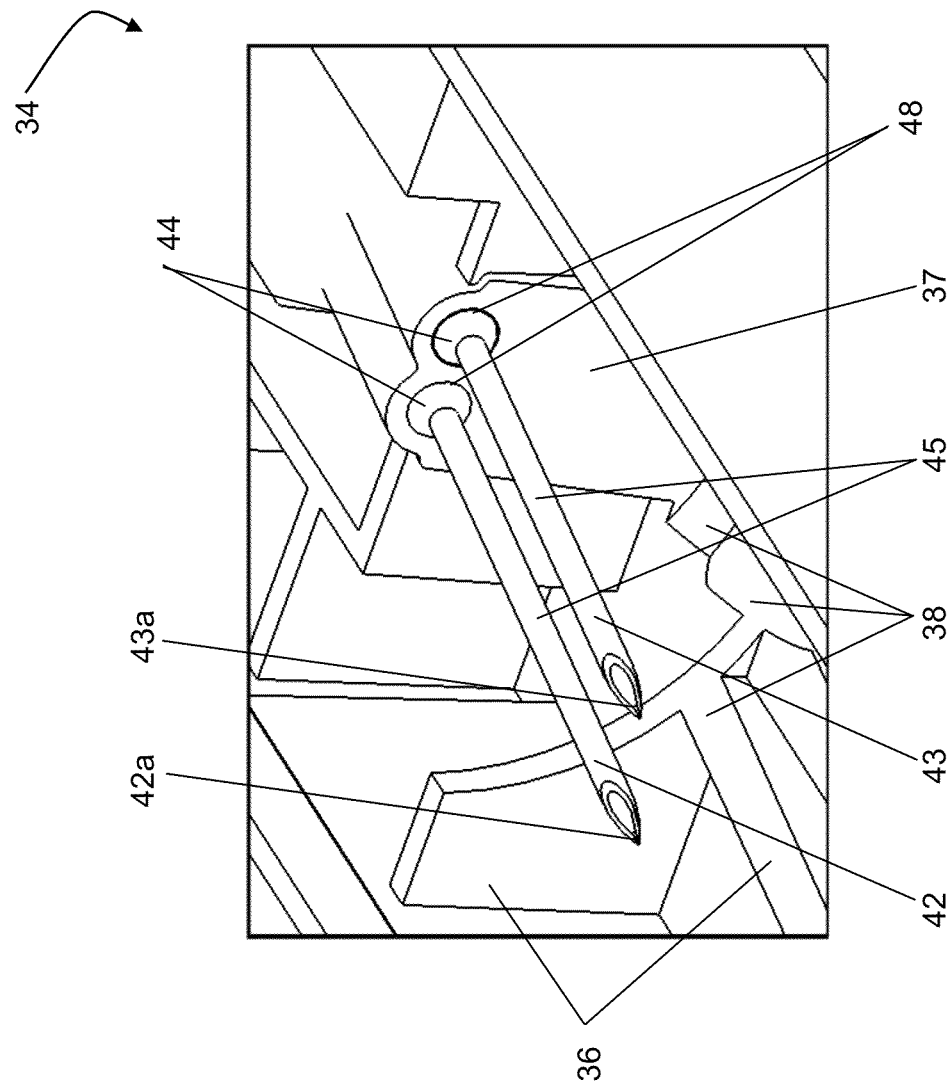
FIG. 5B is a perspective view of a portion of a blood collection tube mount of an embodiment.

To facilitate a secure connection, the first and second needles 42, 43 can be incorporated into the blood collection tube mount 34 by being fitted into at least one designated recess 48 per needle configured to receive one end of a needle. The first and second needles 42, 43 can be permanently attached to the framework 36 so that the exterior surface of the first and second needles 42, 43 are sealed airtight to the framework 36 by means of an adhesive, gasket or other seal, or by insert molding the needles into the framework 36. For example, FIG. 5B illustrates the first and second needles 42, 43 sealed with an adhesive 44 to the framework 36, in an exemplary embodiment. Examples of suitable adhesives include, but are not limited to, an epoxy resin, acrylic cements, silicones, Loctite 3924, and hot-melt adhesives. The adhesive 44 may be set with a heat treatment or cured with a UV light. It is contemplated that the at least one recess 48 may be designed to snuggly fit the at least one needle 42, 43 so that the need for an adhesive is not necessary. It is further contemplated that any combination of the fitted size of the recess and an adhesive may be used to secure the needle.

In an embodiment where two needles are present, the first needle 42 can be mounted such that its terminal end 42a is physically separated from, and not below, the terminal end 43a of the second needle 43 within the tube 40 such that air introduced into the tube to pressurize the tube does not communicate with the second needle 43 causing an unwanted reduction in the flow of blood out of the tube 40. Thus, the terminal end of the second needle 43a is not above the terminal end of the first needle 42a, as the first needle is mounted to the framework 36 on a level above that of the second needle 43. In other words, the first needle 42 protrudes outward from the framework farther than the second needle 43 protrudes from the framework 36.

In the case of a positively pressurized blood collection tube 40, the needle by which a pressure differential is established can be mounted in a position where it will not easily communicate gasses with the needle used for blood extraction assuming they are separate entities. Thus, the needle by which a pressure differential is established is mounted such that its terminal end is physically separated from, and not below, the terminal end of the needle used for blood extraction.

Alternatively, in the case of a negatively pressurized blood collection tube, the needle by through which blood is extracted can be mounted in a position where it will not easily communicate gasses with the needle used for pressure normalization assuming they are separate entities. Thus, the needle by which blood is extracted can be mounted such that its terminal end is physically separated from, and not above, the terminal end of the needle used for pressure normalization.

A lubricant 45, such as, for example, a silicone oil, poly(p-xylylene) polymers, parylene, or polyglycol, may be applied to the exterior surface of the needles 42, 43 during assembly to reduce the force needed to pierce the septum 41 of a blood collection tube 40. Needles that are pre-coated with a lubricant can also be used. The lubricant may also assist in properly seating the blood collection tube 40 on the needles 42, 43 facilitating the needles piercing the septum 41 fully and in the desired septum location.

In embodiments where the configuration includes only one needle, rotation and viewing of a blood collection tube surface is permitted for reading of data from a surface of a blood collection tube after the blood collection tube is inserted. In such an embodiment, the framework may include features that allow automated turning of the tube to permit automated reading of text or other content (for example, barcodes or patient identification labels) off the tube.

Blood Filtration Module.

Figure 6:
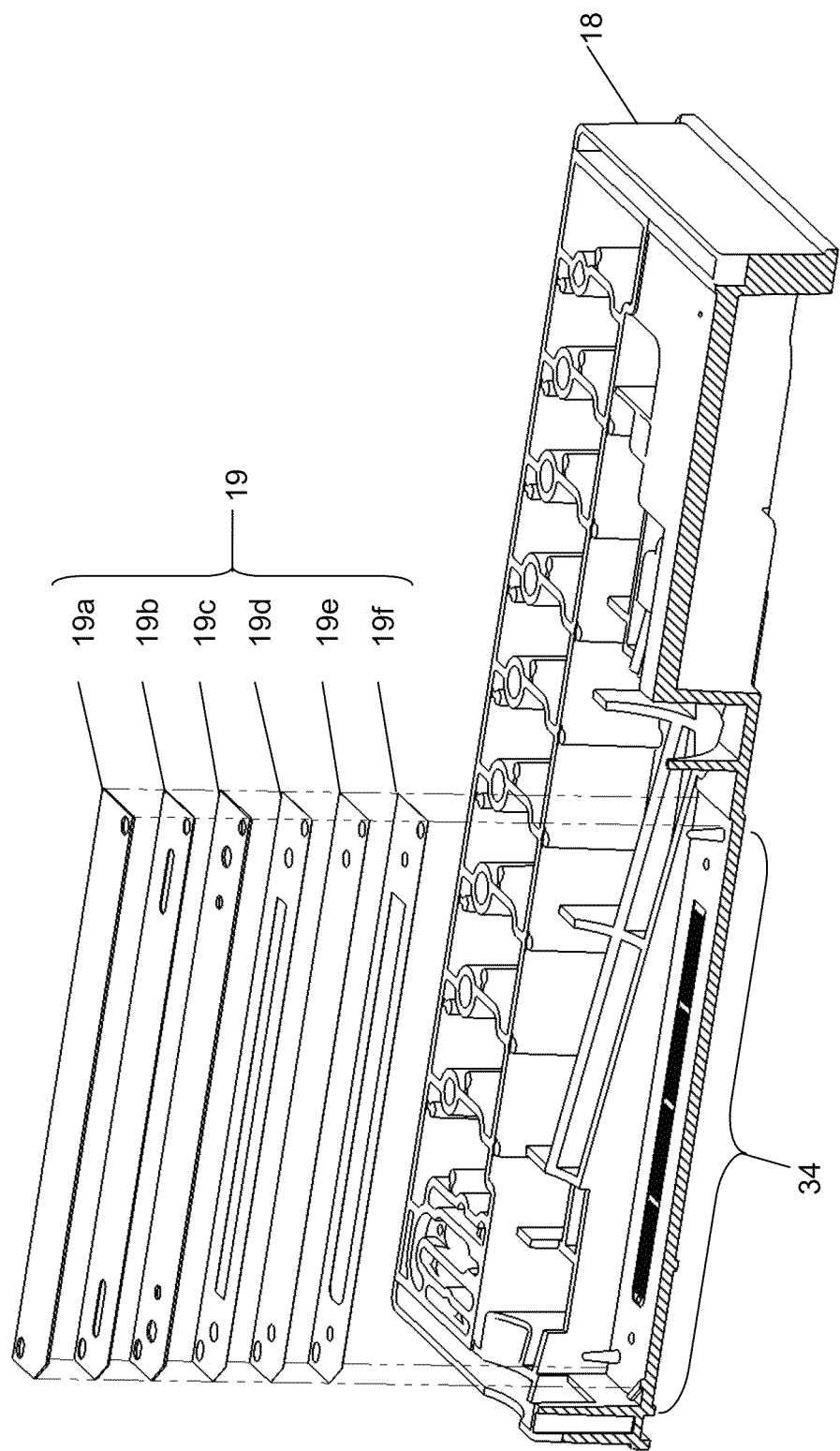
FIG. 6 is an exploded view of a blood filtration module and a cartridge of an embodiment.

For some diagnostic applications, analysis of plasma from blood is desired, for example, analysis using a diagnostics system. Plasma is typically obtained by centrifuging whole blood samples. The present disclosure provides a diagnostic system that obtains plasma from whole blood samples by using a specialized filtration module 19 (See, e.g., FIG. 6) that allows the separation of the plasma from the whole blood sample. FIG. 6 provides an exploded view of the multiple layers comprising an embodiment of a blood filtration module for use in a cartridge. FIG. 6 also illustrates the relationship of the blood filtration module 19 to the cartridge body 18 and where the blood filtration module 19 will sit in the body 18 adjacent to the blood collection tube mount 34. The multiple layers that can comprise the blood filtration module are provided as one embodiment and each are layered 19a-19f. Examples of suitable filtration modules are described in U.S. Provisional Patent Application No. 61/565,253 and co-pending International PCT Application No. PCT/US2012/067041, each herein incorporated by reference in its entirety.

In some embodiments, the blood filtration process generally begins with whole blood that is drawn into the cartridge by a pump of the diagnostic instrument via pressurization of the blood collection tube 40 through the longer of two needles as described above. As air is forced into the blood collection tube, blood within the tube escapes through the shorter needle and travels to the blood filter 19 through a fluidic pathway formed within the cartridge body 18. A first probe of the diagnostic instrument pierces a plasma cache fill vent in order for the plasma cache (e.g., shown in FIG. 7A as sample reservoir 52) to be able to receive the filtered plasma. Next, a waste probe of the diagnostic instrument pierces the septum seal at a predetermined location. Software controls the motion assembly movements, including where the probes contact the cartridge. During this time, the first probe pierces a first waste location and remains there for the duration of the blood filtration. An air-tight connection is not made by the foil in the first waste location, so air freely travels into or out of the first probe (depending on the pump's cycle).

As blood flows across the filter in a single directional flow (from right to left, for example), plasma flows through the 0.6 µm pores in the filter element of the filtration module. Plasma leaves the bottom of the filtration modules and fills the plasma cache. Retentate (concentrated whole blood) passes over the filter, and is irrevocably lost into a waste area (irrevocable because aspiration from the waste area will aspirate air, not the denser retentate). After the plasma cache is full (as determined by an optical sensor on the bottom of the cartridge), the first probe pierces the pressure release location to vent the blood collection tube to atmospheric pressure. Next the cache channel vent is pierced and the plasma is sent down the cache channel for metering. After metering, the post filter cache vent is pierced to prevent additional liquid from entering the cache from the filter, which if allowed, may block atmospheric venting of the cache channel.

Metering Biological Sample.

Aliquoting a sample into multiple volumes is a typical component of clinical testing, such as when conducting a panel of assays or when conducting replicate measurements. The diagnostic system includes components of both the diagnostic instrument and cartridge that can cooperate to divide a biological sample, such as filtered plasma, into specific volume aliquots for further processing, such as with assay reagents. The method results in a reproducible system of metering that is precise, efficient, and permits the sample to remain in the cartridge during the metering. These methods and devices can eliminate the risk of aliquoting errors common with other methods such as manual pipetting and manual steps. Manual steps can be slow, costly, and prone to human error. The methods and devices of the present disclosure are applicable to nearly any type of liquid including, but not limited to, blood, plasma, and urine and in some embodiments, the sample can be from a common source.

The metering methods described herein do not require additional user input after the cartridge is introduced into the diagnostic system. Once the cartridge is introduced into the diagnostic instrument by the user, the diagnostic test cycle begins and as it proceeds it is monitored internally by the software systems of the diagnostic system. Thus, upon insertion, the diagnostic instrument first identifies the cartridge and the diagnostic test to be completed within the present cycle. The appropriate test sequence is initiated by the software and the timing, speed, and duration of all subsequent fluid motions are initiated and controlled.

An aliquoting device can be a sub-section of a diagnostic system. Other sub-sections include mechanisms for carrying out an immunoassay such as mixing, incubating, free-bound separation, and readout. The aliquoting mechanism can be directly integrated into a diagnostic system. In some embodiments, it is intended that an aliquoting mechanism uses pre-existing features of the diagnostic system such as an external fluidic system including a pump and other features that will become apparent. It is further intended that an aliquoting method, along with the other immunoassay process steps, may be automated. It is further intended that the aliquoting mechanism derives its accuracy and precision independently of the external fluidic system.

Figure 7A:
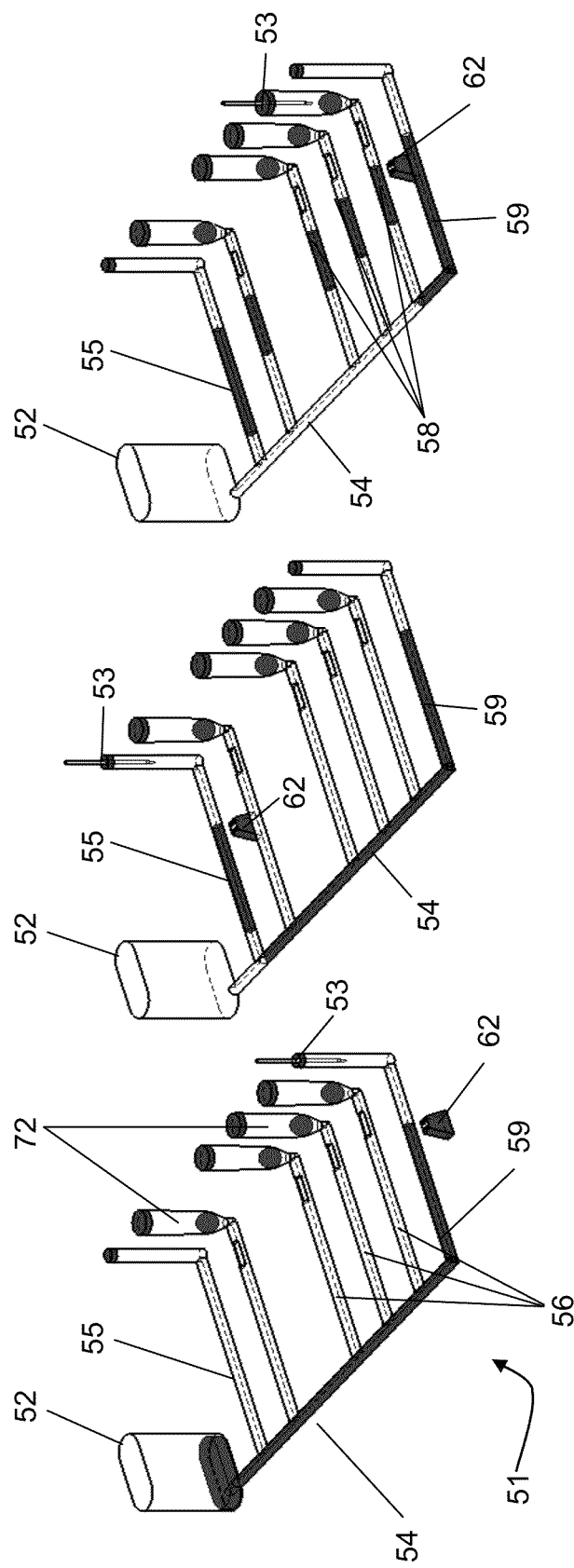
FIG. 7A is an illustration showing aliquoting of a sample in fluidic channels of a cartridge of an embodiment.

In some embodiments, an aliquot method of the presently disclosed diagnostic system can be comprised of three operations which use the features of the aliquoting device. FIG. 7A is an illustration of the fluidic features necessary for an aliquot device intended to produce three aliquot volumes such as of 25 µL. The aliquot device 51 can be a sub-section of a clinical diagnostic instrument. Only those features relevant to the present disclosure are described as it would be apparent to anyone skilled in the art of assay construction what additional features are necessary.

The aliquot method has a precision and accuracy independent of pump accuracy. In this method, a first operation can be to draw sample liquid from the sample reservoir (also referred to as plasma cache) 52 into the primary channel 54. The extent of filling the primary channel 54 is independent of pump accuracy. The second operation can be to empty the remaining sample liquid from the sample reservoir 52 into the secondary channel 55. The second operation is also independent of pump accuracy. The leftover liquid volume is the excess of sample liquid over total aliquot volume (where total aliquot volume is the aliquot volume multiplied by the number of aliquots). The final operation is to draw a segment of liquid from the sample liquid located in the primary channel 54 between receiver channels 56 into a receiver channel 56. The volume of liquid in the primary channel 54 between receiver channels 56 is the aliquot volume. This is done for each receiver channel 56 (the number of which is dependent on the cartridge design and the diagnostic test being run on the cartridge). This operation is also independent of pump accuracy. At the end of the method, all sample liquid that was contained in the sample reservoir 52 is aliquoted into each of the receiver channels 56 and the secondary channel 55.

The aliquot device 51 can accommodate any type of clinical sample such as blood, plasma or urine. In some embodiments of the aliquot device 51, the clinical sample to be aliquoted is located within a sample reservoir 52. The means for locating the sample into the reservoir 52 would be apparent to anyone skilled in the art of assay construction and can be as described herein. The sample reservoir 52 can have a volume ranging from about 125 µL to about 135 µL, about 135 µL to about 150 µL, about 150 µL to about 175 µL, and about 175 µL to about 200 µL. The sample reservoir can have a volume of about 150 µL, about 175 µL, about 200 µL, about 225 µL, or any volume therebetween. In an exemplary embodiment the sample reservoir 52 can have a volume of about 200 µL. The opening of the sample reservoir 52 is located on the top surface of the aliquot device 51 and the sample reservoir 52 is open vented to ambient.

The sample reservoir 52 can be connected to a primary channel 54. The primary channel 54 can have a volume less than the sample reservoir volume. For example, the primary channel 54 can have a volume ranging from about 125 µL to about 135 µL, about 135 µL to about 150 µL, about 150 µL to about 175 µL, and about 175 µL to less than about 200 µL. The primary channel can also have a volume of about 125 µL, about 150 µL, about 175 µL, about 200 µL, or any volume therebetween.

In an exemplary embodiment the primary channel 54 can have a volume of about 150 µL. The primary channel is connected to an end channel 59. The end channel 59 can have a volume of about 20 µL, about 25 µL, about 30 µL, or any volume therebetween. In an exemplary embodiment the end channel 59 can have a volume of about 25 µL. The end channel 59 is connected to a pump connecting port 53. Also connected to the primary channel 54 are three receiver channels 56. The volume of each receiver channel 56 is designed to be greater than the aliquot volume 58 and can be equal to about 50 µL, about 75 µL, about 100 µL, or any volume therebetween. In an exemplary embodiment each receiver channel 56 can have a volume of about 75 µL.

Also connected to the primary channel 54 is a secondary channel 55. External to the aliquot device 51 can be a sensor 62 to detect when a liquid front reaches the primary channel fill mark (not shown). The sensor 62 can be used to detect when a liquid front reaches the secondary channel fill mark (not shown). The volume of the secondary channel 55, based on the fill mark, is designed to be greater than the difference in volume between the sample reservoir 52 and primary channel 54 volume. The secondary channel 55 can have a volume ranging from about 125 µL to about 135 µL, about 135 µL to about 150 µL, about 150 µL to about 175 µL, and about 175 µL to less than about 200 µL. For example, the secondary channel can have a volume of about 125 µL, about 150 µL, about 175 µL, about 200 µL, or any volume therebetween. In an exemplary embodiment the secondary channel 55 can have a volume of about 150 µL.

The secondary channel 55 and each receiver channel 56 are connected to pump connecting ports 53. The number of pump connecting ports can vary depending on the configuration of the cartridge 14, and may range from 5 to 7 pump connecting ports. For example, in an embodiment, there may be a total of 5 pump connecting ports. The pump connecting ports 53 are normally closed. The fluidic channels, i.e., secondary channel 55, receiver channels 56, and end channel 59, are in fluidic communication with a pumping mechanism through the pump connecting ports 53. Fluid motion between the fluidic channels necessary for the aliquot method can be conducted by applying vacuum pressure from a pump (not depicted). The aliquot volume 58 can be defined as the volume between adjacent receiver channels 56. The number of aliquots can be defined as the number of receiver channels 56.

The sample volume does not require a precise or accurate fill in the sample reservoir 52 but only that its volume exceeds a minimum. For example, the minimum sample reservoir fill can be about 75 µL, about 100 µL, about 125 µL, or any volume therebetween. In an exemplary embodiment the, the minimum sample reservoir fill volume can be about 100 µL.

FIG. 7A illustrates an embodiment of an aliquot method. As briefly discussed above, the aliquot method is comprised of three operations which use the fluidic features of the aliquot device 51 described above. The precision and accuracy of the method is independent of pump displacement, as will become apparent in a description of the method. A method of aliquoting a sample comprises drawing a sample liquid from a sample reservoir 52 into a primary channel 54. This fluid motion is driven by vacuum generated inside the channel due to a pump being connected the end channel pump connecting port 53. During this operation, the other connecting ports are closed. When the liquid front of the sample reaches the primary channel fill mark 57, the sensor 62 which addresses the aliquot device 51, communicates to the pump to stop and release from the end channel pump connecting port 53. The extent of filling the primary channel 54 is independent of pump accuracy. The extent of filling the primary channel 54 depends on the geometry/volume of the primary channel 54. In one embodiment, the fluidic features can be formed by injection molding fabrication and can be replicated with high precision and accuracy.

The second operation is emptying the remaining or leftover sample liquid from the sample reservoir 52 into the secondary channel 55. This fluid motion is driven by vacuum generated inside the secondary channel 55 due to a pump being connected to the secondary channel pump connecting port 53. During this operation, the other connecting ports are closed. The second operation is also independent of pump accuracy. When the liquid front of the sample reaches the secondary channel fill mark 60, the sensor 62 which addresses the aliquot device 51, communicates to the pump to stop and release from the secondary channel pump connecting port 53.

The final operation is drawing each aliquot volume into a receiver channel 56. This is conducted sequentially and three times for each of the three receiver channels 56, for example, in an embodiment with five secondary channel pump connecting ports 53. The sequence of drawing aliquot volumes into a receiving channel 56 is conducted in order and starting with the aliquot volume closest to the secondary channel 55 (e.g., from left to right in FIG. 7A). This fluid motion is driven by vacuum generated inside each receiver channel 56 due to a pump being connected to the receiver channel pump connecting port 53. At the end of the method, all sample liquid that was previously contained in the sample reservoir 52 is aliquoted into each of the receiver channels 56 and the secondary channel 55.

The aliquot device 51 is adaptable by increasing or decreasing the number of aliquots accommodated on an aliquot device 51. For example, the number of aliquots can be greater than or equal to (≥1), or less than or equal to the sample volume in the sample reservoir 52 divided by the aliquot volume.

The aliquot device 51 is further adaptable by increasing or decreasing the aliquot volume deliverable within an aliquot device 51. The aliquot volume is driven by the available sample volume and the number of aliquots. For example, an aliquot volume may be less than or equal to the sample volume divided by the number of aliquots.

The aliquot device 51 is further adaptable by aliquoting the sample equally into multiple volumes. For example, the aliquot volume may be the same within an aliquot device 51.

The aliquot device 51 is further adaptable by accommodating different aliquot volumes within a single aliquot device 51. For example, there may be two or more different aliquot volumes within an aliquot device 51.

The aliquot device and method avoid using pump displacement as a mechanism which determines aliquot volume and avoid using any mechanism for aliquoting a sample where pump accuracy and precision drive/determine the accuracy and precision of the aliquoting method. The accuracy and precision of the aliquoting method is independent of pump accuracy and precision.

Figure 8A:
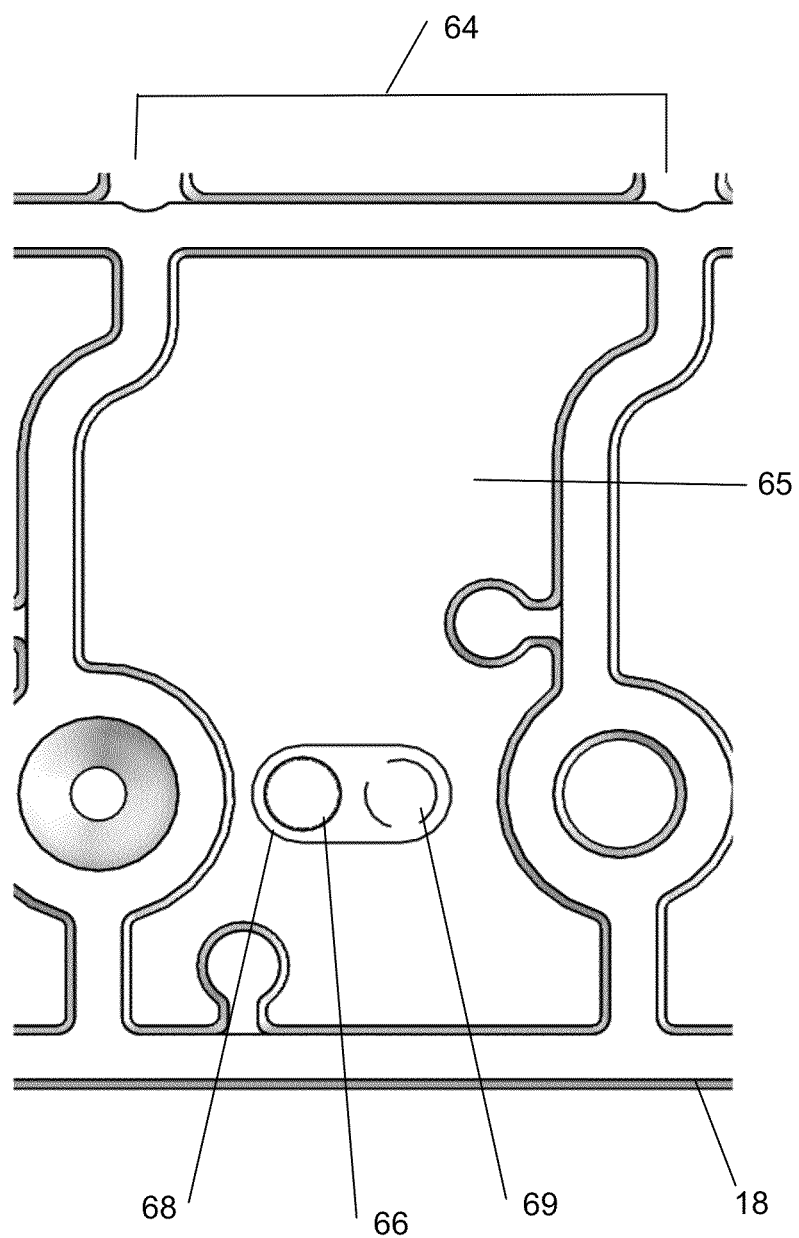
FIG. 8A is a top perspective view of a portion of a cartridge illustrating a reagent handling station (RHS) of a cartridge of an embodiment.
Figure 8B:
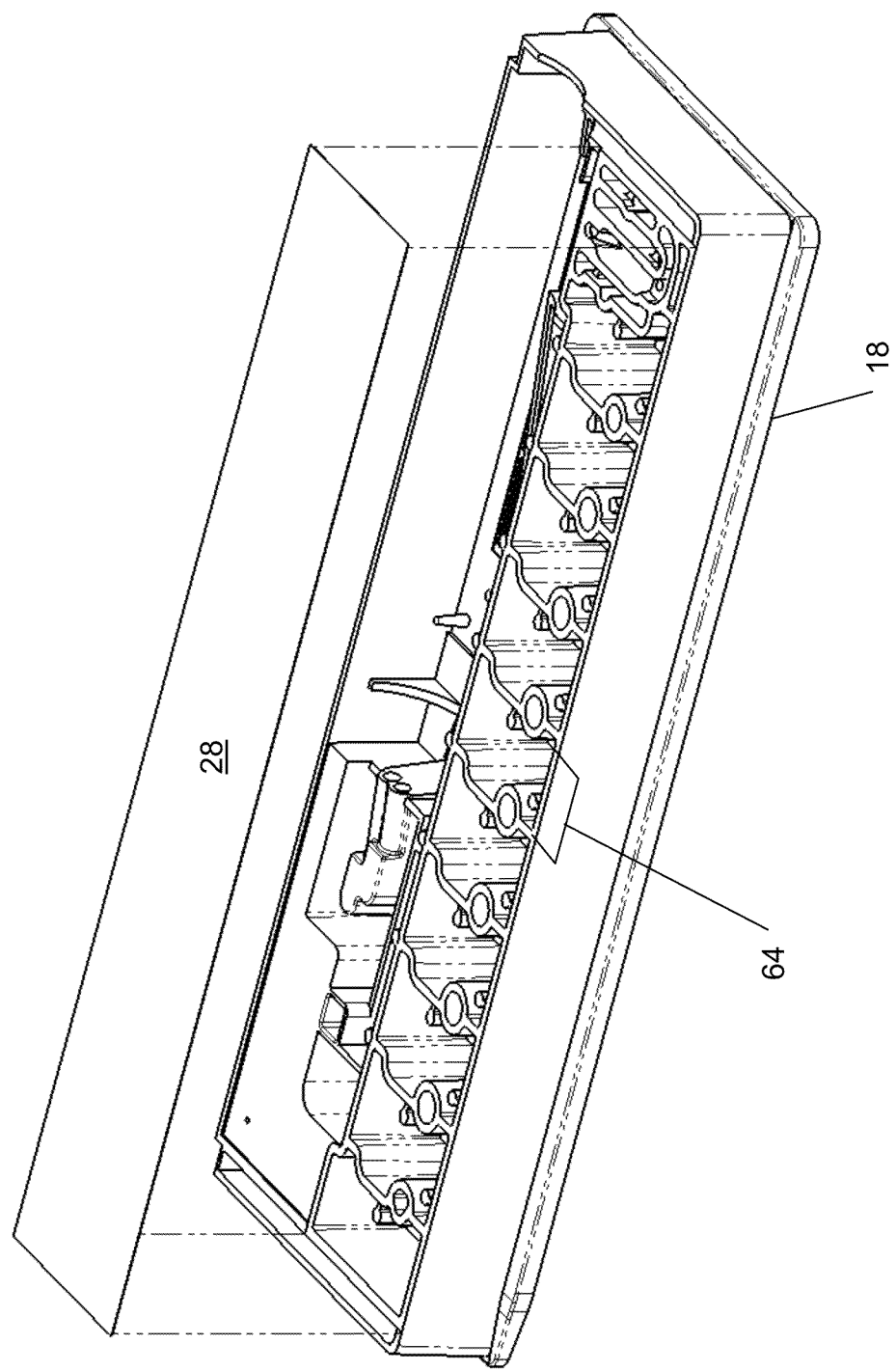
FIG. 8B is an exploded perspective view of a cartridge with multiple RHSs and a top seal of an embodiment.

Reagent Handling Stations (RHS). The diagnostic system provides a unique liquid storage well, or a reagent handling station (RHS), which can be used for storage of reagents, as a probe wash station, and as a waste containment area on a cartridge during processing of a diagnostic test. The RHS 64 of FIGS. 8A and 8B is formed out of the cartridge 14 and plays a role in the fluidic connections between the cartridge 14 and the diagnostic instrument 12. FIG. 8A illustrates a single RHS 64 including probe entry sites 68, 69 of a top seal where the top seal is not depicted around the probe entry sites, and a pocket 66. FIG. 8B is an exploded perspective view illustrating the spatial relationship between the cartridge and the top seal 28. Multiple RHS are visible, where only one is labeled.

In general, a RHS 64 is made of a reservoir 65 that has low dead volume and is comprised of walls with low moisture vapor transmission rate (MVTR) due to the thickness and material of the walls. The walls of the reservoir 65 can be formed from the cartridge body and be of the same material such as Cyclic Olefin Copolymer (COC). Liquid drawn from this reservoir washes the first probe's exterior and serves as a source of carrier fluid for the transport of reagents to the instrument detection cell. The RHS reservoir 65 has a depth greater than the length of a probe 128 of the diagnostic instrument 12, which allows for the reduction in the dead volume. The size and shape of the RHS reservoir 65 can vary as long as it can be sealed, e.g., with a foil seal, and there is enough space in the top to vent the liquids to air prior to aspiration.

The depth of the containment pocket (including the probe pocket) must be shorter than the sample probe. In particular, a pocket 66 with a specific geometry is present in the bottom of a RHS reservoir 65 which provides the reduced dead volume by facilitating contact with increased fluids by the probe 128 within the reservoir pocket area 66. For example, the RHS reservoir 65 can have a depth of about 0.40 in., about 0.45 in., or about 0.50 in., or depths therebetween, including, about 0.42 in., about 0.43 in., about 0.46 in., about 0.47 in., about 0.48 in. The RHS reservoir 65 can have a total volume of about 1.5 mL, about 1.7 mL, about 2.0 mL, or total volumes therebetween, such as about 1.6 mL and 1.9 mL. In an exemplary embodiment, a 0.0625 in. diameter and a 0.041 in. deep well at the bottom of the RHS reservoir 65 enables a more complete removal of liquids from the well (minimizing dead volume).

The RHS 64 further comprises a multi-layered foil heat seal, i.e., top seal 28, such as that previously described herein. The top seal 28 can be heat sealed to the top of the RHS reservoir 65. The top seal 28 functions to help with cleaning the exterior of the probe as it traverses the seal, acting similar to a squeegee. The seal facilitates probe cleaning and can reduce carryover between readings during operation. The seal further facilitates the introduction of air to liquid transitions during liquid draws. The seal is comprised of a specially developed foil seal designed to heat seal to thin walls of COC plastic in order to keep the moisture vapor transmission rate low and maintain a minimum size of the device. The thin walls and the seal also help to maintain thermal uniformity. The top seal 28 can be made of a foil seal such as Winpak LTD-WINCARE DF10HJ712A Heat Sealing Foil.

The area of a RHS reservoir 65 is large enough to allow for at least one probe entry site, for example two probes from a diagnostic instrument 12. In an exemplary embodiment, the RHS reservoir 65 diameter was selected to allow for a ±0.013 in. positioning error of the sample probe before it strikes the edge of the probe pocket 66. The probe entry sites 68, 69 serve to vent the reservoirs, and therefore the cartridge, to the atmosphere, which is important for the fluidic functions of the cartridge. Evaporation can be minimized through both the seal and pierced holes in the seal. The cartridge can withstand changes in atmospheric pressure when sealed.

The pocket 66 is sufficiently large enough to allow access of the probe and allow for puncturing a separate hole 69 for venting to atmosphere. Vent 69 requires an air gap beneath the seal to prevent liquid from exiting through the opening. The aspiration location 68 can be under a septum to reduce salt accumulation on the probe 128. The septum, i.e., septum seal 30, can provide squeegee cleaning action on the sample probe when removed from the aspiration location 68 up through the septum. In some embodiments, a septum is a 0.032 inch thick rubber material (e.g., 30 durometer Silicone).

When a probe 128 from a diagnostic instrument enters the RHS reservoir 65 and draws the reagents into the probe 128, the reagents can act as a cleaning agent. The fluid motion along the probe draws particles on both the outside and inside surfaces of the probe up into the diagnostic instrument and eventually to a waste containment area. The introduction of air bubbles by moving the diagnostic instrument probe up and down in the vented reagent handling station 64 allows the introduction of small bubbles. These bubbles aid in the cleaning of the probe surfaces by increasing the scrubbing action along the surfaces. This cleaning decreases the carryover between reads.

In certain embodiments, liquids drawn into the diagnostic instrument are returned to the cartridge before the run is complete. To minimize the size of the cartridge, the RHS 64 can be reused as a waste compartment for the previously processed liquids. Capillary action keeps the waste liquid in the cartridge even upon inversion of the device despite the probe-created holes in the foil or plastic. For example, a 0.0355" hole has a capillary pressure equivalent to 0.71 inches of water, which is 1.5× the head pressure from the deepest waste cavity (0.46").

In an embodiment, the volume of the RHS reservoir 65 is 1.7 mL to the top and the fill volume is 1.3 mL. The fill volume should be close to the usable volume. However, the fill volume should not match the total volume as the foil will not properly seal if wet. The 0.062 in. diameter probe pocket 66 enables liquid to drain to the probe 128. In some embodiments, the cartridge 14 material is a Cyclic Olefin Copolymer (COC) because of the low Moisture Vapor Transmission Rate (MVTR). For example the MVTR for Polyplastics TOPAS® 5013, a COC, is 0.00193 g/100 int/day. With such a low MVTR, while some liquid may evaporate during storage, less than 1.2% of liquid reagent will evaporate, in some embodiments. This 0.016 mL evaporation is negligible when considering the fill capacity of the RHS well.

While the present discussion is largely focused on the use of the RHS 64 with assays, it is not meant to be limiting and is only one example for which this RHS 64 can be used. For example, the RHS 64 can have utility in any long term liquid storage on any plastic disposable device.

Mixing and Pre-Incubation Sample Preparation Method.

The diagnostic system provides methods for rehydrating lyophilized reagent pellets, e.g., with a patient sample, while minimizing foaming, producing homogenously mixed sample before an incubation, and positioning the homogeneously mixed sample to an incubation zone similarly located for each assay replicate in order to improve the accuracy and the precision of a clinical assay.

The rehydrating lyophilized pellets contain magnetic beads. Rehydrating a lyophilized pellet with a patient sample causes foaming in the mixture. The foam generated while rehydrating lyophilized pellets can trap the magnetic beads. The foam generated is more variable than the liquid with regard to moving in a fluidic channel. A greater yet unknown amount of foam may be left on the walls of the fluidic channel. This can result in more, and an inconsistent number of, beads to also be left on the walls, and cannot reach the incubation chamber. This can in turn cause an unknown amount of beads from being properly incubated with a patient sample, which can result in inaccurate and imprecise measurements.

Figure 9A:
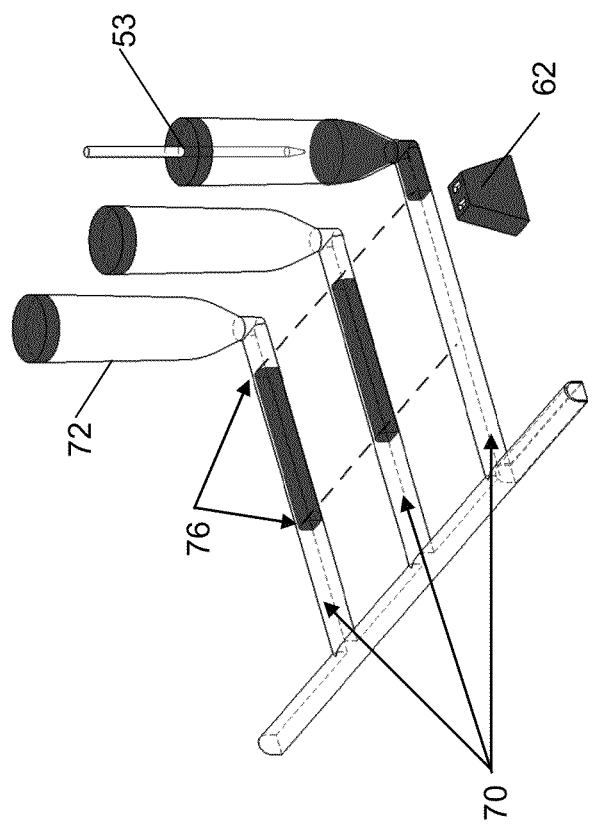
FIG. 9A is an illustration of multiple fluidic channels of a cartridge of an embodiment.

In certain embodiments, the mixing and preparation method can minimize foam during the rehydration of the lyophilized pellets, which minimizes the variability between assay replicates as well as between cartridges, thus improving the precision. This can be accomplished during rehydration of lyophilized pellets by detecting the leading edge of a sample with an optical sensor 62 (FIG. 9A) and, once detected, slowly introducing the sample to the lyophilized pellet. Obtaining a homogeneous sample before the incubation ensures the accuracy and the precision of an assay by allowing the maximum amount of antigen in a patient sample to bind to the reagents. FIG. 9A depicts multiple cartridge assay replicates (CARs) 70, showing the precise positioning of the sample in an incubation zone 76 by using the optical sensor 62 and its ability to detect liquid air transition.

Figure 9B:
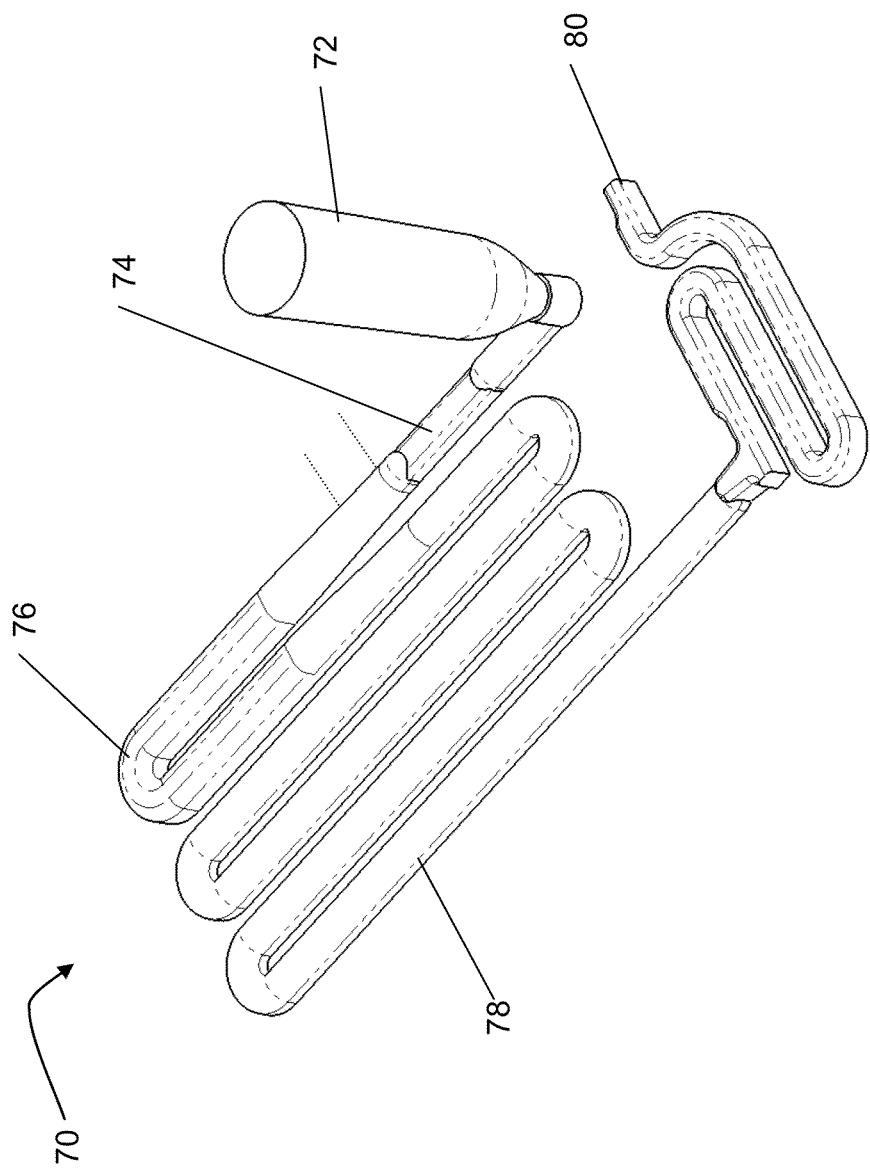
FIG. 9B is an illustration of a single fluidic channel of a cartridge of an embodiment.

Certain embodiments provide a cartridge that can have different geometries in a cartridge assay replicates (CAR) 70 (FIG. 9B). During a back-and-forth fluidic motion within the CAR 70 a homogeneous sample can be obtained before positioning the sample to an incubation zone. Positioning the sample to an identical incubation location for each assay replicate ensures that the sample in each assay replicate gets the same degree of incubation. Certain embodiments provide a diagnostic system that can verify the location of the sample by detecting the leading edge of a sample with the optical sensor 62 before positioning the sample to an incubation zone 76 (FIG. 9A) for each assay replicate 70.

FIGS. 9A and 9B show different components in a single CAR 70 which represents independent channels in a cartridge that can process different tests for the same patient. To minimize foaming during the pellet rehydration, the leading edge of the sample is detected with the optical sensor 62. Once detected, the sample is slowly introduced to the active mix well 72. To obtain the homogeneous sample, the sample is moved back and forth across the active mix well 72 bottom and the bead capture zone 74 in order to have the sample fluid pass through different diameters. Fluids that experience diameter changes during flow result in more homogenous mixtures due to the turbulent flow experienced by the fluid because of the diameter changes.

In one embodiment, the active mix well 72 bottom can have a diameter of 0.045 in., the bead capture zone 74 can have a height of 0.024 in., and the wash channel can have a height of 0.036 in. To ensure that the sample is incubated at the identical location in each channel, the leading edge location of the sample is verified with the optical sensor 62 before positioning the sample to the incubation zone 76.

Figure 9C:
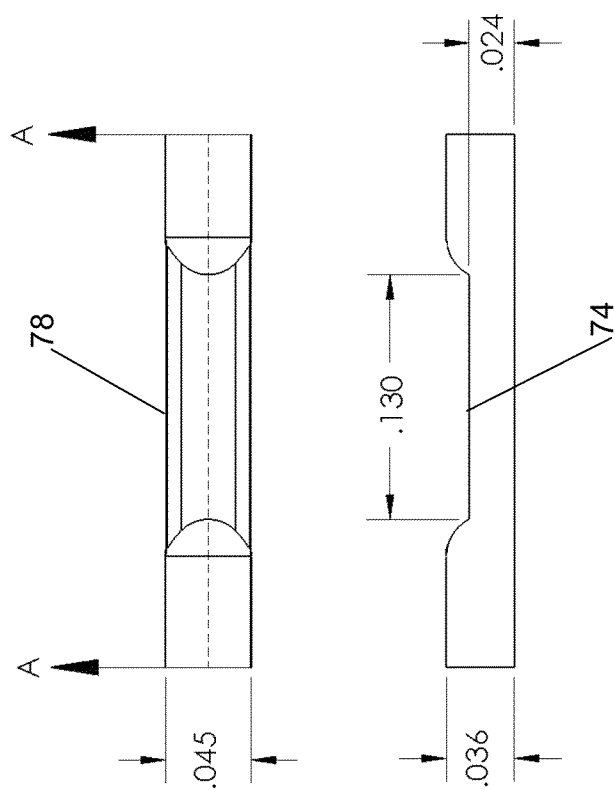
FIG. 9C is an illustration of dimensions of a wash channel and a bead capture zone of a cartridge of an embodiment.

FIG. 9C shows exemplary dimensions at the bead capture zone 74 (top view shows width of channel; bottom view is a cross section, showing the height). The width of the channel is identical to the diameter of the bottom of the active mix well 72. In the embodiment depicted, the maximum height of the bead capture zone 74 can be about 0.024 inch, the maximum height of the wash channel 78 can be about 0.036 inch, and the active mix well bottom diameter can be about 0.045 inch. It is contemplated that the height and well bottom diameter can range in sizes and depths depending on the design and configuration of the diagnostic system and these values are not meant to be limiting.

Figure 10:
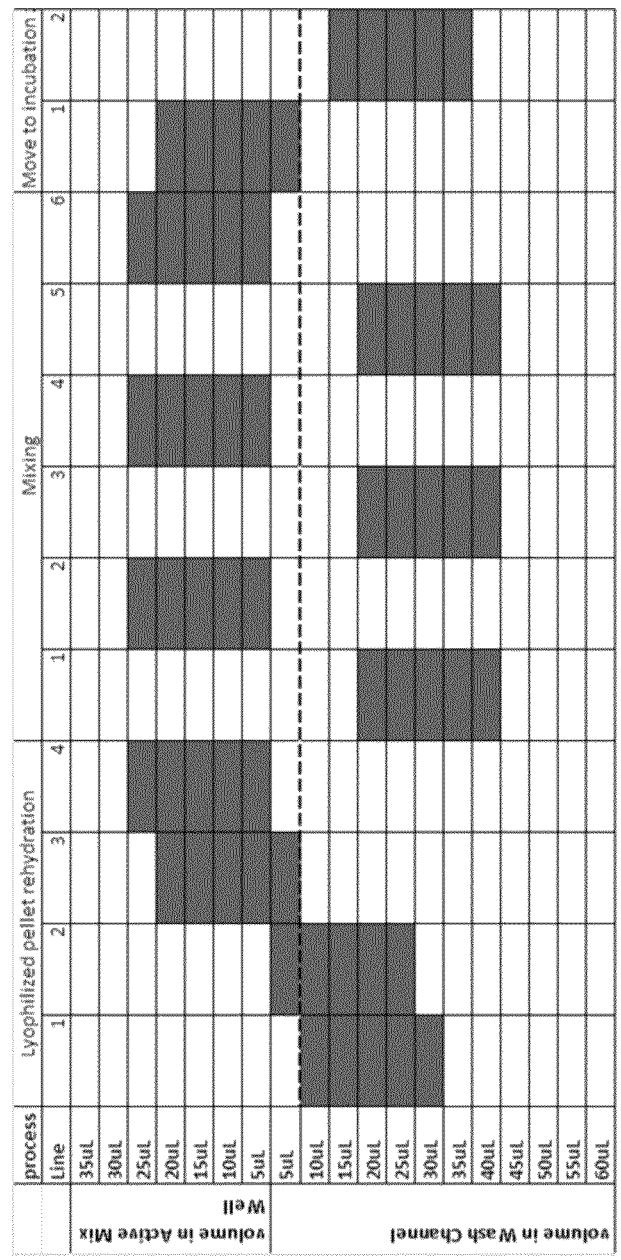
FIG. 10 is a graphical representation of the location of a sample during processing steps of a diagnostic system of an embodiment.

FIG. 10 is a chart of fluidic actions illustrating where a sample (of volume of 25 μl) can be located for each process. The resolution of the fluidic chart is 5 μl. The dotted line in bold between 5 μL and 10 μL in Wash Channel represents the location of Bead Capture Zone. The shaded cells represent the location of a sample (25 μA. There are three operations detailed in the chart that correspond to Tables 1-3 below: Lyophilized pellet rehydration (has 4 steps/"lines"); Mixing (has 6 steps/"lines"); Move to Incubation (has 2 steps/"lines"). The column numbers in the fluidic chart under the operations, correspond to the Step numbers in Tables 1-3 below. For example, during the Mixing operation, the sample (25 μA starts in Wash Channel (15 μl in the wash channel and 10 μl away from the bead capture zone (Step 1 of Mixing process)), and is moved into the Active Mix well with the next step (Step 2 of Mixing process).

Tables 1-3 below show a software playlist that can be used for each objective with a detailed description of each process given below each Table. The CAR components mentioned in the description below are identified in FIGS. 9A and 9B. The location of the patient sample in each process is specified in FIG. 10.

TABLE 1

Procedure for Rehydration of Lyophilized Reagents

| Steps | Procedures |
|---|---|
| 1 | Pump Cycle [150,10,Aspirate,Stop at OS1 (CAR),−100,50] |
| 2 | Pump Displace [5,5,Aspirate,Both] |

TABLE 1-continued

Procedure for Rehydration of Lyophilized Reagents

| Steps | Procedures |
|---|---|
| 3 | Pump Cycle [30,5,Aspirate,Stop at OS1 (CAR),100,50] |
| 4 | Pump Displace [5,5,Aspirate,Both] |

Note:
In the commands above, the first parameter in the parenthesis is the desired volume (in μl) to be pumped and the second numerical value is the flow rate (μL/sec) at which the volume will be pumped.

Step 1 commands a pump to aspirate a sample toward the active mix well until an optical sensor detects the leading edge of the sample (an air to liquid transition detected by a sensor measurement difference sited by the fifth parameter "−100" when the sensor measurement changes by −100 my or more, indicates that air to liquid transition has taken place). Step 2 moves the sample further ensuring that the optical sensor is aligned with the sample fully and not just the transition, which enables to measure the correct reference signal for its next detection (liquid to air). Step 3 commands the pump to aspirate the sample toward and into the active mix well rehydrating the lyophilized reagents pellets with the sample until the optical sensor detects the trailing edge of the sample. Notice that Step 3 uses a flow rate of 5 μL/sec whereas the Line 1 utilizes a flow rate of 10 μL/sec. Step 3 introduces the sample slowly into the active mix well in order to minimize foaming while rehydrating the lyophilized reagent pellets. Step 4 ensures that the optical sensor is aligned with air that follows the sample (channel that had been wet by the sample, but has air now) and takes the correct reference signal for its next detection.

TABLE 2

Procedure for Mixing

| Steps | Procedures |
|---|---|
| 1 | Pump Displace [40,10,Dispense,Both] |
| 2 | Pump Displace [40,40,Aspirate,Both] |
| 3 | Pump Displace [40,10,Dispense,Both] |
| 4 | Pump Displace [40,40,Aspiratee,Both] |
| 5 | Pump Displace [40,10,Dispense,Both] |
| 6 | Pump Displace [40,10,Aspirate,Both] |
| 7 | Delay [5000] (not shown in the fluidic diagram) |

Step 1 commands the pump to dispense a sample into a wash channel such that the trailing edge of the sample moves past the bead capture zone. Step 2 commands the pump to aspirate and to move the sample across the bead capture zone back into the active mix well. Notice that Step 1 moves the sample at a flow rate of 10 μL/sec whereas Step 2 moves the sample at a flow rate of 40 μL/sec. A slower flow rate while moving the sample from the active mix well into the wash channel (Step 1) avoids leaving beads on the active mix well wall. A faster flow rate while moving the sample back into the active mix well promotes a proper mixing.

During the mix cycle, a sample moves between an active mix well 72 and a wash channel 78 across a bead capture zone 74 and experiences changes in the cross sectional area, e.g., from 0.0016 in$^2$ to 0.0011 in$^2$ between the wash channel and the bead capture zone and from 0.0011 in$^2$ to 0.0016 in$^2$ between the bead capture zone and the mix well bottom.

Step 3 and Step 4 repeat the mixing cycle. Step 5 and Step 6 repeat the mixing cycle but differ in that it aspirates the sample back into the active mix well at 10 μL/sec, instead of 40 μL/sec, in order to bring back some of the beads that might have been left in the wash channel during the 40 μL/sec aspiration of previous two mixing cycles.

TABLE 3

Procedure for Positioning the Sample to the Incubation Zone

| Steps | Procedures |
|---|---|
| 1 | Pump Cycle [30,5,Dispense,Stop at OS1 (CAR),−100,50] |
| 2 | Pump Displace [30,5,Dispense,Both] |

Step 1 commands a pump to dispense until an optical sensor detects the leading edge of a sample. Step 2 positions the sample to the incubation zone. Notice that a slow flow rate (5 μL/sec) avoids leaving beads on the active mix well wall.

Method for Detecting Air to Liquid and Liquid to Air Transitions in a Fluidic Channel.

The diagnostic system provides methods for detecting the transition of air to liquid and liquid to air boundaries in a fluidic channel, such as for a diagnostic cartridge. Certain embodiments provide a method for detecting air to liquid (and liquid to air) boundaries in a fluidic channel, comprising using an optical sensor (can be the same optical sensor 62 now used as a reflective object sensor); emitting light onto a detection spot of a channel with an infrared emitting diode; detecting the reflective light with a phototransistor, wherein the emitter and detector are side by side housed.

Some embodiments also provide a method for measuring liquid volumes (and air volumes) in a fluidic channel, comprising recording the time when an air liquid boundary and liquid air boundary passes a detection spot; calculating the volume of liquid (or air) passing the detection spot based on the flow rate (pump rate, volume velocity) and time.

Some embodiments provide methods for detecting the transition of air liquid and liquid air boundaries in a fluidic sealed channel. Some embodiments use an optical reflective object sensor 62 (in FIG. 9A), properly positioned under the fluidic channel where the contents of the channel are moving by controlled means like a pump device. The fluidic channel can be sealed with a clear film, such as, a bottom seal, and it is contemplated that many transparent and/or translucent material scan be used. The optical sensor 62 can be connected to a signal processing circuitry, generating a signal that is monitored by a microprocessor which timely distinguishes air and liquid by the difference in the amount of reflected light produced by air and liquid.

Figure 11A:
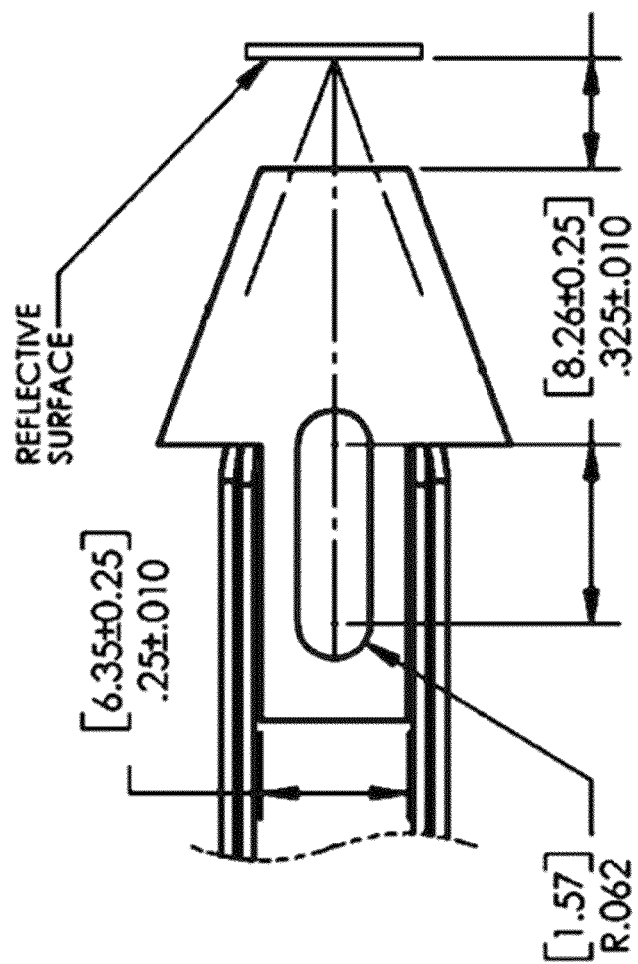
FIG. 11A is an illustration of a mechanical outline of a sensor used in an embodiment.
Figure 11B:
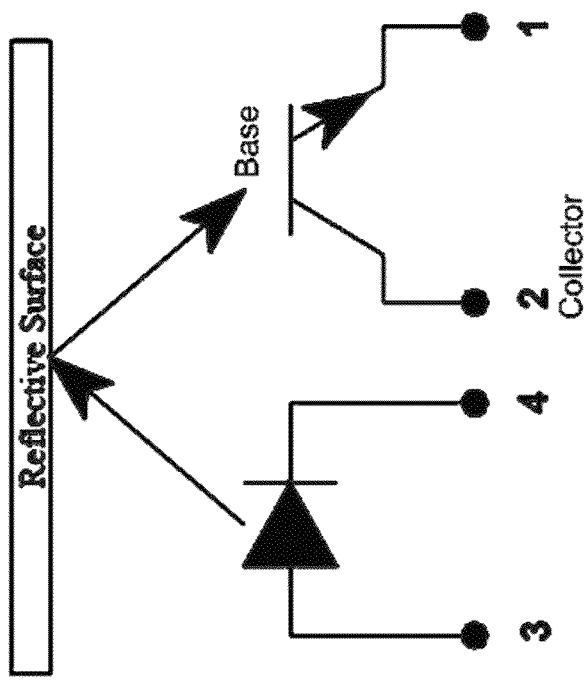
FIG. 11B is a schematic drawing of a sensor used in an embodiment.

The sensor 62 can be an optical sensor and may use an infrared emitting diode and a NPN (NPN is one of the two types of bipolar transistors, consisting of a layer of P-doped semiconductor (the "base") between two N-doped layers) silicon phototransistor, as depicted in FIG. 11A, which is an outline of a sensor. FIG. 11B is an electrical schematic of a sensor. A current passed between the nodes 3 and 4 can cause an infrared light to be transmitted. Depending on the reflection, base current is formed by the reflected light striking the junction and the phototransistor can convert received power to a collector current, which is converted to a voltage and fed into a microprocessor, which converts the analog signal to a digital readout in a rapid manner.

Figure 11C:
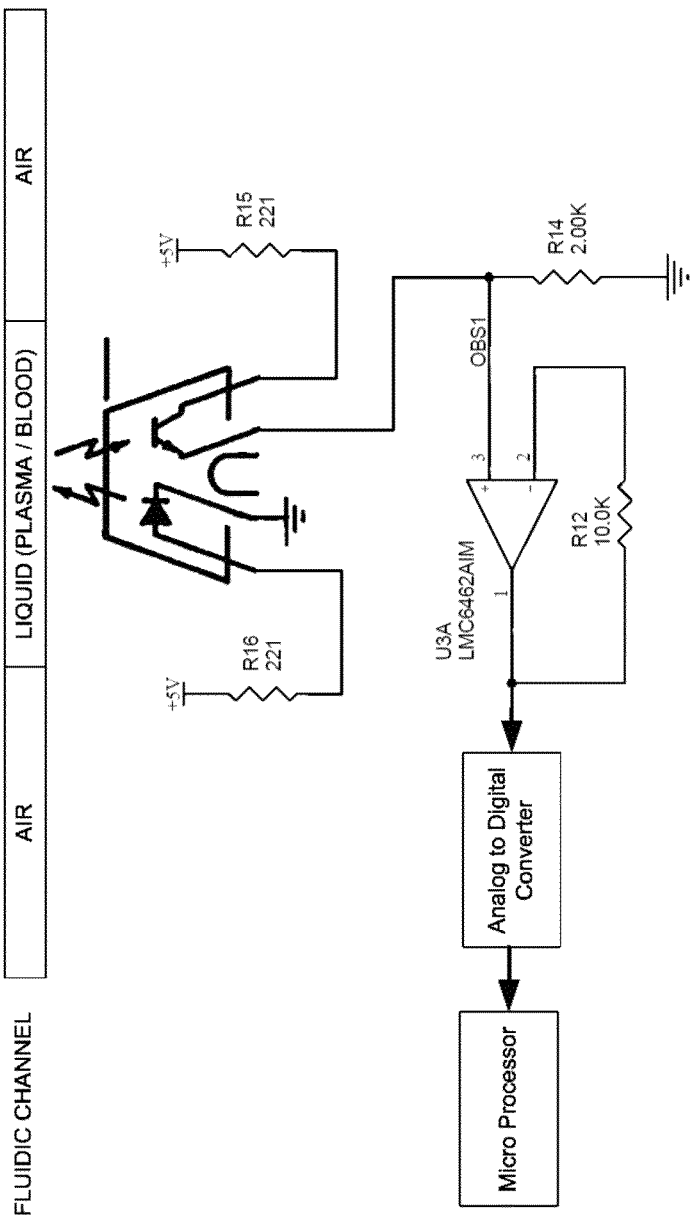
FIG. 11C is a schematic drawing of a detection system used in an embodiment.

FIG. 11C, which shows electrical schematics of a detection system, depicts how the sensor can be connected to a microprocessor in order to produce a measurement directly correlated with the contents of the fluidic channel. The contents being the following three entities: AIR, LIQUID, WET (channel that had liquid in it once, but now has air in it). The difference between AIR and WET are that the content is air but the walls of the fluidic channel have a film of liquid in WET and AIR is strictly air filled. The liquid/air detection methods are able to detect state transitions from AIR to LIQUID, LIQUID to WET and, WET to LIQUID.

Figure 11D:
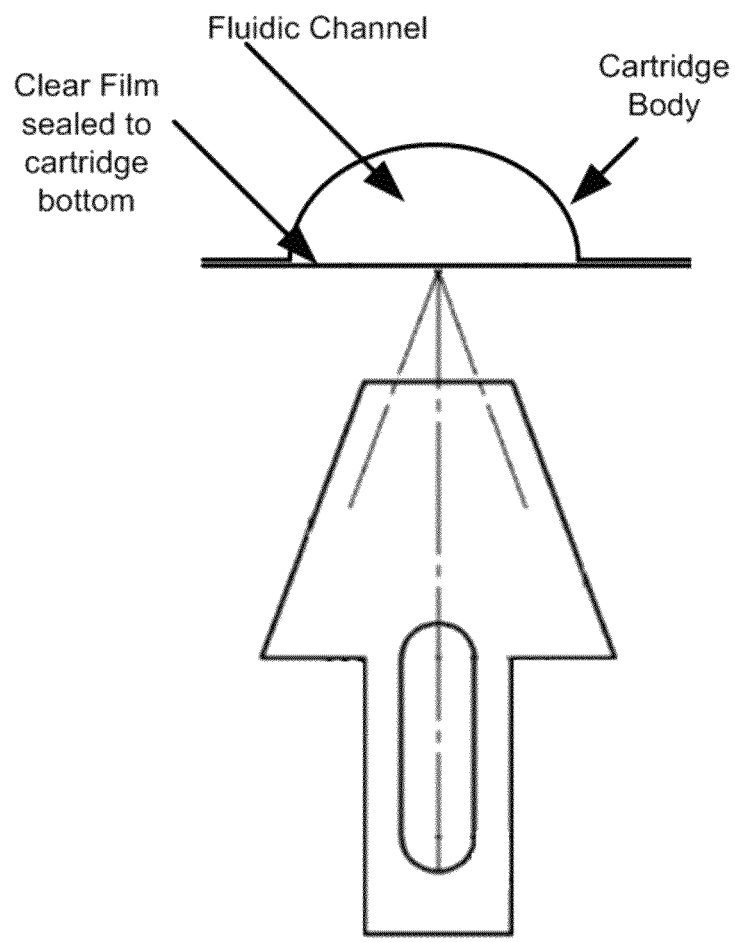
FIG. 11D is an illustration of a cross-section of a fluidic channel used in an embodiment.

An illustration of a cross section of a fluidic channel is depicted in FIG. 11D. The bottom has a clear film that is sealed to the body of the cartridge, with a sensor positioned to the center of a fluidic channel.

Figure 12:
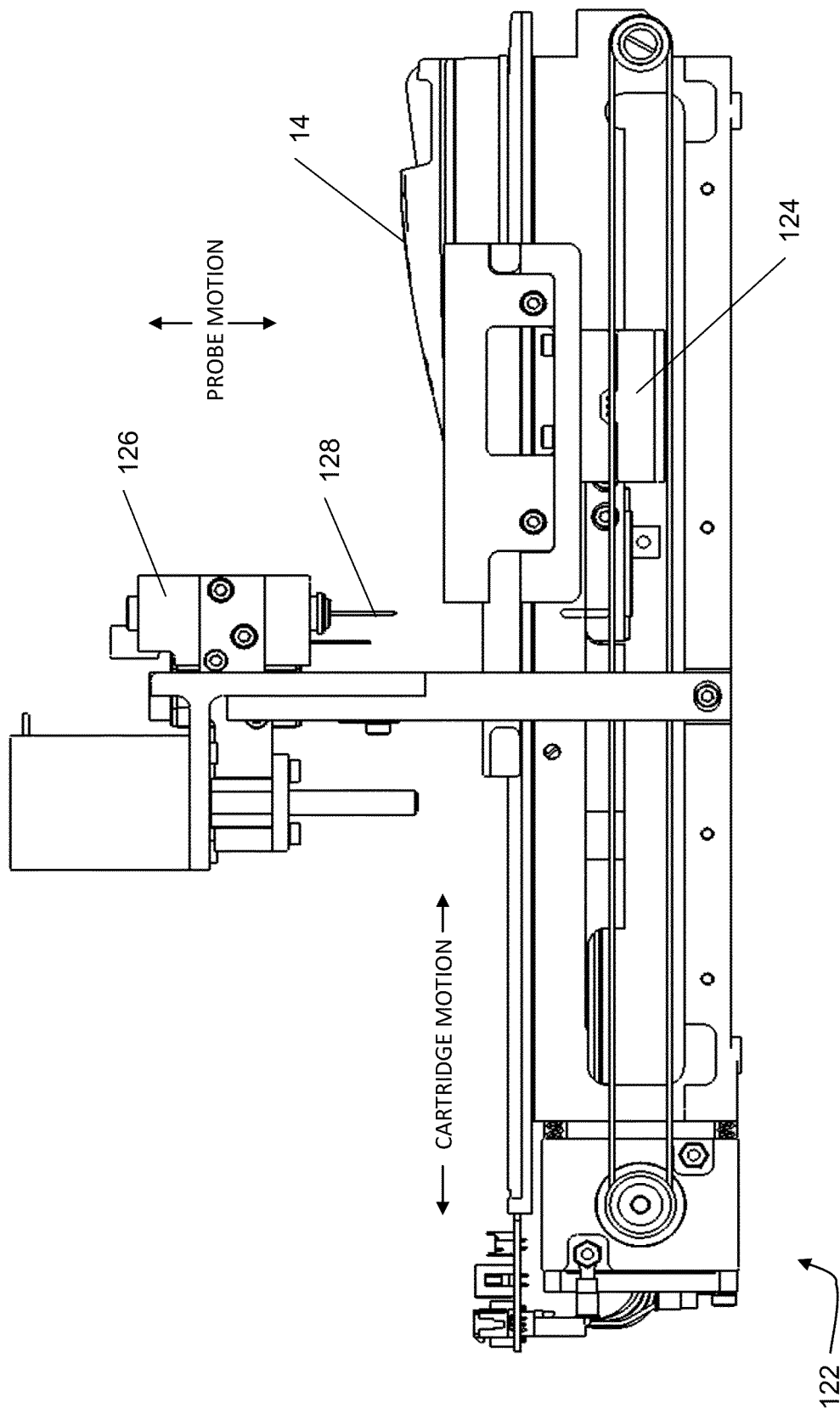
FIG. 12 is a schematic drawing of a motion mechanism used in the diagnostic system of an embodiment.

In a diagnostic system, a cartridge may have multiple channels to conduct similar diagnostics sample preparations or tests. In some embodiments, only one sensor 62 is used or is necessary, and a cartridge motion mechanism 122 (See, e.g., FIG. 12) can move the cartridge 14 to predetermined positions to align the fluidic channels with the optical sensor 62. In FIG. 12, the cartridge 14 is positioned on a cartridge carriage 124 which has an axis of motion along the horizontal. As the cartridge 14 is moved horizontally, back and forth with the cartridge carriage 124, a probe assembly 126 moves along a vertical axis to facilitate a probe's 128 interaction with the cartridge 14.

While a fluidic channel is being monitored by a sensor, fluid motion can be activated by a pump 140 connected to tubing 138a, 138b, 138c and connected to a probe 128a, 128b (e.g., hollow needle that can make fluidic connection with the fluidic channels inside a cartridge), depicted in FIG. 13. A fluidic system 130 is depicted in FIG. 13 illustrating some of the main components in the fluidic system, including a first probe 128a and a waste probe 128b, a non-ECL detection system 134, an ECL detection system 136, a pump 140, and a fluidic pathway 138a, 138b, 138c, usually in the form of a tubing assembly or passageway. The majority of the components of the fluidic system 140 are contained within the diagnostic system 12 that is fluidically connected to the cartridge 14.

Figure 14:
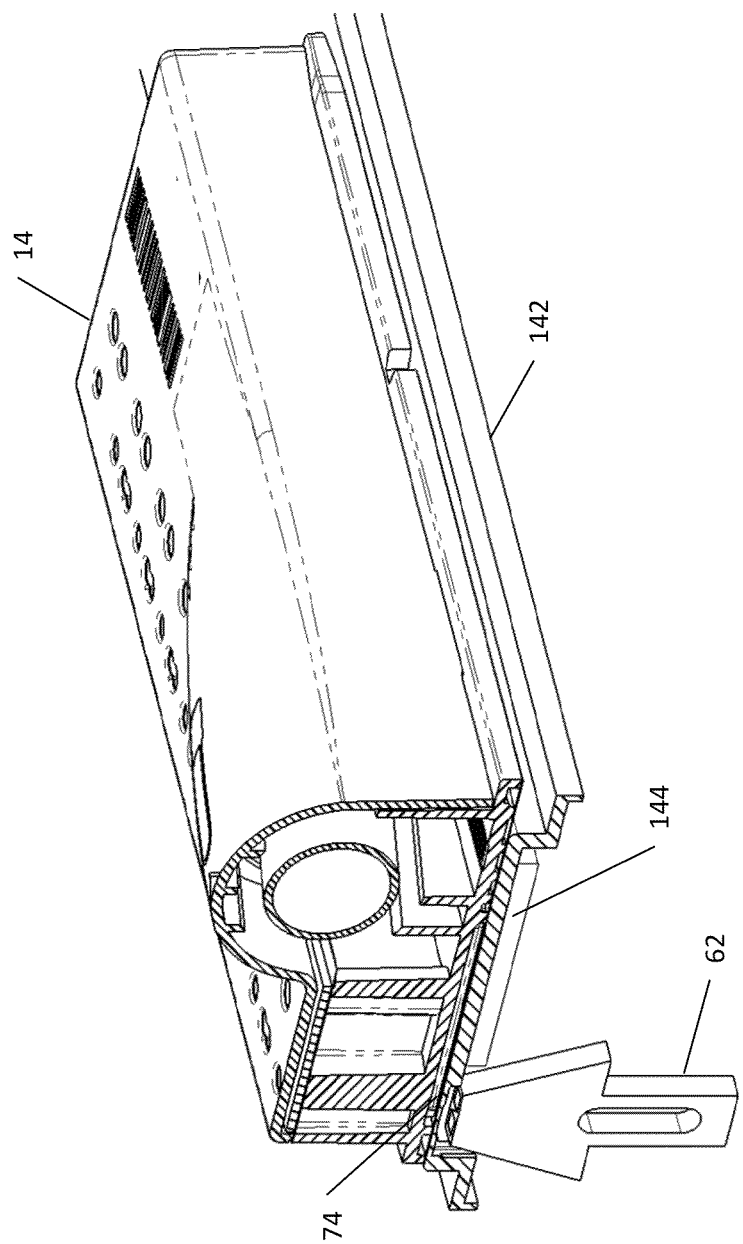
FIG. 14 is a perspective view of an optical sensor in relation to a sectioned view of a cartridge of an embodiment.

FIG. 14 illustrates the spatial arrangement between an optical sensor 62 and a cartridge 14 as it is positioned on an incubator of the diagnostic instrument and as used in the embodiments herein. In some embodiments, a cartridge 14 sits flat on an incubator plate 142 and can move on the incubator plate 142 to position the channels at the bottom of the cartridge 14 such that the optical sensor 62 is aligned at the center of the cartridge channel. A printed circuit board 144 under the incubator plate 142 controls the surrounding electrical components. A cartridge 14 can have the ability to run multiple tests each contained in the fluidic channels. During those tests, the functionality of air/liquid detection can be used to verify the location of the fluid within the fluidic pathways and the volumes of the segments of fluid in the fluidic pathways.

Figure 15:
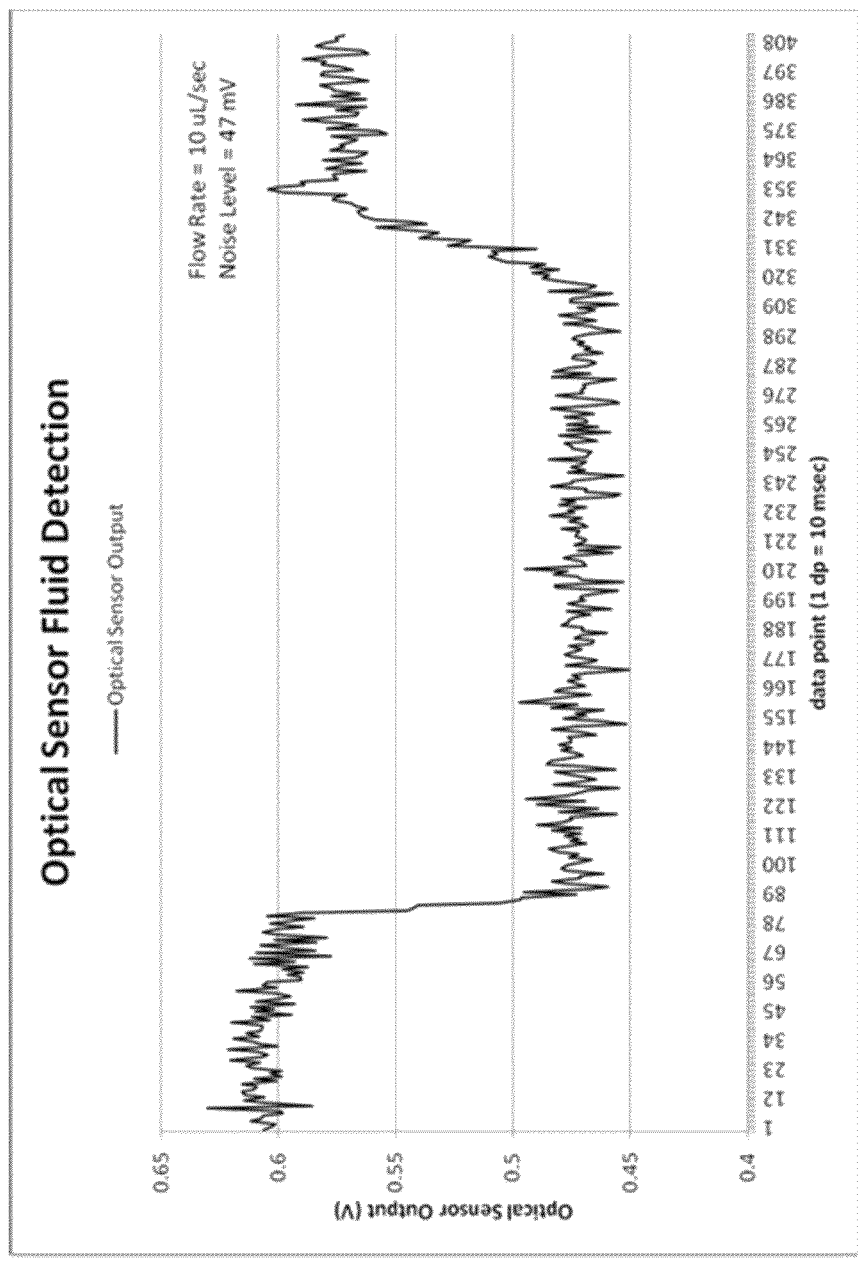
FIG. 15 is a graphical representation of a moving liquid slug detected by a sensor of an embodiment.

The sensor 62 located at the bottom of the cartridge 14 positioned at the optimal distance away from the cartridge 14, monitoring the contents of the cartridge, can be used for verification of volume, detection of presence of undesired air bubbles, verification of the location of the sample, detecting undesired leaks and/or undesired clogs in the fluidic channels. A typical output from such a system monitoring the fluidic channel where a volume of liquid is passed is shown in FIG. 15 (moving liquid volume detected by the sensor) and as described in Example 1.

Figure 16A:
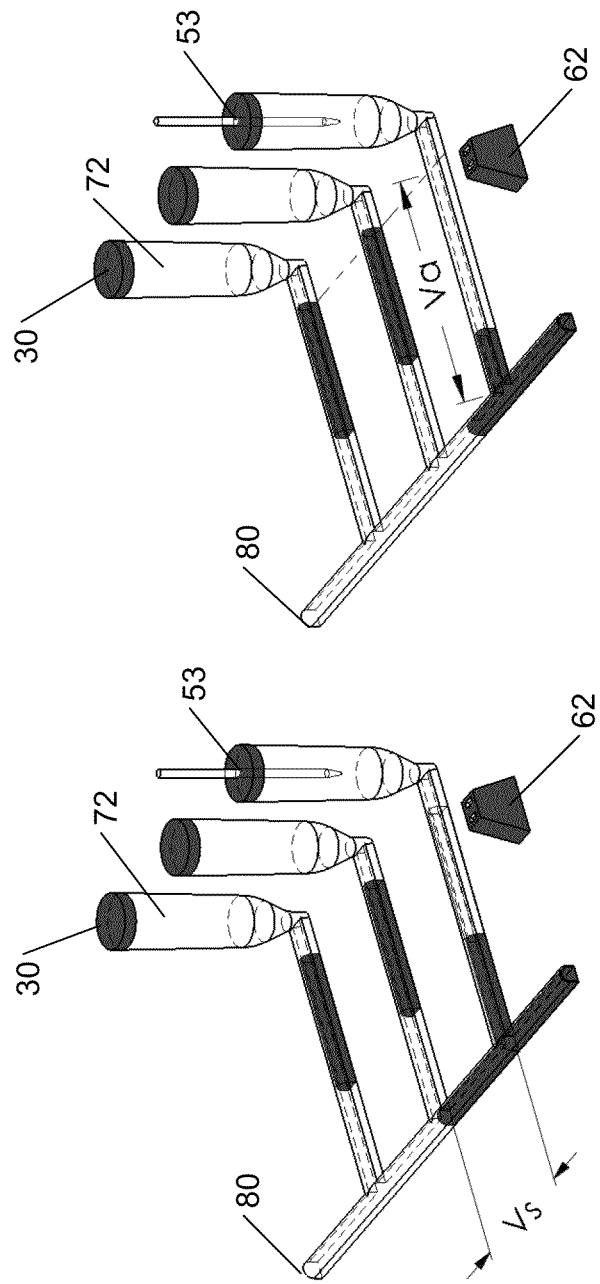
FIG. 16A is a schematic drawing illustrating an example sequence to detect leaks in a fluidics system of an embodiment.
Figure 16B:
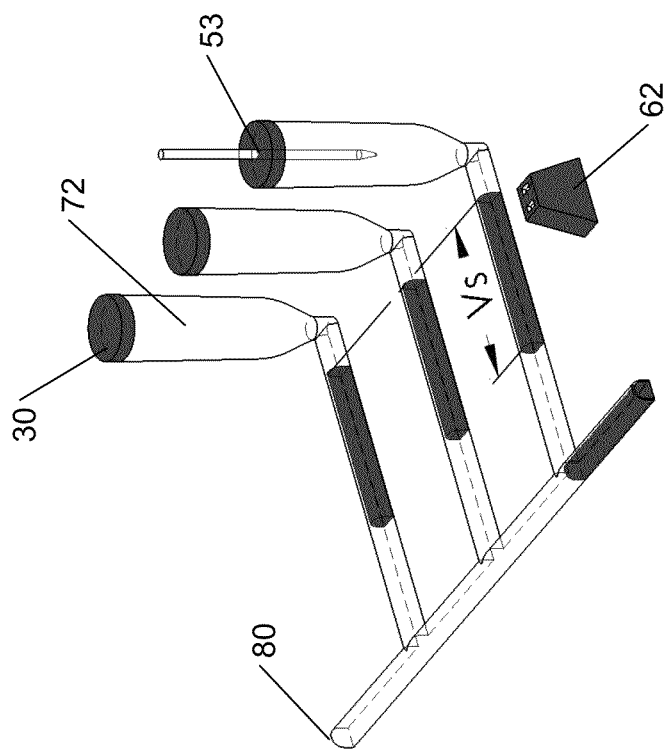
FIG. 16B is a schematic drawing illustrating a point in which a sample has reached a sensor of an embodiment.
Figure 16C:
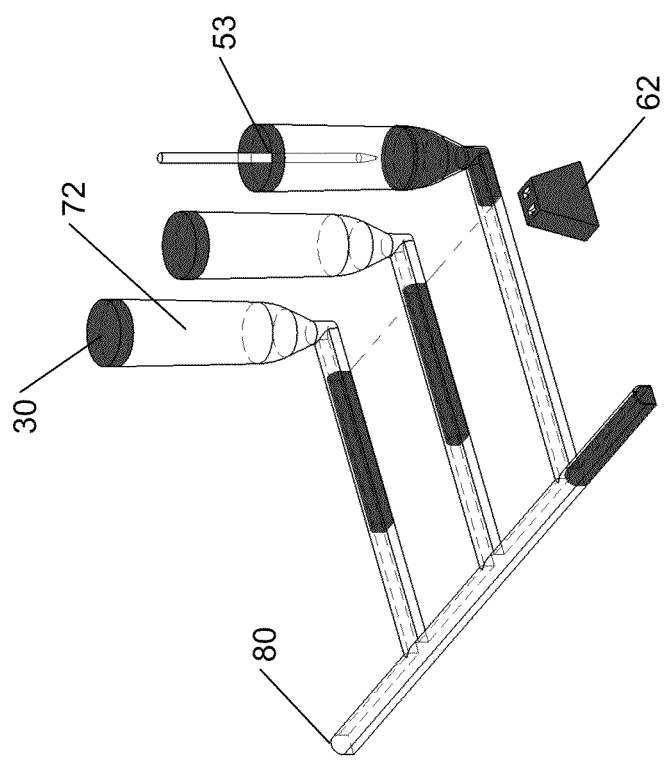
FIG. 16C is a schematic drawing illustrating when a sample has passed a sensor of an embodiment.

In some embodiments, the ability to detect air and liquid boundaries with proper software is used to detect air and clogs in a fluidic system, the presence of leaks and clogs will produce inaccurate results, proper diagnostics will enable the system not to generate any results, rather than wrong results. FIGS. 16A-16C illustrate an example of a sequence of operations to detect leaks in the fluidic system described in Example 2.

The methods of the present disclosure allow for verification of volume, detection of presence of undesired air bubbles, verification of the location of the sample, detecting undesired leaks and/or undesired clogs in the fluidic channels which can be used as a diagnostics mechanism by software to detect undesired behavior with the system that could produce erroneous results if not otherwise detected. Detection of the air to liquid and liquid to air transition can also be used for volume measurement of a liquid volume (more likely a sample that contains the antigen for detection, which the volume is important in measuring precise and accurate concentration) by the use of software.

The liquid/air detection methods are simple and inexpensive methods to detect liquid to air and air to liquid transaction in a sealed fluidic channel. Fluidic volumes can be computed and verified by properly detecting the edges of a liquid volume, e.g., which is being moved by a pump at a constant flow rate. Air bubbles can be identified in otherwise expected liquid volumes, and then can invalidate results obtained from such channel, e.g., if the air bubble is large enough to have compromised the integrity of the volume.

Bead Washing. After the aliquoted sample is mixed with the lyophilized (otherwise dry) reagents, and incubation of the mixture has begun, the steps of capturing the beads within the mixture and washing them for detection occurs next. In particular, the diagnostic system provides methods for washing off blood or plasma and free label from beads in a cartridge bead based assay with no human intervention. This includes, but is not limited to, methods for washing off a sample (e.g., patient's blood, plasma or bodily fluids) and free label from beads that have a specific antigen and label bound to them.

These methods can increase sensitivity and accuracy by decreasing the noise in the background, as well as not allowing the rest of the matrix (bodily fluids) from exiting the cartridge (which contains the sample and reagents) and entering and possibly contaminating the instrument (performing the detection). The methods achieve a highly effective wash method, by capturing the beads to be washed in a magnetic field, and then passing a liquid-and-air combination over the beads, in a fluidic channel using a very small amount of wash liquid.

In certain embodiments, the methods include steps to remove a patient's blood or plasma from the beads, for example, so that when the beads enter the diagnostic instrument for detection, there are no detectable remnants of a specific patient sample contaminating the diagnostic instrument. In certain other embodiments, the methods include steps to remove the matrix containing free label that has not bound to beads, for example, so that they do not contain relevant information to the measurement, in order to reduce the background signal generated during the detection of the label that has bound to beads. Some embodiments wash the patient's sample off from the beads, after the binding reaction is completed, while using a very small amount of wash fluid.

Other embodiments use a cartridge-based system where all reagents are housed on the cartridge (eliminating the need to use an externally connected reagent apparatus to a diagnostic instrument). It is advantageous to keep the volumes to be stored on the cartridge small, in a manner such that the resulting footprints for cartridges and diagnostic instruments are small, such as, for example, in the case of an diagnostic instrument for a point of care setting. One advantage of some of these embodiments is that it eliminates human intervention and it allows for a more precise and accurate measurement hence better diagnostics, by reducing the measurement background.

Figure 7B:
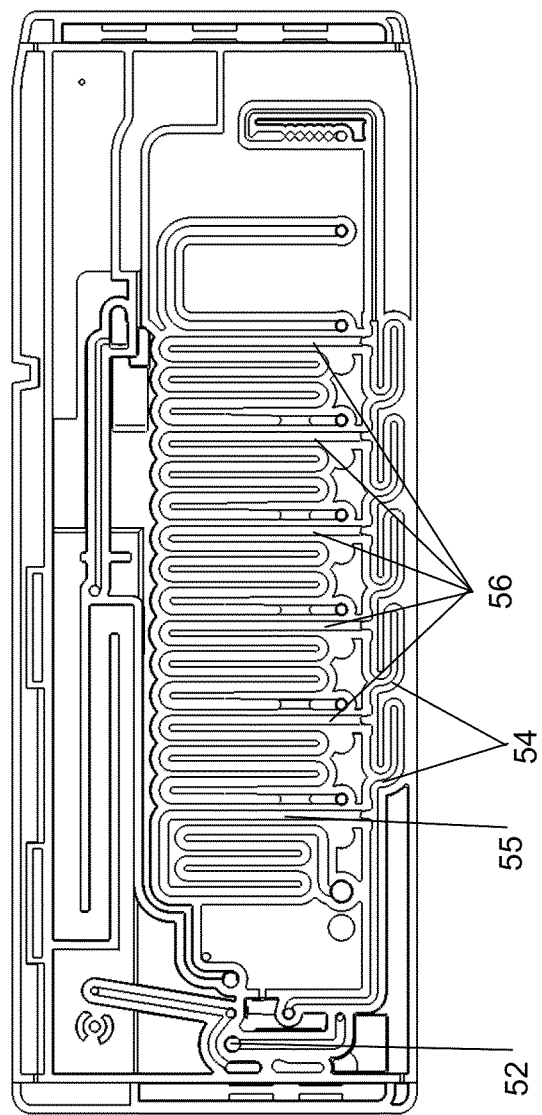
FIG. 7B is a bottom view of a cartridge depicting fluidic channels of a cartridge of an embodiment.

FIG. 7B shows an example of a cartridge 14 depicting multiple tests with fluidic channels. FIG. 9A shows an example of a fluidic channel arrangement for a single test that can be on a cartridge. Each test contains a sealed well (active mix well 72), a vented opposite end 80, and a fluidic channel 78 connecting the sealed well to the vented end 80. The cartridge 14 can contain multiples of these processing channels for different tests, e.g., to apply to the same patient's sample.

FIG. 13 shows an example of a fluidic system of an apparatus containing a probe connected to the inlet of a detection system, the detection module (flow cell assembly), the outlet of the detection module connected to the inlet of the pump, a pump, another probe connected to the outlet of the pump, tubing connecting these components, and the cartridge containing the fluidic channels and its interaction with the fluidic system.

Figure 17:
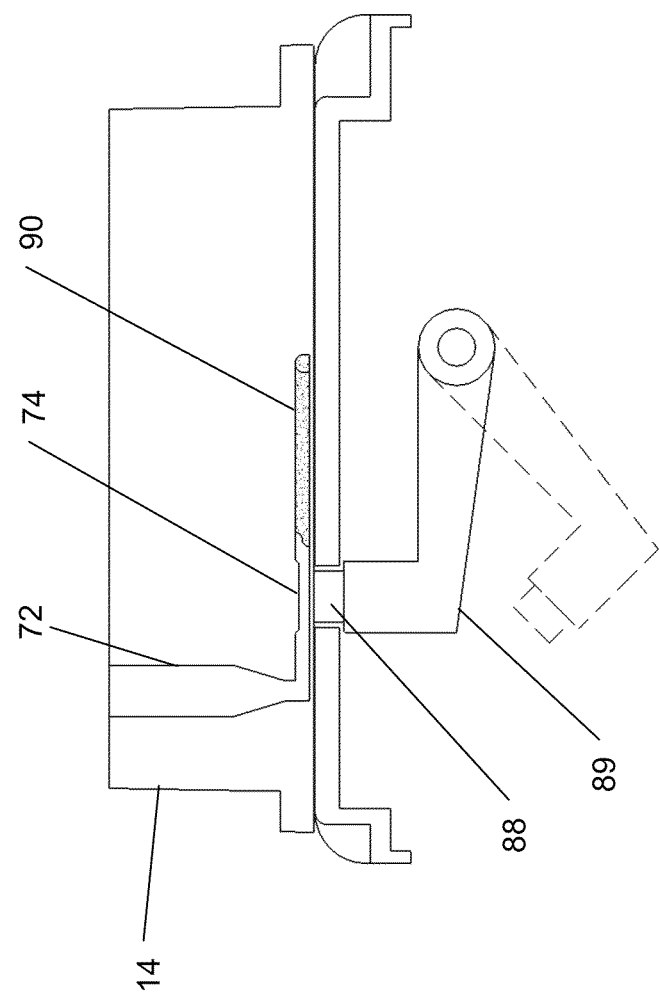
FIG. 17 is an illustration of a mechanism for capturing beads in a sample of an embodiment.

FIG. 17 shows an example of a mechanism that captures beads within a sample within a magnetic field created by a magnet 88 attached to an arm 89 under the cartridge 14. The probe 128 connected to the inlet of the fluidic system pierces the sealed well creating a sealed connection between the fluidic system and the sample 90. The pump in the fluidic system creates a negative pressure and moves the fluid 90 across the magnet 88 toward the sealed well.

FIG. 9D shows exemplary dimensions of a wash channel 78 and a bead capture zone 74 with the width of the wash channel 78 and the bead capture zone 74 being 0.045 inch, a max height of the bead capture zone 74 being 0.024 inch, a max height of the wash channel 78 being 0.036 inch. In this embodiment, a bead capture zone 74 was designed to have a lower ceiling than the wash channel 78 so that the vertical distance beads travel during the bead capture process is shorter at the bead capture zone than at the wash channel. This promotes more effective bead capturing within a given time. The same feature proving the diameter changes is used to facilitate a turbulent flow in order to help suspend the beads in liquid after they have been washed.

Typically, human intervention is used to wash beads that have been used to form immunoassays. Beads in a fluidic sample of measurement external to the "detection instrument" have been washed with buffer in order to remove the free label and other possible contaminants from the beads. These human intervention methods require the transfer of the beads from and to the diagnostic instrument. To minimize human intervention and allow a more precise and accurate measurement, the present disclosure provides a cartridge-based system, in which the sample is washed within the cartridge before isolating the washed sample into the system for measurement.

An exemplary apparatus used for a method disclosed for the present disclosure may comprise a cartridge that contains a well that is sealed by a septum where the fluidic system connects to it via a probe. The apparatus can also include a fluidic channel that connects the sealed well to a vented opening, as well as a reservoir for buffer solution. The cartridge can have a thin film bottom sealing the fluidic channels as well as allowing the necessary magnetic field to be applied to capture the beads in the fluid and hold on to them while they are being washed. The apparatus can also include a fluidic system that contains an inlet, an outlet, a detection module, a pump, and tubing connecting these components that can generate fluidic motion in the fluidic channels in a cartridge, as well as aspirate and dispense fluids and air in and out of the cartridge.

FIG. 13 shows an example of such a fluidic system where a probe at the inlet of the fluidic system pierces a sealed well in a cartridge forming a sealed connection between the sample and the fluidic system. The pump in the fluidic system creates a positive or a negative pressure in order to move the sample in a fluidic channel that connects the pierced well to the vented end 80 in a cartridge. The fluid in the channel contains the sample (e.g., antigens bound between beads and tag labels), unbound tag labels, and matrix (e.g., bodily fluids). As depicted in FIG. 17, an arm 89 with a magnet 88 can be raised under the cartridge 14 while the fluid 90 moves across a narrow channel (capture zone 74) where the magnet 88 is in contact with the cartridge bottom 26. The magnet 88 creates a magnetic field capturing the magnetic beads bound to the antigen within the sample while the sample is moved at a slow rate across the bead capture zone 74. FIG. 17 shows an example of a mechanism that raises an arm with a magnet 88 attached to its end to the bottom of the cartridge 14. FIG. 9C shows a channel with a low ceiling where the bead capturing takes place. A channel with a low ceiling reduces the vertical distance beads need to travel during bead capture process with said capturing mechanism. Once after the beads are captured in an area, the magnet arm is lowered such that the magnet 88 is no longer in contact with the cartridge 14; and the cartridge is moved such that the inlet is above the buffer reservoir (see, e.g., 64 in FIG. 8A). In the buffer reservoir, the fluidic system aspirates a staggered combination of liquid and air and stores them in the tubing. The cartridge 14 is moved back to the location where the beads are captured 74 and, the magnet arm is aligned again with the beads when the magnet 88 is raised and contacts the cartridge bottom 26. The magnet arm is raised and holds the beads (in the magnetic field) while the staggered combination of liquid and air is dispensed across the captured beads washing the matrix and the unbound tag labels off from the beads.

In certain embodiments, the wash methods can include a sequence of operations in order to capture and wash the beads effectively. For example, the magnet can be raised as the incubated sample, which may contain a patient's blood or plasma mixed and incubated with reagents that contain the beads, flows due to a fluidic system, across a portion of the channel where the magnet makes contact. Using a pump, the reagent pack can be aspirated (consecutive chunks or segments of liquid buffer and air) into the fluidic system (tube) via the probe of the diagnostic instrument. The composition of the pack can influence the cleaning quality. The amount of liquid buffer needed to wash the beads has been determined by the diagnostic system, accomplished by having air and liquid combination in a reagent pack. A liquid air boundary has shown to be very effective in brushing the surface of the beads.

Using the pump and the fluidic system, the reagent pack is able to flow over into the fluidic channel that is sealed at the probe end and vented on the other side of the patient sample, while the beads remain held to the bottom of the cartridge by the magnet. The above sequence can push the sample away, so that the beads can sit in the clean buffer. The magnet then can be lowered and a series of push-pull action is applied in the pump (aspirate, dispense) that moves the fluid with the beads back and forth inside the cartridge across the bead capture zone to re-suspend, into clean buffer, beads that had been pulled to the bottom of the cartridge. This provides the washed beads in the clean buffer that now can be aspirated into the fluidic system to be analyzed in the detection module.

Preventing Reuse of a Single Use Device.

Some embodiments of the diagnostic instrument provide methods to prevent reuse of a single use clinical device (i.e., a cartridge), for example, by detecting fluid flow characteristics that differ between a used and an unused device. This contributes to the prevention of false results incurred by inappropriate use of a used single use clinical device and also prevents the time loss incurred by processing an inappropriate test.

In certain embodiments, detection of a previously used single use clinical device is accomplished by means of a pump used to generate a pressure and a pressure sensor to detect either a vented path that is vented in a used clinical device but not in an unused clinical device or an unvented path that would be unvented in a used clinical device but not in an unused clinical device. This test allows a diagnostic instrument to quickly determine the use status of a clinical device and to disallow processing of a used single use clinical device.

Some embodiments provide a means of detecting a previously used single use clinical device, including detecting a previously used single use clinical device for the purpose of preventing invalid results. Other embodiments provide a means of detecting a previously used single use clinical device by measuring pressure changes and/or a means of generating a positive or negative pressure and detecting the introduction of a previously used single use clinical device by changes in that pressure. Still other embodiments provide a means of detecting a previously used single use clinical device by use of a pump to establish or fail to establish a pressure within the used clinical device for subsequent measurement. Some embodiments provide a means of detecting a previously used single use clinical device by placing a pressure transducer within the fluidic channel that communicates with a device in order to measure a change or lack of change in an established pressure.

Figure 18:
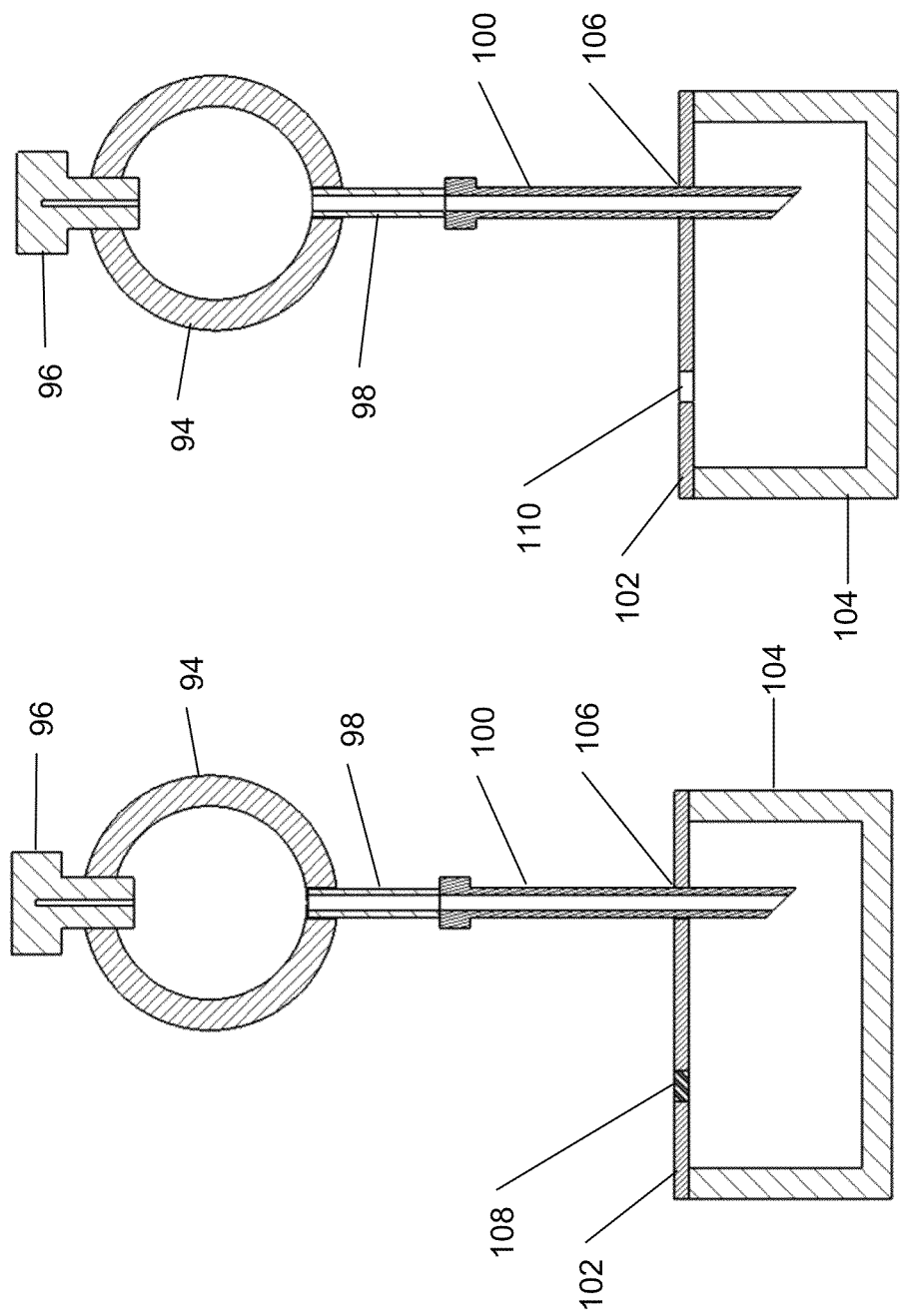
FIG. 18 is an illustration of the different configurations between a vented and an unvented diagnostic device of an embodiment.

In certain embodiments, single use clinical devices have seals, valves, or other features that control fluidic motion to enable processing of results whose fluidic flow state is changed during use, for example, with an opened valve or a pierced foil seal. In some embodiments, when the clinical device use is completed, a fluidic pathway configuration of a new device is no longer the same, such as a pierced foil seal or a valve left closed rather than open. By introducing and detecting a pressure in a fluidic pathway that should not be sealed or by failing to introduce a pressure in a fluidic pathway that should be sealed, a used single use clinical device can be detected and rejected as not usable thus preventing invalid results from being presented. FIG. 18 provides an illustration of an example of an unvented device on left and a vented device on right.

Certain embodiments provide methods to prevent reuse of a single use clinical device, for example, (i) by means of a pressure measurement to detect changes in the device brought about during use; (ii) by means of a pressure introduced into the used device and detecting a state only present in a used device; and/or (iii) by means of a pressure transducer to detect an expected pressure introduced into the used device and detecting a state only present in a used device.

Certain embodiments, such as that depicted in FIG. 18, provide a pump 94, being in fluidic communication with a pressure transducer 96. A fluidic pathway in the form of a tube 98, in communication with the pump chamber and leading to a hollow needle 100 with which it is also in fluidic communication. The needle 100 pierces a septum 102 on a single use clinical device 104 thereby creating an airtight seal 106 between the single use clinical device and the outer surface of the needle 100. Air is inserted into the single use clinical device by the pump after which the pressure in the system is monitored to determine if the pressure is maintained.

Case—1: Detecting a single use clinical device in which the test chamber is not vented 108 if the single use clinical device is used. Detection of a maintained pressure is indicative of a used single use clinical device whereas detection of a loss of pressure is indicative of an unused single use clinical device.

Case—2: Detecting a single use clinical device in which the test chamber is vented 110 if the single use clinical device is used. Detection of a maintained pressure is indicative of an unused single use clinical device whereas detection of a loss of pressure is indicative of a used single use clinical device.

Undesired reuse of a single use clinical device can be prevented by means of the detection of pressure changes and/or pressure status within the device to determine its use status. In some embodiments, a system is comprised of a pump 94 capable of pressurizing the single use clinical device to a level at which pressure level and pressure change can be detected. A pressure transducer 96 is used to monitor the pressure within the pressurized fluidic channels of the system. Typically, but not necessarily, a tube 98 is used to connect the pump 94 to a hollow needle 100, probe or fitment (hereafter called needle, but the present disclosure is not limited to a needle) in fluidic communication to both the pump 94 and the needle 100. The pressure transducer 96 may be situated anywhere within the fluidic pathway. The location of the pressure transducer 96 may be within the pump chamber 96 as long as the chamber is in fluidic communication with the tube 98 and needle 100 during detection. The needle 100 is placed in fluidic communication with a target chamber of the single use clinical device by a convenient means forming an air-tight connection to the single use clinical device. Pressure is introduced into the chamber of the single use clinical device 106 by means of the pump 94 or other controlled pressure source and then measured to determine the state of the pressure over some elapsed time.

In certain other embodiments, processing of a single use clinical device can be designed to deliberately leave the device in a fluidic state other than its unused state. A single use clinical device can be further designed to allow an air-tight fluidic connection by the needle 100 for a used single use clinical device detection. This may be in the form of a vent which is opened or closed during normal processing or may be a separate feature designed specifically for use detection reasons. If the feature is unvented 108 or closed after use, then pressurization is attempted and then measured, detection of the established pressure indicates a used single use clinical device, whereas detection of a loss of pressure indicates an unused device. If the feature is vented 110 or opened after use, then pressurization is attempted and then measured. Detection of the established pressure indicates an unused single use clinical device, whereas detection of a loss of pressure indicates a used device.

The present disclosure is not restricted to a vent and it is contemplated that any structure such as a valve, a pierced membrane, a broken feature, or activation of a material whose fluid flow properties may be readily changed would serve the same function.

Pump Storage Fluid.

A pump storage liquid prevents/inhibits the formation of solids between the piston and cylinder by, for example, not evaporating and/or by solubilizing any residual salt or solids present in the dead volume of a pump. This non-volatile liquid acts as a lubricant for the seal or tight fitting piston and cylinder set of a pump within the diagnostic instrument. Stiction is avoided because lubricant persistently fills the gap between the piston and cylinder. In this manor the pump storage liquid prevents the pump seals or tight fitting piston and cylinder set from drying out and therefore prevents freezing, seizing, or stiction.

Additionally, the present disclosure provides a pump storage liquid which enables the pump to recover from storage without wetting the seals or tight fitting piston and cylinder set. The minimum amount of pump storage liquid required to protect a pump can be very low, e.g. 1 mL. The pump storage liquid can be present in an amount ranging from about 1 mL to about 2 mL, from about 1 mL to about 1.5 mL, or from about 1.5 mL to about 2 mL. The minimum amount of pump storage liquid required to protect the pump depends on the gap volume between the piston and cylinder set. For example, a one inch diameter piston and one inch length chamber with a 2 micron gap between piston and cylinder has a gap volume of 4 µL. This is the minimum amount of pump storage liquid required to protect such pump.

The pump storage fluid can be stored on the cartridge of the diagnostic system and used at the end of the each cartridge run.

Desiccant Competition with Dry Reagents.

In the design of disposable diagnostic devices, it is desirable to have lyophilized or dried assay reagents to increase product stability at room temperature storage. It is also desirable to process the assay with a liquid buffer, not limited to but useful for rehydration, washing, or assay processing. In certain embodiments, it is advantageous to contain both the dried reagent on the same device as the liquid buffer. Protection of the dried reagent from the liquid buffer increases the stability of the assay and the shelf life of the device.

Thus, some embodiments provide an improved method for storing both dry reagents and liquid buffer on board a disposable device. This method is not limited to diagnostic devices but lends itself to the aforementioned issues as well. Some embodiments comprise a method using desiccant material used specifically to extend the shelf life of dry reagents on a disposable device that stores both liquid and dry reagents where there is a pathway connecting the dry reagents and vapors from the liquid reagents. For example, the present disclosure provides a desiccating system for a clinical device that has both stored liquids and dry reagents which is able to prevent water from interacting with the dry reagents and for which the cartridge has an open passageway from the interior location of the dry reagent to exterior where a desiccant is located.

Some embodiments can keep the dried reagents stable in the presence of liquid for a minimum of two years.

Figure 19A:
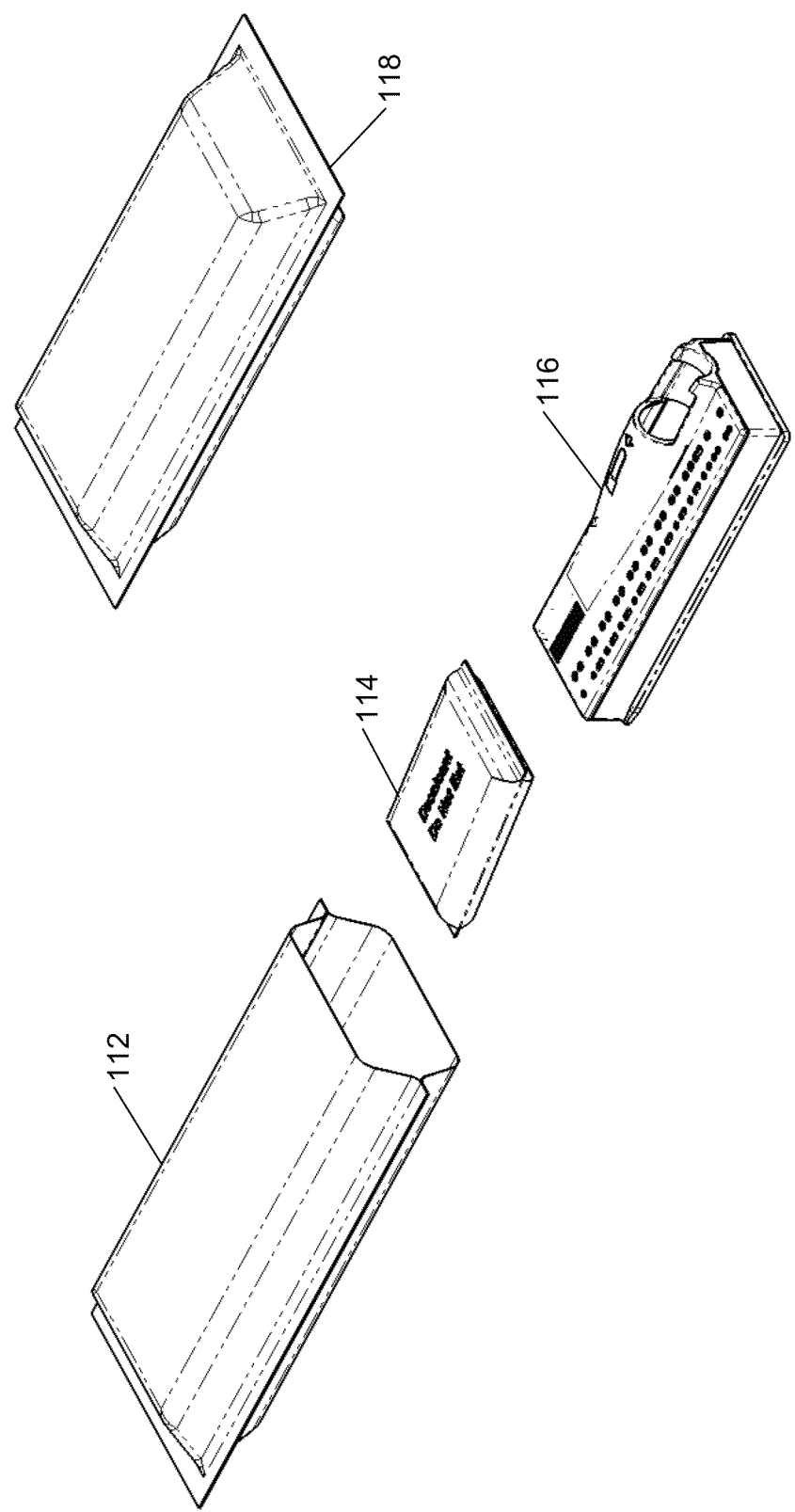
FIG. 19A is an exploded view of cartridge packaging including a desiccant of an embodiment.
Figure 19B:
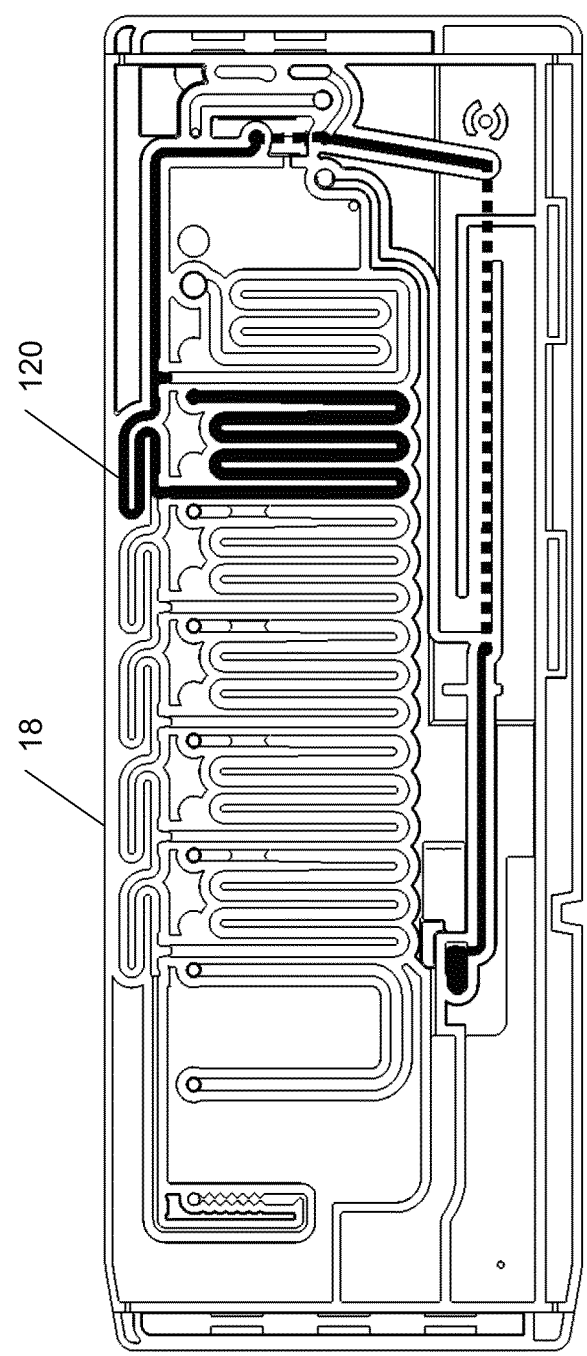
FIG. 19B is a bottom view of a cartridge highlighting a path from the atmosphere to the nearest dry region on a cartridge of an embodiment.

FIG. 19A shows the over pack 112, a desiccant 114, a disposable device 116 and a packaged device with desiccant 118 of an exemplary embodiment. FIG. 19B shows a path 120 from the atmosphere surrounding a disposable device to the nearest dry reagent on board the disposable. Evaporated water in atmosphere can travel along this diffusion distance and adversely affect the dry reagents.

In one embodiment, the moisture vapor transfer from the liquid reagent wells on the disposable device to the exterior is sufficiently small so that the chemical concentrations of the liquid reagents aren't adversely affected by evaporation over the shelf life and so that the dry reagents on the same device are not prematurely rehydrated over the shelf life by the evaporated liquid.

By way of a prophetic example only, a cross sectional area that water vapor can diffuse through is approximately 524 mm$^2$ and because of a 1° taper in the molded disposable, the wall thickness varies at the wells from about 0.040 in. to about 0.055 in.

A disposable device can be made from a Cyclic Olefin Copolymer, e.g., with the Trade name of TOPAS®. The moisture vapor transmission rate (MVTR) for TOPAS® grade 5013 is about 0.03 g mm/(m$^2$ day) at 23° C. and 85% RH. Using the average wall thickness of about 0.047 in., the transfer rate is therefore [0.03 g mm/(m$^2$ day)] {(524×10$^{-6}$ m$^2$)/(0.047×25.4 mm)}=13.2 µg/day/assay.

Accordingly, it can be predicted based on the calculations above, that to achieve over a two year shelf life, a disposable device will release about 87 mg of water. The device is pouched in a foil seal and there is a path 120 through a needle that will allow the ambient (within the foil pouch) to reach the dry reagents. If this released 87 mg of water is allowed to reach the dry reagents, the shelf life of the device is shortened greatly. In order to keep the amount of evaporated water to be less than 6.6% of the DRIERITE® mass (6.6% is the maximum moisture absorption with a strong affinity), the amount of DRIERITE® has to be greater than 1.3 g. DRIERITE® desiccants are made from the naturally occurring mineral, gypsum (Calcium Sulfate), and are available in several varieties designed to solve all types of drying problems. DRIERITE® is an all-purpose drying agent for the efficient and rapid drying of air, industrial gases, refrigerants, organic liquids and solids. The smallest bag of DRIERITE® readily sold is 3 g, which is more than sufficient for the device.

DRIERITE® is sufficiently aggressive and out-competes the dry reagents for water absorption that slowly diffuse from the liquid buffer and through the plastic walls of the disposable. While DRIERITE® is described herein as an exemplary desiccant, the present disclosure is not limited to the use of DRIERITE® as the desiccant.

All publications, patents and patent applications mentioned in this specification are herein incorporated by reference in their entirety into the specification to the same extent as if each individual publication, patent or patent application was specifically and individually indicated to be incorporated herein by reference. Also incorporated by reference is any supplemental information that was published along with any of the aforementioned publications, patents and patent applications. For example, some journal articles are published with supplemental information that is typically available online.

Citation or discussion of a reference herein shall not be construed as an admission that such is prior art to the present disclosure.

As used herein the transitional term "comprising" is open-ended. A claim utilizing this term can contain elements in addition to those recited in such claim. Thus, for example, the claims can read on methods that also include other steps not specifically recited therein, as long as the recited elements or their equivalent are present.

For the purpose of illustrating the invention, there are depicted in the drawings certain embodiments of the invention. However, the invention is not limited to the precise arrangements and instrumentalities of embodiments depicted in the drawings.

The following examples are merely illustrative and intended to be non-limiting.

EXAMPLES

Example 1

Computing the Volume of a Liquid

FIG. 15 illustrates a typical output from a system monitoring the fluidic channel where a volume of liquid is passed. In FIG. 15, the horizontal axis is time (each data point is 10 milliseconds (ms)) and the vertical axis is the analog sensor output in volts. There is a 130 mV difference between the high (representing AIR in the system) and the low (representing LIQUID) in the system. There is a 110 mV difference between the low (representing LIQUID) and the high (after data point 342, representing WET). The noise level on the signal is about 47 mV, which is low enough to enable clear distinction of air and liquid in the channels.

A sensor output was used to compute the volume of the liquid, by computing the time that the liquid was present and multiplying by the pump's flow rate during the fluid motion. Also, the fact that there were no interruptions in the "low" signal (e.g., remains low, does not go up to the 0.6 V level) indicated that there were no air bubbles in the fluid volume. In this example above, air and liquid boundaries happened twice, one at about time point=81 and the other at about 318 (in this example where the flow rate was 10 µL/sec, liquid volume deleted was then 318−81=237 data points where each was 10 ms, making the total volume detected 23.7 µl.

Example 2

Detecting Leaks in a Fluidic System

FIG. 16A illustrates an example of a sequence of operations to detect leaks in the fluidic system. On a disposable cartridge where the patient sample was divided into aliquots of equal amounts each was processed independently in a multiple test cartridge (a cartridge that can run multiple tests with the same patient's sample). Sample Vs was aspirated into the channel, via the probe at the probe entry site 53. The sample volume was aspirated through a probe at the probe entry site 53 sealed to a septum 30, into the desired channel. The software reset a timer (T0) and commanded the pump to aspirate at a fixed flow rate (Fr) while monitoring the optical sensor's output until an air to liquid boundary was detected (FIG. 16B), as soon as it was detected the firmware made a copy of the current timer (T1).

The pump continued aspirating the sample, and as soon as a liquid to air transition was detected, the software made the copy of the timer (T2), after which the pump was stopped (FIG. 16C, depicting that sample passed the sensor and enabled volume measurement).

The following are examples of calculations that were used to determine clogs, leaks and/or verification and when desired correction of volumes.

Vx=(T1−T0)*Fr will be compared to Va, Vx>Va will indicate a leak. If Vx>>Va may indicate a clog in between pump and the probe.

Vy=(T2−T1)*Fr will be compared to Vs to verify the accuracy of the aliquot.

What is claimed is:

1. A cartridge for use in a diagnostic system, comprising:
   structural members;
   a body and a cover, wherein the body and the cover mate together;
   at least one reagent handling station formed from the body;
   a septum seal between the body and cover capable of establishing a liquid and air-tight seal for the at least one reagent handling station and capable of establishing a fluidic connection with at least one probe of a diagnostic instrument in the diagnostic system;
   a bottom seal adjacent to the body;
   at least one fluidic channel formed from the body and sealed by the bottom seal, wherein the bottom seal defines in part the volume of the at least one fluidic channel; and
   a mounting apparatus for mounting a blood collection tube to the cartridge, the mounting apparatus comprising:
   a framework comprising of at least one of the structural members of the cartridge; and
   at least one needle capable of establishing a fluidic connection between the cartridge and the blood collection tube when the at least one needle pierces a septum of the blood collection tube, wherein the framework is configured to guide the blood collection tube into a position such that the blood collection tube is capable of being fixed at an angle ranging from about 45° to about 5° from a horizontal axis of the cartridge.

2. The cartridge of claim 1, wherein the at least one reagent handling station comprises a pocket formed in the at least one reagent handling station.

3. The cartridge of claim 2, wherein the pocket is capable of reducing dead volume within the at least one reagent handling station when the at least one probe engages the septum seal to contact a fluid contained therein and allows the at least one probe to contact fluid within the pocket.

4. The cartridge of claim 1, wherein the at least one reagent handling station has a low moisture vapor transmission rate.

5. The cartridge of claim 1, wherein the at least one reagent handling station comprises at least two reagent handling stations, and wherein one of the at least two reagent handling stations contains a pump storage liquid.

6. The cartridge of claim 1, wherein the at least one reagent handling station comprises at least two reagent handling stations, and wherein one of the at least two reagent handling stations is initially empty and is capable of receiving liquid from another portion of the cartridge.

7. The cartridge of claim 1, wherein each of the reagent handling stations are initially filled with liquid except one, which is initially empty and is capable of receiving liquid from another portion of the cartridge.

8. The cartridge of claim 1, wherein there are at least two reagent handling stations, and wherein each of the reagent handling stations are initially filled with electrochemiluminescent (ECL) read buffer except one, which is initially empty and is capable of receiving liquid from another portion of the cartridge.

9. The cartridge of claim 1, wherein the at least one reagent handling station is part of a closed fluidic pathway.

10. The cartridge of claim 1, wherein the at least one reagent handling station is part of a closed fluidic pathway, and wherein liquid emptied from a filled reagent handling station is capable of filling an empty reagent handling station using a closed fluidic system.

11. The cartridge of claim 1, further comprising a top seal, comprising:
   at least one barrier layer capable of reducing or preventing evaporation of liquids stored in the cartridge; and
   at least one laminating element, wherein the at least one laminating element joins the at least one barrier layer to the cartridge to seal the liquids and/or dry reagents within the cartridge.

12. The cartridge of claim 11, wherein the at least one laminating element is made from a material chosen from a heat seal coating, a pressure sensitive adhesive (PSA), a pressure sensitive adhesive tape, a thermal adhesive, a transfer tape, a transfer adhesive, a double sided tape, a tie layer, and an adhesive film.

13. The cartridge of claim 11, wherein the at least one laminating element comprises a pressure sensitive adhesive (PSA).

14. The cartridge of claim 11, wherein the at least one barrier layer comprises a material with a low moisture vapor transmission rate.

15. The cartridge of claim 14, wherein the at least one barrier layer comprises a material with a moisture vapor transmission rate that is at least two times lower than a material used to form the cartridge.

16. The cartridge of claim 11, wherein the at least one barrier layer comprises a material chosen from aluminum foil, aluminum alloy foils, metal alloy foils, high moisture vapor transmission rate films, high barrier films, cyclic olefin copolymer (COC) films, films made of fluorinated-chlorinated resins, duplex films, and triplex films.

17. The cartridge of claim 11, wherein the at least one barrier layer comprises aluminum foil.

18. The cartridge of claim 11, wherein the at least one barrier layer is puncturable.

19. The cartridge of claim 11, wherein the top seal comprises a lid that seals at least one reagent handling station.

20. The cartridge of claim 1, wherein the septum seal further comprises:
    a septum layer;
    a support layer, wherein the support layer is adjacent to the septum layer; and
    at least one laminating element, wherein the at least one laminating element is between the septum layer and the support layer.

21. The cartridge of claim 20, wherein the septum layer is re-sealing and the support layer is substantially rigid.

22. The cartridge of claim 20, wherein the septum layer has at least one of the properties chosen from pierceable, reversibly stretchable, elastic, reversibly compressible, self-sealing, fluid and gas exchange preventable, and probe sealable.

23. The cartridge of claim 20, wherein the septum layer has all of the properties of pierceable, reversibly stretchable, elastic, reversibly compressible, self-sealing, fluid and gas exchange preventable, and probe sealable.

24. The cartridge of claim 20, wherein the septum seal has at least one probe-addressable location.

25. The cartridge of claim 20, wherein the septum seal has a plurality of probe entry sites addressable by the probe at least once during operation.

26. The cartridge of claim 20, wherein the septum seal has a plurality of probe entry sites that are addressable more than once or re-usable.

27. The cartridge of claim 20, wherein the septum seal has at least one probe entry site addressable by the at least one probe, wherein the at least one probe entry site does not allow the at least one probe to pierce the septum layer and allows a vent to be formed at the probe entry site.

28. The cartridge of claim 20, wherein the septum seal has at least one probe entry site addressable by the at least one probe, wherein the septum seal is puncturable.

29. The cartridge of claim 20, wherein the septum layer is made from a material chosen from synthetic rubber, silicone rubber, butyl rubber, natural rubber, elastomers, fluoroelastomers, copolymers of hexafluoropropylene, copolymers of vinylidene fluoride, terpolymers of tetrafluoroethylene, terpolymers of vinylidene fluoride, terpolymers of hexafluoropropylene, and perfluoromethylvinylether polymers.

30. The cartridge of claim 20, wherein the septum layer comprises silicone rubber.

31. The cartridge of claim 20, wherein the support layer comprises a material that is more rigid than the septum seal and has at least one of the properties of being capable of reducing stretch and tension of the septum layer, being capable of providing rigidity to the septum seal, being capable of providing stiffness to the septum seal, being capable of reinforcing the septum seal, being capable of reducing elongation of the septum layer, and is capable of being puncturable.

32. The cartridge of claim 20, wherein the support layer comprises a material that is more rigid than the septum seal and has all of the properties of being capable of reducing stretch and tension of the septum layer, being capable of providing rigidity to the septum seal, being capable of providing stiffness to the septum seal, being capable of reinforcing the septum seal, being capable of reducing elongation of the septum layer, and is capable of being puncturable.

33. The cartridge of claim 20, wherein the support layer is made from a material chosen from metals and polymers.

34. The cartridge of claim 20, wherein the support layer comprises aluminum foil.

35. The cartridge of claim 20, wherein the support layer has a thickness of less than or equal to 7 mils, less than or equal to 6 mils or less than or equal to 5 mils.

36. The cartridge of claim 20, wherein the support layer has a thickness of less than or equal to 7 mils, less than or equal to 6 mils, less than or equal to 5 mils, less than or equal to 4 mils, less than or equal to 3 mils, less than or equal to 2 mils, less than or equal to 1 mils, or less than or equal to 0.5 mils.

37. The cartridge of claim 20, wherein the support layer comprises a stiff layer capable of facilitating the piercing of the septum layer by a probe.

38. The cartridge of claim 20, wherein the support layer comprises a stiff layer capable of reducing stretching of the septum layer during a probe entry or withdrawal.

39. The cartridge of claim 20, wherein the at least one laminating element is made from a pressure sensitive adhesive (PSA), a thermal adhesive, a transfer tape, a transfer adhesive, a double-sided tape, a tie layer, or an adhesive film.

40. The cartridge of claim 20, wherein the at least one laminating element comprises a pressure sensitive adhesive (PSA).

41. The cartridge of claim 20, wherein the septum seal is die-cuttable.

42. The cartridge of claim 20, wherein the septum seal is a component of a closed fluidic pathway within the cartridge.

43. The cartridge of claim 1, further comprising:
    a top seal located between the body and the cover, wherein the top seal comprises:
        a support layer; and
        a second laminating element, wherein the second laminating element is between the support layer and the body, and
    wherein the septum seal comprises:
        a septum layer; and
        a first laminating element between the septum layer and the top seal.

44. The cartridge of claim 1, wherein a dead volume in the blood collection tube is less than 25% of an initial fill volume, less than 20% of an initial fill volume, less than 10% of an initial fill volume, or less than 5% of an initial fill volume.

45. The cartridge of claim 1, wherein the framework is capable of guiding the blood collection tube into a position that is capable of being fixed at an angle of about 7° from the horizontal axis of the cartridge.

46. The cartridge of claim 1, wherein the framework consists of a cartridge body.

47. The cartridge of claim 1, wherein the framework consists of structural members other than a cartridge body.

48. The cartridge of claim 1, wherein the framework is comprised of a combination of a cartridge body and at least one other structural member.

49. The cartridge of claim 1, wherein the framework further comprises a holding apparatus capable of preventing removal of the blood collection tube.

50. The cartridge of claim 49, wherein the holding apparatus comprises a tang.

51. The cartridge of claim 1, wherein the at least one needle comprises:
a first needle capable of introducing gas into the blood collection tube; and
a second needle capable of extracting blood from the blood collection tube.

52. The cartridge of claim 1, further comprising a lubricant, wherein the lubricant is located on the at least one needle.

53. The cartridge of claim 1, wherein the at least one needle is mounted in a recessed area within the framework.

54. The cartridge of claim 1, wherein the at least one needle is mounted in a recessed area within the framework and secured with an adhesive provided in the recessed area.

55. The cartridge of claim 1, wherein the cartridge is capable of separating plasma out of the blood.

56. The cartridge of claim 1, further comprising a blood filtration module, wherein the mounting apparatus is adjacent to the blood filtration module.

57. The cartridge of claim 1, wherein the mounting apparatus is adjacent to the at least one reagent handling station.

58. The cartridge of claim 1, wherein the mounting apparatus is capable of contacting a blood collection tube.

59. A method of extracting and filtering blood from a blood collection tube, comprising:
positioning the blood collection tube in the cartridge of claim 1;
introducing gas into the blood collection tube;
flowing the blood from the blood collection tube into the at least one fluidic channel which extracts the blood;
flowing a portion of the blood through a blood filtration module;
filtering plasma from the blood into a plasma cache of the cartridge; and
detecting an air liquid boundary using an optical sensor of the diagnostic instrument.

60. The cartridge of claim 1, wherein the at least one fluidic channel comprises a primary channel, a secondary channel, and at least one receiver channel.

61. A method of metering a sample within the cartridge of claim 60, comprising:
drawing a first volume of plasma from a sample reservoir into a primary channel of the cartridge, wherein the primary channel is filled up to a predetermined volume detected by an optical sensor of a diagnostic instrument;
emptying any remaining plasma from the sample reservoir not used to fill the primary channel into a secondary channel using an optical sensor of the diagnostic instrument to detect an air liquid boundary; and
drawing a second volume of plasma from the primary channel into at least one receiver channel, wherein the second volume is a predetermined volume,
wherein the process is repeated until each receiver channel holds the second volume of plasma, and
wherein each of the steps performed are independent of pump accuracy.

62. The method of claim 61, wherein the sample reservoir has a volume which is greater than or equal to the sum of the first and second volumes.

63. The method of claim 61, wherein the sample reservoir has a volume ranging from about 125 µL to about 135 µL, about 135 µL to about 150 µL, about 150 µL to about 175 µL, and about 175 µL to about 200 µL.

64. The method of claim 61, wherein the sample reservoir has a volume of about 200 µL.

65. The method of claim 61, wherein the primary channel has a volume less than the sample reservoir.

66. The method of claim 61, wherein the primary channel has a volume ranging from about 125 µL to about 135 µL, about 135 µL to about 150 µL, about 150 µL to about 175 µL, and about 175 µL to less than about 200 µL.

67. The method of claim 61, wherein the primary channel has a volume of about 150 µL.

68. The method of claim 61, wherein the secondary channel has a volume less than the sample reservoir.

69. The method of claim 61, wherein the secondary channel has a volume ranging from about 125 µL to about 135 µL, about 135 µL to about 150 µL, about 150 µL to about 175 µL, and about 175 µL to less than about 200 µL.

70. The method of claim 61, wherein the secondary channel has a volume of about 150 µL.

71. The method of claim 61, wherein the secondary channel has a volume greater than the difference in volume between the sample reservoir and the primary channel volumes.

72. The method of claim 61, wherein each of the primary channel, the secondary channel and the receiver channels is fluidically connected to a pump of the diagnostic instrument using a probe pierced through a septum seal.

73. A method of mixing a sample within the cartridge of claim 1 in a diagnostic system to form a testing sample and providing the testing sample to an analyzer of the diagnostic system, comprising:
drawing the sample within the at least one fluidic channel;
detecting an air liquid transition of the sample using an optical sensor of the diagnostic system, wherein the at least one fluidic channel is fluidically connected to a pump of the diagnostic system;
drawing the sample into a first well containing an assay reagent, wherein the first well is fluidically connected to the pump of the diagnostic system and the at least one fluidic channel;
wetting a lyophilized reagent in a mixing well with the sample to form a sample mixture within the mixing well of the cartridge; and
mixing the sample mixture with the assay reagent to form a testing sample.

74. The method of claim 73, wherein the mixing comprises back and forth motions of the pump of the diagnostic system.

75. The method of claim 73, wherein the testing sample is substantially free of foam.

76. The method of claim 73, wherein the testing sample is substantially free of foam and foam-trapped beads.

77. The method of claim 74, wherein the back and forth motion of the pump produces a flow of the sample mixture of greater than 5 microliters per second.

78. The method of claim 73, further comprising moving the testing sample into an incubation zone in the diagnostic system.

79. The method of claim 73, further comprising:
moving the testing sample into an incubation zone in the diagnostic system; and
incubating the testing sample at a temperature greater than 1° C. and for a period of time greater than one second.

80. The method of claim 73, further comprising:
moving the testing sample into an incubation zone in the diagnostic system using the pump; and
sensing an air liquid boundary using an optical sensor of the diagnostic system.

81. The method of claim 73, wherein the cartridge further comprises at least one testing sample well, and
wherein the providing step comprises:
moving the testing sample to a third well of the cartridge:
introducing a probe from the diagnostic system into the third well of the cartridge; and
moving the testing sample into the analyzer of the diagnostic system using the probe.

82. The method of claim 81, wherein introducing the probe comprises piercing the septum seal of the cartridge using the probe.

83. The method of claim 73, wherein each of the steps performed in the method are independent of pump accuracy.

84. The method of claim 73, wherein the providing step is repeated one or more times corresponding to the number of testing sample wells when there are two or more testing sample wells.

85. The method of claim 73, wherein drawing the sample further comprises metering the sample using a metering device.

86. The method of claim 73, further comprising:
filtering plasma out of blood, wherein the plasma is the sample before drawing the sample within the at least one fluidic channel.

87. The method of claim 73, further comprising:
measuring the volume of the testing sample within the at least one fluidic channel using the pump of the diagnostic system; and
detecting a first air liquid transition and a second liquid air transition using an optical sensor of the diagnostic system.

88. The method of claim 73, further comprising a washing step after the mixing step.

89. A bead wash method for separating blood, plasma, and free labels from labeled beads within the cartridge of claim 1 of a diagnostic system, comprising:
drawing a combination of blood, plasma, and free labels from labeled beads into the at least one fluidic channel using a pump of the diagnostic system;
detecting an air liquid transition of the combination using an optical sensor of the diagnostic system
contacting a magnet to a portion of the at least one fluidic channel to capture the beads within the sample at the portion of the at least one fluidic channel;
separating the labeled beads from the blood, plasma, and free labels using the magnet; and
washing the blood, plasma, and free labels.

90. The method of claim 89, further comprising:
aspirating a wash liquid pack from the at least one probe fluidically connected to the pump of the diagnostic system, wherein the wash liquid pack comprises segments of liquid buffer and air, and wherein the wash liquid pack comprises cleaning qualities;
dispensing the wash liquid pack over the portion of the at least one fluidic channel with captured beads contacted by the magnet, wherein the portion of the at least one fluidic channel comprises a bead capture zone; and
removing the magnet from the bead capture zone.

91. The method of claim 90, wherein the wash liquid pack volume is less than 100 microliters.

92. The method of claim 90, wherein the wash liquid pack comprises a staggered combination of liquid and air.

93. The method of claim 90, wherein the wash liquid pack comprises a liquid-and-air combination.

94. The method of claim 90, wherein the wash liquid pack comprises alternating liquid segments and air segments within the at least one fluidic channel of the cartridge.

95. The method of claim 90, further comprising capturing the labeled beads in the bead capture zone of the at least one fluidic channel of the cartridge.

96. The method of claim 95, wherein the labeled beads make up greater than 99% of the volume within the bead capture zone after washing.

97. The cartridge of claim 1, the at least one fluidic channel comprising at least one difference in a cross sectional area between the at least one fluidic channel and the at least one reagent handling station.

98. The cartridge claim of 97, wherein the at least one difference in the cross sectional area ranges from about 0.0016 in$^2$ to about 0.0011 in$^2$.

99. A cartridge for use in a diagnostic system, comprising:
a body and a cover, wherein the body and the cover mate together;
a blood collection tube;
a blood collection tube mount configured to secure the blood collection tube to the cartridge at an angle ranging from about 45° to about 5° from a horizontal axis of the cartridge, wherein the blood collection tube mount has at least one needle to engage the blood collection tube and form a fluidic connection between the cartridge and the blood collection tube;
a septum seal between the body and the cover capable of establishing a liquid and air-tight seal for at least one reagent handling station and capable of establishing a fluidic connection with at least one probe of a diagnostic instrument in the diagnostic system;
a blood filtration module in fluidic communication with the blood collection tube mount; and
a plasma cache.

100. A cartridge for use in a diagnostic system, comprising:
a body and a cover, wherein the body and the cover mate together;
a blood collection tube mount configured to secure a blood collection tube to the cartridge at an angle ranging from about 45° to about 5° from a horizontal axis of the cartridge, wherein the blood collection tube mount has at least one needle capable of engaging the blood collection tube and capable of forming a fluidic connection between the cartridge and the blood collection tube;
at least one reagent handling station formed from the body;
a septum seal between the body and the cover capable of establishing a liquid and air-tight seal for the at least one reagent handling station and capable of establishing a fluidic connection with at least one probe of a diagnostic instrument in the diagnostic system; and
at least one fluidic channel formed from the body and sealed by a bottom seal, wherein the bottom seal defines in part the volume of the at least one fluidic channel.

101. A cartridge for use in a diagnostic system, comprising:
a body and a cover, wherein the body and the cover mate together;
a blood collection tube mount configured to secure a blood collection tube to the cartridge at an angle ranging from about 45° to about 5° from a horizontal axis of the cartridge, wherein the blood collection tube mount has at least one needle capable of engaging the blood collection tube and capable of forming a fluidic connection between the cartridge and the blood collection tube;
a blood filtration module in fluidic communication with the blood collection tube mount;
a plasma cache;
at least one reagent handling station formed from the body;
a septum seal between the body and the cover capable of establishing a liquid and air-tight seal for the at least one reagent handling station and capable of establishing a fluidic connection with at least one probe of a diagnostic instrument in the diagnostic system; and at least one fluidic channel formed from the body and sealed by a bottom seal, wherein the bottom seal defines in part the volume of the at least one fluidic channel.

* * * * *